US007449185B2

(12) United States Patent
Yamaguchi et al.

(10) Patent No.: US 7,449,185 B2
(45) Date of Patent: Nov. 11, 2008

(54) ANTIBODIES TO OCIF-BINDING MOLECULES

(75) Inventors: Kyoji Yamaguchi, Saitama (JP);
Hisataka Yasuda, Tochigi (JP);
Nobuaki Nakagawa, Tochigi (JP);
Nobuyuki Shima, Tochigi (JP);
Masahiko Kinosaki, Tochigi (JP);
Eisuke Tsuda, Tochigi (JP); Masaaki Goto, Tochigi (JP); Kazuki Yano, Tochigi (JP); Akihiro Tomoyasu, Tochigi (JP); Fumie Kobayashi, Tochigi (JP); Naohiro Washida, Tochigi (JP);
Ken Takahashi, Tochigi (JP); Tomonori Morinaga, Tochigi (JP); Kanji Higashio, Saitama (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 297 days.

(21) Appl. No.: 10/854,300

(22) Filed: May 27, 2004

(65) Prior Publication Data

US 2005/0003457 A1    Jan. 6, 2005

Related U.S. Application Data

(60) Continuation of application No. 10/167,182, filed on Jun. 11, 2002, which is a division of application No. 09/202,455, filed as application No. PCT/JP98/01728 on Apr. 15, 1998, now abandoned.

(30) Foreign Application Priority Data

| Apr. 15, 1997 | (JP) | ................................. 1997-97808 |
| Jun. 9, 1997 | (JP) | ............................... 1997-151434 |
| Aug. 12, 1997 | (JP) | ............................... 1997-217897 |
| Aug. 21, 1997 | (JP) | ............................... 1997-224803 |
| Dec. 2, 1997 | (JP) | ............................... 1997-332241 |

(51) Int. Cl.
*A61K 39/395* (2006.01)
*A61K 39/00* (2006.01)
*C07K 16/18* (2006.01)
*C07K 16/28* (2006.01)
*C12P 21/08* (2006.01)

(52) U.S. Cl. .............. 424/139.1; 424/130.1; 424/133.1; 424/141.1; 424/142.1; 424/143.1; 530/387.9; 530/388.1; 530/388.15; 530/388.22; 530/389.1

(58) Field of Classification Search .............. 530/387.1, 530/387.3, 387.9, 388.1, 388.15, 388.22, 530/388.85, 389.1
See application file for complete search history.

(56) References Cited

U.S. PATENT DOCUMENTS

| 4,179,337 A | 12/1979 | Davis et al. |
| 4,710,457 A | 12/1987 | Dupont et al. |
| 4,710,473 A | 12/1987 | Morris |
| 4,959,314 A | 9/1990 | Mark et al. |
| 5,118,667 A | 6/1992 | Adams et al. |
| 5,393,739 A | 2/1995 | Bentz et al. |
| 5,447,851 A | 9/1995 | Beutler et al. |
| 5,457,035 A | 10/1995 | Baum et al. |
| 5,578,569 A | 11/1996 | Tam |
| 5,585,479 A | 12/1996 | Hoke et al. |
| 5,599,708 A | 2/1997 | Mundy et al. |
| 5,623,053 A * | 4/1997 | Gastinel et al. ............. 530/350 |
| 5,658,756 A | 8/1997 | Rodan et al. |
| 5,843,678 A | 12/1998 | Boyle |
| 5,843,901 A | 12/1998 | Roeske |
| 5,985,832 A | 11/1999 | Roodman et al. |
| 6,015,938 A | 1/2000 | Boyle et al. |
| 6,017,729 A | 1/2000 | Anderson et al. |
| 6,087,555 A | 7/2000 | Dunstan et al. |
| 6,242,213 B1 | 6/2001 | Anderson |
| 6,242,586 B1 | 6/2001 | Gorman et al. |
| 6,271,349 B1 | 8/2001 | Dougall et al. |
| 6,284,485 B1 | 9/2001 | Boyle et al. |
| 6,284,728 B1 | 9/2001 | Boyle et al. |
| 6,284,740 B1 | 9/2001 | Boyle et al. |
| 6,288,032 B1 | 9/2001 | Boyle et al. |
| 6,316,408 B1 | 11/2001 | Boyle |
| 6,369,027 B1 | 4/2002 | Boyle et al. |

(Continued)

FOREIGN PATENT DOCUMENTS

AU          56180/98          7/1998

(Continued)

OTHER PUBLICATIONS

Benjamini et al., eds., Immunology: A Short Course, 2nd edition, Wiley-Liss, New York, p. 40.*

(Continued)

*Primary Examiner*—Elizabeth C. Kemmerer
(74) *Attorney, Agent, or Firm*—Knobbe, Martens, Olson & Bear, LLP

(57) ABSTRACT

The present invention relates to a novel protein which binds to Osteoclastogenesis Inhibitory Factor (OCIF-binding molecule; OBM), a process for preparing the same, DNA encoding said protein, a protein having an amino acid sequence encoded by this DNA, a method for producing said protein by genetic engineering technique, and a pharmaceutical composition containing said protein. In addition, screening methods for a substance for controlling expression of said protein using said protein and the DNA, a substance which inhibits or modulates the biological activity of said protein, or a receptor which transmits the action of said protein through binding to said protein, the substance obtained by the screening methods, and a pharmaceutical composition which contains this substance are disclosed. An antibody for said protein, a process for preparing the same, a measuring method of said protein using the antibody, and a medicine comprising the antibody are also disclosed.

57 Claims, 17 Drawing Sheets

U.S. PATENT DOCUMENTS

| | | |
|---|---|---|
| 6,419,929 B1 | 7/2002 | Anderson |
| 6,525,180 B1 | 2/2003 | Gorman et al. |
| 6,528,482 B1 | 3/2003 | Anderson et al. |
| 6,537,763 B2 | 3/2003 | Dougall et al. |
| 6,562,948 B2 | 5/2003 | Anderson |
| 6,569,430 B1 | 5/2003 | Waldmann et al. |
| 6,649,164 B2 | 11/2003 | Maraskovsky |
| 6,740,522 B2 | 5/2004 | Anderson et al. |
| 7,097,834 B1 | 8/2006 | Boyle |
| 2002/0081720 A1 | 6/2002 | Dougall et al. |
| 2002/0086826 A1 | 7/2002 | Anderson et al. |
| 2002/0086827 A1 | 7/2002 | Anderson |
| 2002/0127637 A1 | 9/2002 | Ni et al. |
| 2002/0150989 A1 | 10/2002 | Greene et al. |
| 2002/0169117 A1 | 11/2002 | Maraskovsky |
| 2003/0100069 A1 | 5/2003 | Ni et al. |
| 2003/0100488 A1 | 5/2003 | Boyle |
| 2003/0103978 A1 | 6/2003 | Deshpande et al. |
| 2003/0104485 A1 | 6/2003 | Boyle |
| 2003/0144480 A1 | 7/2003 | Gorman et al. |
| 2003/0166097 A1 | 9/2003 | Greene et al. |
| 2003/0175840 A1 | 9/2003 | Anderson et al. |
| 2004/0023313 A1 | 2/2004 | Boyle et al. |
| 2004/0033535 A1 | 2/2004 | Boyle et al. |

FOREIGN PATENT DOCUMENTS

| | | |
|---|---|---|
| AU | 68518/98 | 11/1998 |
| AU | 71205/98 | 11/1998 |
| EP | 0514130 A2 | 11/1992 |
| EP | 0514130 A3 | 11/1992 |
| EP | 0 526 905 A2 | 2/1993 |
| EP | 0 526 905 A3 | 2/1993 |
| EP | 0727211 A2 | 8/1996 |
| EP | 0874045 A1 | 10/1998 |
| EP | 0911342 A1 | 4/1999 |
| NZ | 330400 | 5/1999 |
| WO | 86/00922 A1 | 2/1986 |
| WO | 90/14363 A1 | 11/1990 |
| WO | 93/12227 A1 | 6/1993 |
| WO | 93/21946 A1 | 11/1993 |
| WO | 95/11308 A1 | 4/1995 |
| WO | 96/26217 A1 | 8/1996 |
| WO | 96/28546 A1 | 9/1996 |
| WO | 97/00317 A1 | 1/1997 |
| WO | 97/00318 A1 | 1/1997 |
| WO | 97/23614 A1 | 7/1997 |
| WO | 98/07840 A1 | 2/1998 |
| WO | 98/25958 | 6/1998 |
| WO | 98/28246 | 7/1998 |
| WO | 98/28424 A2 | 7/1998 |
| WO | 98/28426 A2 | 7/1998 |
| WO | 98/46644 A1 | 10/1998 |
| WO | 98/46751 A1 | 10/1998 |
| WO | 98/49305 A1 | 11/1998 |
| WO | 98/54201 A1 | 12/1998 |
| WO | 99/19468 A1 | 4/1999 |
| WO | 99/53942 A1 | 10/1999 |
| WO | 99/58674 A2 | 11/1999 |
| WO | 99/58674 A3 | 11/1999 |
| WO | 01 03719 A2 | 1/2001 |
| WO | 01 03719 A3 | 1/2001 |
| WO | 01 17543 A2 | 3/2001 |
| WO | 01 17543 A3 | 3/2001 |
| WO | 01 18203 A1 | 3/2001 |
| WO | 03002713 A2 | 1/2003 |

OTHER PUBLICATIONS

Burgess, T.C., et al., "The ligand for osteoprotegrin (OPGL) directly activates mature osteoclasts." *J. Cell Biol.*, 145:527-38 (1999).

Chambers, T.J., "Regulation of the differentiation and function of osteoclasts." *J. Pathol.* 192:4-13 (2000).

Fata, J.E., et al., "The osteoclast differentiation factor osteoprotegerin-ligand is essential for mammary gland development." *Cell* 103:41-50 (2000).

Faust, J., et al., "Osteoclast markers accumulate on cells developing from human peripheral blood mononuclear precursors." *J. Cell Biochem.* 72:67-80 (1999).

Fuller, K., et al., "Trance is necessary and sufficient for osteoblast-mediated activation of bone resorption in osteoclasts." *J. Exp. Med.*, 188:997-1001 (Sep. 7, 1998).

Gao, Y.H., et al., "Potential role of cbfa1, an essential transcriptional factor for osteoblast differentiation, in osteoclastogenesis: regulation of mRNA expression of osteoclast differentiation factor (ODF)." *Biochem. Biophys. Res. Commun.* 252:697-702 (1998).

Greenfield, E.M., et al., "Regulation of osteoclast activity." *Life Sci.* 65:1087-102 (1999).

Hsu, H., et al., "Tumor necrosis factor receptor family member Rank mediates osteoclast differentiation and activation induced by osteoprotegrin ligand." *Proc. Natl. Acad. Sci. USA* 96:3540-5 (1999).

Itonaga, I., et al., "Rheumatoid arthritis synovial macrophage-osteoclast differentiation is osteoprotegrin ligand-dependent." *J. Pathol.* 192:97-104 (2000).

Kim, D., et al., "Regulation of peripheral lymph node genesis by the tumor necrosis factor family member Trance." *J. Exp. Med.* 192:1467-78 (2000).

Kim, Nacksung, et al., "Diverse roles of the tumor necrosis factor family member Trance in skeletal physiology revealed by Trance deficiency and partial rescue by a lymphocyte-expressed Trance transgene." *Proc. Natl. Acad. Sci. USA* 97:10905-10 (2000).

Kinpara, K., et al., "Osteoclast differentiation factor in human osteosarcoma cell line." *J. Immunoassay* 21:327-40 (2000).

Kitazawa, R., et al., "Promoter structure of mouse RANKL/TRANCE/OPGL/ODF gene." *Biochim. Biophys. Acta* 1445:134-41 (1999).

Kong, Y.Y., et al., "Activated T cells regulate bone loss and joint destruction in adjuvant arthritis through osteoprotegrin ligand." *Nature* 402:304-9 (1999).

Kong, Y.Y. and J.M. Penninger, "Molecular control of bone remodeling and osteoporosis." *Exp. Gerontol.* 35:947-56 (2000).

Lacey et al., "Osteoprotegrin ligand is a cytokine that regulates osteoclast differentiation and activation", *Cell* 93:165-76 (Apr. 17, 1998).

Lacey et al., "Osteoprotegrin ligand modulates murine osteoclast survival in vitro and in vivo." *Am J Pathol.* 157:435-48 (2000).

Nakagawa, N., et al., "Rank is the essential signaling receptor for osteoclast differentiation factor in osteoclastogenesis." *Biochem. Biophys. Res. Commun.* 253:395-400 (1998).

O'Brien, E.A., et al., "Osteoprotegrin ligand regulates osteoclast adherence to the bone surface in mouse calvaria." *Biochem. Biophys. Res. Commun.* 274:281-90 (2000).

Oyajobi et al., "Therapeutic efficacy of a soluble receptor activator of nuclear factor kappa-B-IgG Fc Fusion Protein in suppressing bone resorption and hypercalcemia in a model of humoral hypercalcemia of malignancy", *Cancer Res.*, vol. 61:2572-78 (Mar. 15, 2001).

Peterson et al., "AMG162, A Fully Human Monoclonal Antibody Against Receptor Activator of NF-Kappa B Ligand (RANKL), Rapidly and Profoundly Suppresses Bone Resorption in Cynomolgus Monkey", International Bone and Material Society-Japan Bone and Mineral Society, 2003, Poster Session 2 "Osteoclasts", Osaka, Japan (Jun. 6, 2003).

Shalhoub, V., et al., "Osteoprotegrin and osteoprotegrin ligand effects on osteoclast formation from human peripheral blood mononuclear cell precursors." *J. Cell Biochem.* 72:251-61 (1999).

Suda, T., et al., "Modulation of osteoclast differentiation and function by the new members of the tumor necrosis factor receptor and ligand families." *Endocr. Rev.* 20:345-57 (1999).

Takahashi, N., et al., "A new member of tumor necrosis factor ligand family, ODF/OPGL/TRANCE/RANKL, regulates osteoclast differentiation and function." *Biochem Biophys. Res. Commun.* 256:449-55 (1999).

Takeyama, S., et al., "Low calcium environment effects osteoprotegrin ligand/osteoclast differentiation factor." *Biochim. Biophys. Res. Commun.* 276:524-9 (2000).

Teng, Y.A., et al., "Functional human T-cell immunity and osteoprotegrin ligand control alveolar bone destruction in periodontal infection." *J. Clin. Invest.* 106:749-52 (2000).

Udagawa, N., et al., "Osteoblasts/stromal cells stimulate osteoclast activation through expression of osteoclast differentiation factor/RANKL but not macrophage colony-stimulating factor." *Bone* 25:517-23 (1999).

Willard, D., et al., "Expression, purification, and characterization of the human receptor activator of NF-kappaB ligand (RANKL) extracellular domain." *Protein Expr. Purif.* 20:48-57 (2000).

Wong et al., "Trance (Tumor Necrosis Factor [TNF]-related Activation-induced Cytokine), a New TNF Family Member Predominantly Expressed in T cells, Is a Dendritic Cell-Specific Survival Factor", *J. Exp. Med.*, 186:2075-80 (1997).

Yasuda et al., "Osteoclast differentiation factor is a ligand for osteoprotegrin/osteoclastogenesis-inhibitory factor and is identical to Trance/RANKL." *Proc. Natl. Acad. Sci. USA*, 95:3597-3602 (Mar. 1998).

Zhang et al., "Tumor necrosis factor-alpha (TNF) stimulates RANKL-induced osteoclastogenesis via coupling of TNF type I receptor and Rank signaling pathways." *J. Biol. Chem.*, vol. 276(1):563-68 (Jan. 5, 2001).

Adams et al., "Complementary DNA Sequencing: Expressed Sequence Tags and Human Genome Project", *Science*, 252: 1651-1656 (1991).

Anderson et al., "A homologue of the TNF receptor and its ligand enhance T-cell growth and dendritic-cell function", *Nature*, 390: 175-179 (1997).

Chambers et al., "Generation of osteoclast-inductive and osteoclastogenic cell lines from the H-2KbtsA58 transgenic mouse", *Proceedings of the National Academy of Sciences of USA*, 90:5578-5582 (1993).

Fawthrop et al. "The Effect of Transforming Growth Factor β on the Plasminogen Activator Activity of Normal Human Osteoblask-like Cells and a Human Osteosarcoma Cell Line MG-63", *Journal of Bone and Mineral Research*, 7(12):1363-1371 (1992).

Fenton et al. "Long-Term Culture of Disaggregated Rat Osteoclasts: Inhibition of Bone Resorption and Reduction of Osteoclast-like Cell Number by Calcitonin and PTHrP[107-139]", *Journal of Cellular Physiology*, 155:1-7 (1993).

George et al., "Current Methods in Sequence Comparison and Analysis", *Macromolecular Sequencing and Synthesis Selected Methods and Applications*, pp. 127-149 (1988).

Goodwin et al., "Molecular Cloning and Expression of the Type 1 and Type 2 Murine Receptors for Tumor Necrosis Factor", *Molecular and Cellular Biology*, 11(6):3020-3026 (1991).

Gowen et al., "Preferential Inhibition of Cytokine-Stimulated Bone Resorption by Recombinant Interferon Gamma", *Journal of Bone and Mineral Research*, 1(5):469-474 (1986).

Hattersley et al., "Human Macrophage Colony-Stimulating Factor Inhibits Bone Resorption by Osteclasts Disaggregated From Rat Bone", *Journal of Cellular Physiology*, 137:199-203 (1988).

International Search Report, International Application No. PCT/JP98/01728 (1998).

Kaji et al., "Insulin-Like Growth Factor-I Mediates Osteoclast-Like Cell Formation Stimulated by Parathyroid Hormone", *Journal of Cellular Physiology*, 172:55-62 (1997).

Kasono et al., "Inhibitory Effect of Interleukin-4 on Osteoclast-Like Cell Formation in Mouse Bone Marrow Culture", *Bone and Mineral*, 21(3):179-188 (1993).

Kukita et al., "Osteoinductive Factor Inhibits Formation of Human Osteoclast-Like Cells", *Proceedings of the National Academy of Sciences of USA*, 87:3023-3026 (1990).

Lewis et al., "Cloning and Expression of cDNAs for Two Distinct Murine Tumor Necrosis Factor Receptors Demonstrate One Receptor is Species Specific", *Proceedings of the National Academy of Sciences of USA*, 88:2830-2834 (1991).

Reddi, A. H. "Bone Morphogenesis and Modeling: Soluble Signals Sculpt Osteosomes in the Solid State", *Cell*, 89:159-161 (1997).

Rieger et al., Glossary of Genetics and Cytogenetics, p. 17, Springer-Verlag Berlin Heidlberg, New York (1976).

Simonet et al., "Osteoprotegrin: A Novel Secreted Protein Involved in the Regulation of Bone Density", *Cell*, 89:309-319 (1997).

Smith et al., "The TNF Receptor Superfamily of Cellular and Viral Proteins: Activation, Costimulation, and Death", *Cell*, 76:959-962 (1994).

Suda et al., "Modulation of Osteoclast Differentiation by Local Factors", *Bone*, 17(2 Suppl): 87S-91S (1995).

Takada et al., "A Simple Method to Assess Osteoclast-Mediated Bone Resorption Using Unfractionated Bone Cells", *Bone and Mineral*, 17:347-359 (1992).

Tsuda et al., "Isolation of a Novel Cytokine From Human Fibroblasts That Specifically Inhibits Osteoclastogenesis", *Biochemical and Biophysical Research Communications*, 234(1):137-142 (1997).

Watanabe et al., "Interleukin-4 as a Potent Inhibitor of Bone Resorption" *Biochemical and Biophysical Research Communications*, 172(3):1035-1041 (1990).

Wong et al., "Trance is a Novel Ligand of the Tumor Necrosis Factor Receptor Family That Activates c-Jun N-terminal Kinase in T Cells", *Journal of Biological Chemistry*, 272(40):25190-25194 (1997).

Yoneda et al., "Suramin Suppresses Hypercalcemia and Osteoclastic Bone Resorption in Nude Mice Bearing a Human Squamous Cancer", *Cancer Research*, 55:1989-1993 (1995).

Chenu, C., et al., "Transforming growth factor β inhibits formation of osteoclast-like cells in long-term human marrow cells", *Proceed. of the National Academy of Sciences of USA*, vol. 85, pp. 5683-5687 (1998).

George et al., "Macromolecular Sequencing and Synthesis," edited by David Schlesinger, Alan R. Loss Inc., New York, pp. 127-149 (1988).

\* cited by examiner

F I G. 11
F I G. 12
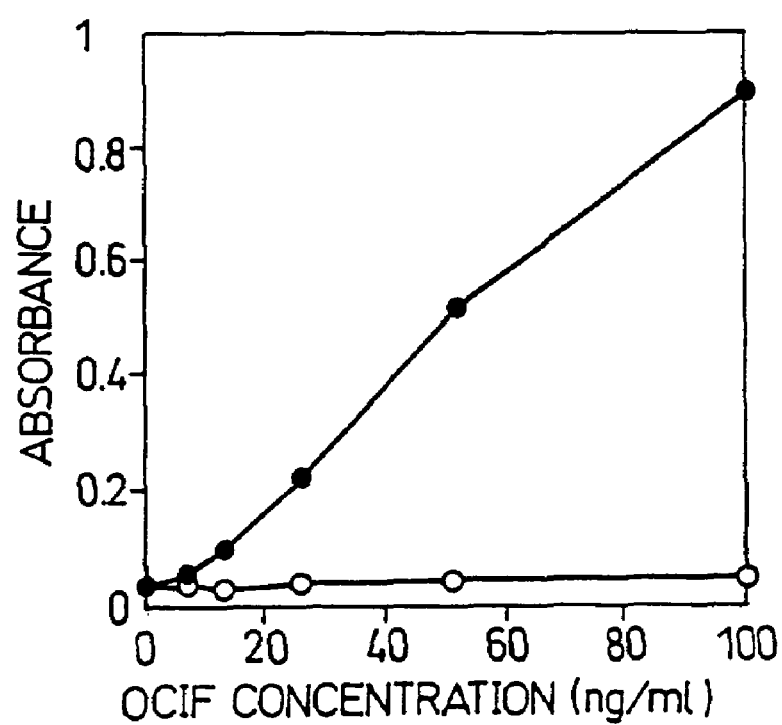

ANTIBODIES TO OCIF-BINDING MOLECULES

CROSS-REFERENCE TO RELATED APPLICATIONS

This application is a continuation of U.S. application Ser. No. 10/167,182, filed Jun. 11, 2002, which is a divisional of U.S. application Ser. No. 09/202,455, filed Dec. 15, 1998 (now abandoned), which is a national phase application under 35 U.S.C. § 371 of International Application No. PCT/JP98/01728, filed Apr. 15, 1998, which claims priority to Japanese Patent Application No. 097808/1997, filed Apr. 15, 1997, Japanese Patent Application No. 151434/1997, filed Jun. 9, 1997, Japanese Patent Application No. 217897/1997, filed Aug. 12, 1997, Japanese Patent Application No. 224803/1997, filed Aug. 21, 1997 and Japanese Patent Application No. 332241/1997, filed Dec. 2, 1997.

FIELD OF TECHNOLOGY

The present invention relates to a novel protein (OCIF-binding molecule, the protein may be hereinafter called OBM) which binds to osteoclastogenesis inhibitory factor (hereinafter it may be called OCIF) and a method to produce this protein.

The present invention also relates to DNA encoding this protein, proteins containing the amino acid sequence encoded by this DNA, a method for the preparation of this protein utilizing genetic engineering techniques, and pharmaceutical compositions comprising this protein.

The present invention further relates to methods for screening, using this protein and the DNA, substances to control the expression of this protein, substances inhibiting or regulating the biological activity of this protein, or receptors transducing the signal of the protein by interacting with this protein, to substances obtained by the screening, and to pharmaceutical compositions which comprise the resulting substances.

The present invention further relates to antibodies against this protein, methods for preparing the antibodies, and pharmaceutical compositions comprising these antibodies.

BACKGROUND OF THE INVENTION

Bone metabolism is dependent on the overall activity of osteoblasts which control bone formation and osteoclasts which control bone resorption. Abnormality of bone metabolism is considered to be caused by an imbalance of the bone formation and the bone resorption. Osteoporosis, hypercalcemia, Paget's disease, renal osteodystrophy, chronic rheumarthritis, osteoarthristis, and the like are known as diseases accompanying abnormality of bone metabolism. Osteoporosis is a typical disease caused by such abnormality of bone metabolism. This disease is generated when bone resorption by osteoclasts exceeds bone formation by osteoblasts. The disease is characterized by a decrease in both the bone calcified material and the bone matrix. Although the mechanism of this disease is not completely elucidated, the disease causes aches in bones, makes them fragile, and may result in fracturing. This disease is becoming a social problem because it increases the number of bedridden aged persons as the aged population becomes larger. Development of therapeutic agent for this disease is urgently desired. Disease due to a decrease in bone mass is expected to be cured by suppressing bone resorption, accelerating bone formation, or improving the balance between bone resorption and formation. Bone formation is expected to increase by accelerating proliferation, differentiation, or activation of osteoblasts which form bone, or by suppressing proliferation, differentiation, or activation of osteoclasts which resorb bone. In recent years, strong interest has been directed to hormones, low molecular weight substances, or physiologically active proteins exhibiting such activities, and energetic basic research and development is underway on these subjects.

Drugs such as a calcitonin agents, active-form vitamin $D_3$ agents, hormone agents containing estradiol, ipriflavon, vitamin $K_2$, and bisphosphonate compounds have already been known as drugs to treat and shorten the treatment period of diseases related to bone. Clinical tests are in progress on active-form vitamin $D_3$ derivatives, estradiol derivatives, and bisphosphonate compounds of the second and the third generation to develop therapeutic agents with excellent efficacy and minimal side effects.

However, therapies using these agents were found not necessarily satisfactory in terms of efficacy and therapeutic results. Development of novel therapeutic agents which are safer and with higher efficacy is urgently desired. Some agents used for the treatment of diseases related to bone metabolism are used only limitedly due to their side effects. Furthermore, treatments using two or more agents in combination are currently the mainstream in the treatment of diseases related to bone metabolism such as osteoporosis. From such a point of view, development of drugs having action mechanisms different from those of conventional drugs, and exhibiting a higher efficacy and minimal side effects is desired.

As mentioned above, the cells controlling bone metabolism are osteoblasts and osteoclasts. These cells are known to have close mutual interactions called "coupling". Specifically, cytokines such as Interleukins 1(IL-1), 3(IL-3), 6(IL-6), and 11(IL-11), granulocytic macrophage-colony stimulating factor (GM-CSF), macrophage-colony stimulating factor (M-CSF), Interferon-γ (IFN-γ), tumor necrosis factor a (TNF-α), and transforming growth factor-β (TGF-β), secreted by osteoblastic stromal cells are known to accelerate or suppress differentiation or maturation of osteoclasts (Raisz: Disorders of Bone and Mineral Metabolism, 287-311, 1992; Suda et al.: Principles of Bone Biology, 87-102, 1996; Suda et al.: Endocrine Reviews, 4, 266-270, 1995, Lacey et al.: Endocrinology, 186, 2369-2376, 1995). It has been reported that osteoblastic stromal cells play an important role in the differentiation and maturation of osteoclasts, as well as in osteoclast functions such as bone resorption by mature osteoclasts, through cell-to-cell contact with immature osteoclast precursors or mature osteoclasts.

A factor called osteoclast differentiation factor (ODF, Suda et al.: Endocrine Rev. 13, 66-80, 1992; Suda et al.: Bone 17, 87S-91S, 1995) is thought to be expressed on the membrane of osteoblastic stromal cells and involved in the formation of osteoclasts through cell-to-cell contact. According to this hypothesis, an ODF receptor is present in the precursor cells of osteoclasts. However, so far neither the ODF nor the receptor has been purified or identified. There are also no reports relating to their characteristics, action mechanism, or structure. Thus, the mechanism involved in differentiation and maturation of osteoclasts has not yet been sufficiently elucidated. Clarification of this mechanism will greatly contribute not only to the basic medicine, but also to the development of novel drugs for the treatment of diseases associated with abnormality of bone metabolism.

The present inventors have conducted extensive studies in view of this situation and discovered an osteoclastogenesis inhibitory factor (OCIF) in a culture broth of human embryonic lung fibroblast, IMR-90 (ATCC Deposition No. CCL186) (WO 96/26217).

The present inventors have been successful in cloning DNA encoding OCIF, production of recombinant OCIF in animal cells, and confirmation of in vivo pharmaceutical effects (improving effect on bone metabolism, etc.) of the recombinant OCIF. OCIF is expected to be used as an agent for the prevention or treatment of diseases related to abnormality of bone metabolism, with higher efficacy than conventional drugs and less side effects.

DISCLOSURE OF THE INVENTION

The present inventors have searched for a protein which binds to osteoclastogenesis inhibitory factor (OCIF) and discovered that an OCIF-binding protein is specifically expressed on the osteoblastic stromal cells cultured in the presence of a bone resorption factor such as active-form vitamin $D_3$ and parathyroid hormone (PTH). In addition, the present inventors have investigated the characteristics and physiological functions of this OCIF-binding protein and found that the protein exhibits biological activity of a factor which supports or promotes the osteoclast differentiation and maturation from immature precursors of osteoclasts. These findings have led to the completion of the present invention. Further investigation into the protein of the present invention has proven that this is an important protein controlling the differentiation and maturation of osteoclasts from immature precursors of osteoclasts in a co-culture system of the osteoblastic stromal cells and spleen cells. The success in identification and isolation of the protein which functions as a factor supporting or promoting differentiation and maturation of osteoclasts in the present invention has enabled screening for a novel medicine useful for abnormality of bone metabolism based on mechanism of bone metabolism utilizing the protein of the present invention.

Accordingly, an object of the present invention is to provide a novel protein (OCIF-binding molecule or OBM) which binds to osteoclastogenesis inhibitory factor (OCIF), and a method to produce this protein.

Another object of the present invention is to provide DNA encoding this protein, proteins containing an amino acid sequence encoded by this DNA, a method for producing this protein utilizing genetic engineering techniques, and pharmaceutical compositions comprising this protein.

A further object of the present invention is to provide methods for screening substances which control expression of this protein using this protein and the DNA, substances inhibiting or regulating the biological activity of this protein, receptors transducing the action of the protein by binding to the protein, substances obtained by the screening, and pharmaceutical compositions which comprises these substances.

A still further object of the present invention is to provide antibodies against this protein, methods for preparing the antibodies, and pharmaceutical compositions comprising these antibodies.

The protein of the present invention has the following physicochemical properties and biological activity.
(a) Affinity: specifically binds to the osteoclastogenesis. inhibitory factor (OCIF) and exhibits high affinity to OCIF (dissociation constant on cell membrane: $Kd=10^{-9}$ M or less);
(b) Molecular weight: has a molecular weight of approximately 30,000-40,000 when determined by SDS-polyacrylamide gel electrophoresis (SDS-PAGE) under non-reducing conditions and an apparent molecular weight of approximately 90,000-110,000 when cross-linked to a monomer form OCIF; and
(c) Biological activity: exhibits activity supporting or promoting osteoclast differentiation and maturation in a co-culture system of the mouse osteoblastic stromal cells and mouse spleen cells in the presence of bone resorption factors such as active-form vitamin $D_3$ and parathyroid hormone (PTH).

A co-culture system of ST2, a mouse osteoblastic stromal cell line, and mouse spleen cells in the presence of active-form vitamin $D_3$ or PTH is well known as a typical in vitro culture system for osteoclast formation. The cells expressing the protein of the present invention can be determined by testing the binding of OCIF to mouse osteoblastic stromal cells or mouse spleen cells cultured in the presence or absence of active-form vitamin $D_3$. The protein of the present invention is specified as the protein which is induced specifically on the osteoblastic stromal cells cultured in the presence of an osteotropic factor such as active-form vitamin $D_3$ or PTH. In addition, the protein of the invention can be specified as a protein exhibiting biological activity supporting or promoting differentiation and maturation of osteoclasts from the following results. That is, the osteoclast formation is inhibited dose dependently by the addition of 1 to 40 ng/ml of OCIF to the above-mentioned co-culture system in the presence of the active-form vitamin $D_3$, the time course of expression of the protein of the present invention on ST2 cells in the presence of active-form vitamin $D_3$ well correlates with the time course of osteoclast formation in the co-culture. In addition, the amount of protein of the present invention expressed on ST2 cells correlates with the capability of the cells to support the osteoclast formation, and the binding of OCIF to the protein of the present invention on the ST2 cells completely suppresses osteoclasts formation.

The affinity of the protein of the present invention to OCIF can be evaluated by labeling OCIF and examining the binding of the labeled OCIF to the surface of animal cell membrane. OCIF can be labeled by a conventional protein-labeling method such as radioisotope or fluorescent labeling. Labeling of tyrosine residues with $^{125}I$ can be given as a specific example of labeling of the OCIF with an radioisotope. Labeling methods such as iodogen method, chloramine T method, and enzymatic method can be utilized. The binding of the labeled OCIF to the surface membrane of animal cell can be tested by a conventional method. The addition of unlabeled OCIF to the medium used for the binding assay to a concentration, 100 to 400 times the concentration of labeled OCIF, ensures measurement of non-specific binding. The amount of specific binding of OCIP can be calculated by subtracting the amount of non-specific binding from the total amount of binding of the labeled OCIF. The affinity of the protein of the present invention expressed on the cell membrane to OCIF can be evaluated by changing the amount of labeled OCIF and analyzing the specific binding by Scatchard plot.

The determined affinity of the protein of the present invention to OCIF is approximately 100-500 pM. The protein of the present invention is specified by a high affinity (dissociation constant on cell membrane: $Kd=10^{-9}$ M or less) to osteoclastogenesis inhibitory factor (OCIF). The molecular weight of OBM can be accessed by gel filtration chromatography, SDS-PAGE, or the like. SDS-PAGE is preferred in order to accurately determine the molecular weight. The OBM is specified as a protein having a molecular weight of approximately 40,000 (40,000±4,000) under reducing conditions.

The protein of the present invention can be obtained from mouse osteoblastic stromal cell line, ST2, mouse preadipocyte cell line, PA6, human osteoblastic cell lines, or other osteoblastic cells selected from mammalians such as humans, mice, or rats. As the substances to induce expression of the protein of the present invention, osteotropic factors such as active-form vitamin $D_3$ (calcitriol), parathyroid hormone (PTH), interleukin (IL)-1, IL-6, IL-11, Oncostatin M, and leukemia inhibitory factor (LIF) can be given. These substances can be added in the concentration of $10^{-8}$ M (active-form vitamin $D_3$ and PTH), 10 ng/ml (IL-11), or 1 ng/ml (Oncostatin M). IL-6 is preferably used at a concentration of 20 ng/ml with 500 ng/ml soluble IL-6 receptor. Preferably, confluent cells of mouse osteoblastic stromal cell line, ST2, cultured in α-MEM medium to which $10^{-8}$ M of active-form vitamin $D_3$, $10^{-7}$ M of dexamethasone, and 10% fetal bovine serum were added canbeused. The cultured cells may be collected by scraping with a cell scraper. The collected cells may be stored at −80° C. until use.

The protein of the present invention can be purified efficiently from the membrane fractions of the collected cells. The membrane fractions can be prepared by a conventional method which is used to prepare intracellular organella. Various types of protease inhibitors may be added to the buffer solution used for the preparation of the membrane fractions. Examples of the protease inhibitors include serine protease inhibitors, thiol protease inhibitors, and metaprotease inhibitors. PMSF, APMSF, EDTA, o-phenanthroline, leupeptine, pepstatin A, aprotinin, soybean trypsin inhibitor are givens as specific examples. A Daunce homogenizer, a polytron homogenizer, or a ultrasonic processor can be used to homogenize the cells. The cell homogenate is suspended in a buffer solution containing 0.5 M of sucrose and centrifuged for 10 minutes at 600×g, to separate the nucleus and undisrupted cells as precipitate. The supernatant is centrifuged for 90 minutes at 150,000×g to obtain a membrane fractions as precipitate. The obtained membrane fraction is treated by various types of detergents to efficiently solubilize and extract the protein of the present invention from the cell membrane. Detergents which are commonly used to solubilize cell membrane proteins, such as CHAPS (3-[(3-cholamidopropyl)-dimethylamonio]-1-propanesulfonate), TritonX-100, Nikkol, and n-octylglycoside, can be used. Preferably, 0.5% CHAPS is added to the membrane fraction and the mixture is stirred for 2 hours at 4° C. to solubilize the protein of the present invention. The sample thus prepared is centrifuged at 150,000×g for 60 minutes to obtain the solubilized membrane fraction as a supernatant.

The protein of the present invention can be purified from the solubilized membrane fraction with a column, gel, or resin coupled with OCIF. The immobilized OCIF may be that isolated from a culture broth of human embryonic lung fibroblasts, IMR-90, described in WO 96/26217 or rOCIF prepared using genetic engineering techniques. rOCIF can be prepared by introducing human cDNA, mouse cDNA, or rat cDNA into an expression vector according to a conventional method, transducing the constructed vector in animal cells such as CHO cells, BHK cells, or Namalwa cells, or in insect cells to produce rOCIF, and purifying rOCIF. Obtained OCIF has a molecular weight of approximately 60 kDa (monomer-form) or 120 kDa (dimer-form). The dimer-form OCIF is preferable for immobilization. Given as examples of the gels and resins to which OCIF is immobilized are ECH Sepharose 4B, EAH Sepharose 4B, Thiopropyl Sepharose 6B, CNBr-activated Sepharose 4B, activated CH Sepharose 4B, Epoxy activated Sepharose 6B, activated thiol Sepharose 4B (these are manufactured by Pharmacia Co.), TSKgel AF-Epoxy Toyopal 650, TSKgel AF-Amino Toyopal 650, TSKgel AF-Formyl Toyopal 650, TSKgel AF-Carboxy Toyopal 650, TSKgel AF-Tresyl Toyopal650 (these are manufactured by Tosoh Corporation), Amino-Cellulofine, Carboxy-Cellulofine, FMP activated Cellulofine, Formyl-Cellulofine (these are manufactured by Seikagaku Kogyo Co.), Affigel 10, Affigel 15, and Affiprep 10 (these are manufactured by BioRad Co.). As columns to which OCIF is immobilized, HiTrap NHS-activated column (Pharmacia Co.), TSKgel Tresyl-5PW (Tosoh Corporation), etc. can be given. As a specific example of the method for immobilizing OCIF to a HiTrap NHS-activated column (1 ml, Pharmacia Co.), the following method can be given. Specifically, 1 ml of 0.2M $NaHCO_3$/0.5 M NaCl solution (pH 8.3) containing 13.0 mg of OCIF is injected to the column to perform coupling reaction at room temperature for 30 minutes. 0.5 M ethanolamine/0.5 M NaCl (pH 8.3) and 0.1 M acetic acid/0.5 M NaCl (pH 4.0) are sequentially applied to the column. Then, the column is again washed with 0.5 M ethanolamine/0.5 M NaCl (pH 8.3) and the column is allowed to stand for one hour at room temperature to block excess active groups. The column is sequentially washed twice with 0.5 M ethanolamine/0.5 M NaCl (pH 8.3) and 0.1 M acetic acid/0.5 M NaCl (pH 4.0), and then washed with 50 mM Tris/1 M NaCl/0.1% CHAPS solution (pH 7.5), thereby obtaining a OCIF-immobilized column. The protein of the present invention can be efficiently purified by a OCIF-immobilized column prepared in this manner, or an OCIF-immobilized gel or resin.

It is desirable to add the various above-mentioned protease inhibitors to the buffer solutions used for the purification of the protein to suppress degradation of the protein of the present invention. The protein of the present invention can be purified by loading the above-mentioned solubilized membrane fraction on the OCIF-immobilized column or by mixing with the OCIF-immobilized gel or resin, and eluting the protein from the column, gel, or resin with acid, various protein denaturing agents, cacodylate buffer, and the like. It is desirable to use an acid for elution and to neutralize immediately after elution to minimize denaturation of the protein of the present invention. As the acidic solution used for elution, 0.1 M glycine-hydrochloric acid solution (pH 3.0), 0.1 M glycine-hydrochloric acid solution (pH 2.0), 0.1 M sodium citrate solution (pH 2.0), and the like can be given.

The protein of the present invention can be further purified by conventional purification methods used for purification of various proteins from biological materials and by various purification methods utilizing the physicochemical properties of this protein. To concentrate solutions containing the protein of the present invention, conventional techniques used in the purification process for proteins such as ultra filtration, freeze drying, and salting-out, can be used. Ultra filtration with Centricon-10 (BioRad Co.), for example, is preferably used. As a means for the purification, various techniques conventionally utilized for the purification of proteins, such as ion exchange chromatography, gel filtration chromatography, hydrophobic chromatography, reverse phase chromatography, and preparative electrophoresis, are used in combination. More specifically, it is possible to purify the protein of the present invention by a combination of gel filtration chromatography with Superose 12 column (Pharmacia Co.) and reverse phase chromatography. To detect the protein of the present invention in the purification process, the binding activity of the protein of the present invention to the immobilized OCIF is examined or the material bound to the immobilized OCIF is immuno precipitated with an anti-OCIF antibody and analyzed by SDS-polyacrylamide gel electrophoresis (SDS-PAGE).

The obtained protein of the present invention is useful as an agent for treating diseases caused by abnormality of bone metabolism such as osteopetrosis or as a reagent for research and diagnosis of these diseases.

The present invention further provides DNA encoding a novel protein (OCIF-binding molecule or OBM) which binds to osteoclastogenesis inhibitory factor, proteins containing the amino acid sequence encoded by this DNA, a method for the preparation of this protein by the genetic engineering technique, and pharmaceutical compositions comprising this protein. Furthermore, the present invention provides methods for screening substances to regulate expression of OBM, a method for screening substances inhibiting or modifying the biological activity of OBM, or a method for screening receptors transducing the action of OBM by binding to OBM, and pharmaceutical compositions which comprises substances obtained as a result of the screening.

The novel protein OBM which is encoded by the DNA of the present invention has the following physicochemical properties and biological activity.
(a) binds specifically to osteoclastogenesis inhibitory factor (OCIF),
(b) has a molecular weight of approximately 40,000 (±4,000) when determined by SDS-PAGE under reducing conditions and an apparent molecular weight of approximately 90,000-110,000 when crosslinked to monomer-form OCIF, and
(c) exhibits activity supporting or promoting differentiation and maturation of osteoclasts.

Human osteoclastogenesis inhibitory factor (OCIF) which is used as a probe to identify the DNA encoding OBM, the OCIF-binding molecule of the present invention, and to evaluate properties of OBM can be isolated from a culture broth of a human embryonic lung fibroblast cell line, IMR-90, according to WO No. 96/26217. Recombinant human OCIF, recombinant mouse OCIF, recombinant rat OCIF, and the like can also be used for the isolation and identification of the DNA coding OBM. These recombinant OCIF proteins can be produced by inserting DNA fragments encoding these proteins into expression vectors according to conventional methods, expressing in animal cells such as CHO cells, BHK cells, or Namalwa cells, or in insect cells, and purifying them.

As a method for isolating cDNA encoding a target protein (cDNA cloning), the method comprising determination of a partial amino acid sequence of the protein and isolation of the target cDNA by hybridization utilizing the nucleotide sequence corresponding to the amino acid sequence can be employed. Another available method, even in the case where the amino acid sequence of the protein is not known, comprises constructing a cDNA library in a expression vector, introducing the cDNA into cells, and screening for the expression of the target protein to isolate the objective cDNA (expression cloning method, D'Andrea et al.: Cell 57, 277-285, 1989; Fukunaga et al.: Cell 61,341-350, 1990). In the expression cloning method, suitable host cells such as bacteria, yeast, animal cells, and the like are selected depending on the objective. In many cases, animal cells are selected as the host cells for cloning cDNA encoding a protein such as the protein of the present invention which is considered to be present in animal cell membrane surface. Normally, host cells showing high efficiency for DNA transfection and achieving expression of the introduced DNA at high levels are selected. One of such animal cells is the monkey kidney cells, COS-7, used in the present invention. Because SV40 large T antigen is expressed in the COS-7 cell, a plasmid which has a replicator of SV40 can be present as an episome of multiple copies in the cell, so that a high level of expression is expected. In addition, because expression of a target protein by COS-7 cells reaches a maximum within a few days after introduction of DNA, the cell is suitable for rapid screening. A combination of this host cell with a plasmid capable of high expression ensures gene expression of an extremely high level. The factor exhibiting the greatest influence on the expression of a gene on a plasmid is a promoter. Promoters such as SRα promoter and cytomegalovirus-derived promoters are used as high expression promoters. To screen for the cDNA encoding a membrane protein by the expression cloning strategy, screening procedures such as binding method, panning method, or film emulsion method are used.

The present invention relates to DNA encoding the protein (OBM) which specifically binds to OCIF, isolated by the combination of the expression cloning strategy and the screening by the binding method, to the expressed protein, and to screening of physiologically active substances using the DNA or the expressed protein. OBM encoded by the DNA of the present invention can be detected by labeling OCIF and testing the binding of the labeled OCIF to membrane surface of an animal cell. OCIF can be labeled by a conventional labeling method such as radioisotope labeling method or fluorescent labeling method which is used for labeling common proteins. Labeling tyrosine residues by $^{125}I$ can be given as a specific example of labeling OCIF with a radioisotope. Labeling methods such as the iodogene method, chloramine T method, and enzymatic method can be utilized. The binding of labeled OCIF to the animal cell membrane surface can be tested by conventional methods. The addition of unlabeled OCIF to the medium used for the test to a concentration, 100 to 400 times the concentration of labeled OCIF, enables quantification of the amount of non-specific binding. The amount of specific binding of OCIF can be calculated by subtracting the amount of non-specific binding from the total amount of binding of the labeled OCIF.

The present inventors assumed that there is interaction between the factor involved in differentiation of osteoclasts and OCIF. Based on this assumption, to isolate the protein to which recombinant OCIF binds, the inventors screened the expression library prepared from mRNA of mouse osteoblastic stromal cell line, ST2, according to the following method. Specifically, DNA synthesized using ST2 mRNA was inserted into an expression vector for animal cells and the vector with the insert was introduced into monkey kidney COS-7 cells. The objective protein expressed on the COS-7 cells was screened using OCIF labeled with $^{125}I$ as a probe. As a result, DNA encoding the protein which binds specifically to OCIF was isolated. The nucleotide sequence of the DNA encoding this OCIF-binding molecule (OCIF-binding molecule; OBM) was then determined. Moreover, OBM encoded by this DNA was found to bind specifically and strongly to OCIF, on the cell membrane.

Comparatively mild conditions for hybridization of DNA in the present invention are the conditions, for example, wherein DNA is transferred to a nylon membrane and immobilized thereto according to conventional methods and hybridized in a buffer solution for hybridization with a probe DNA labeled with an isotope at a temperature of 40-70° C. for about 2 hours to overnight, followed by washing in 0.5×SSC (0.075 M sodium chloride and 0.0075 M sodium citrate)at 45° C. for 10 minutes. Specifically, Highbond N (Amersham Co.) is used as the nylon membrane to transfer and immobilize DNA thereon. DNA is then hybridized with a probe DNA labeled with $^{32}P$ in a rapid hybridization buffer (Amersham Co.) at 65° C. for 2 hours, followed by washing with 0.5×SSC (0.075 M sodium chloride and 0.0075 M sodium citrate) at 45° C. for 10 minutes.

A co-culture system of mouse osteoblastic stromal cells, ST2, and mouse spleen cells in the presence of active-form vitamin $D_3$ or PTH is well known as a typical in vitro culture system for osteoclast-formation. The protein of the present invention is specified as the protein which is induced specifically on the osteoblastic stromal cells cultured in the presence of an agent which accelerates bone resorption such as active-form vitamin $D_3$ or PTH. In addition, because of the fact that formation of osteoclasts is stimulated by the addition of the protein encoded by the DNA of the present invention to mouse spleen cells cultured even in the absence of active-form vitamin $D_3$ or PTH, OBM which is encoded by the DNA of the present invention is considered to be involved in the differentiation and maturation of osteoclasts.

Recombinant OBM can be produced by inserting the DNA of the present invention into an expression vector to construct a plasmid and introducing the plasmid into various cells or microorganisms to express recombinant OBM. As a host in which recombinant OBM is expressed, mammalianian cells such as COS-7, CHO, Namalwa, or bacteria such as *Escherichia coli* can be used. OBM may be expressed as a membrane-bound-form protein using the full length DNA or as a secretion-form or a soluble-form protein by removing the portion encoding the transmembrane domain. The produced recombinant OBM can be efficiently purified using a suitable combination of conventional purification methods used for common proteins, such as affinity chromatography using OCIF-immobilized columns, ion exchange chromatography, and gel filtration chromatography. The obtained protein of the present invention is useful as an agent for treating diseases caused by abnormality of bone metabolism such as osteopetrosis or as a reagent for research and diagnosis of such diseases.

The following screening operations can be carried out using the protein OBM encoded by the DNA of the present invention: (1) screening of substances which regulate expression of OBM, (2) screening of substances which specifically bind to OBM and inhibit the biological activity of OBM, and (3) screening of proteins which are present in osteoclast precursor cells and transduce the biological activity of OBM (OBM receptor). It is also possible to develop antagonists and agonists using this OBM receptor. In the combinatorial chemistry using the above-mentioned OBM or OBM receptor, a peptide library used for the screening of the antagonists or agonists can be prepared by the following method. Specifically, one of the methods is split method (Lam et al.; Nature 354, 82-84, 1991). According to this method, synthetic carriers (beads) each comprising a specific amino acid (unit) bound thereto are prepared separately for all units. The synthesized carriers are mixed altogether and divided into portions equal to the number of the units. Then, the next units are bound. This procedure is repeated "n" times to produce a library containing carriers to which "n" units are bound. According to this synthetic method, each carrier pool has one type of sequence. Therefore, it is possible to identify a peptide specifically binding to the protein of the present invention by selecting the pool which gives a signal positive in this screening method using the protein of the present invention, and determining the amino acid sequence of the peptide bound on the pool. Another method is phage display method which utilizes phage carrying synthetic DNA which encode peptides with random amino acid sequences. The method has the advantage of increasing the number of molecules in the library as compared with the above-mentioned synthetic peptide library method, but has the disadvantage of less variety for a given number of molecules because there can be particular sequences which are missing in the library if the phages are unable to express those sequences. In the phage display method, the screening system using the protein of the present invention can also be applied to determine the nucleotide sequence encoding the peptide. That is, the phage specifically binding to the protein of the present invention is concentrated by panning, the selected phage is amplified in *Escherichia coli*, and the nucleotide sequence encoding the peptide is determined. In addition, a peptide exhibiting high specificity and high affinity to OBM or OBM receptor can be screened from a peptide library using the screening systems mentioned above in (2) and (3) by screening in the presence of OBM or OCIF while increasing the concentration of OBM or OCIF. Only positive carrier pools or phages are selected in this manner. For example, low molecular weight peptide agonists exhibiting an EPO (erythropoietin)-like activity were screened from a peptide library using a receptor of erythropoietin (EPO) which is a hematopoietic hormone, the tertiary structure of this substance was analyzed, and based on this tertiary structure, low molecular weight substances (antagonist) exhibiting the EPO-like activity were synthesized (Nicholas et al.: Science, 273, 458-463, 1996).

The present inventors have previously discovered using the osteoclastogenesis inhibitory factor, OCIF, that an OCIF-binding protein is specifically expressed on osteoblastic stromal cell line, ST2, cultured in the presence of a osteotropic factor such as active-form vitamin $D_3$ or parathyroid hormone (PTH). The inventors further found that this protein exhibits a biological activity to support or stimulate differentiation or maturation of osteoclasts from immature osteoclast precursor cells, and clarified various physicochemical properties and the biological activity of this protein by purification thereof. In order to compare the recombinant OBM expressed by the DNA of the present invention and the above-mentioned purified natural type protein which specifically binds to OCIF, the present inventors investigated the physicochemical properties and biological activities of the two proteins. As a result, the two proteins were confirmed ① to be both membrane-bound proteins which specifically bind to OCIF, ② to have molecular weights of approximately 40,000 determined by SDS-PAGE, and ③ to have apparent molecular weights of about 90,000-110,000 when cross-linked to a monomer form OCIF. Not only are these physicochemical properties identical, but both proteins exhibit a biological activity to support or stimulate differentiation or maturation of osteoclasts, suggesting the possibility that these are the same protein. In addition, a rabbit anti-OBM polyclonal antibody produced using the purified protein prepared by expressing the DNA of the present invention by a genetic engineering technique (recombinant OBM) was confirmed to cross react with the above-described purified natural type protein, to inhibit specific binding of this purified natural type protein and OCIF in the same manner as the antibody inhibits specific binding of OBM and OCIF. Based on these results, it is clear that the recombinant OBM expressed by the DNA of the present invention is identical to the natural type protein which specifically binds to OCIF.

To isolate a gene (cDNA) encoding human OCIF-binding protein (hereinafter called human OBM) which specifically binds to OCIF and exhibits the activity to support and stimulate differentiation and maturation of osteoclasts from mouse spleen cells in the same manner as the natural type or recombinant mouse OBM dose, a cDNA library prepared from mRNA derived from human lymph nodes was screened using a human OBM cDNA fragment as a probe. The human OBM cDNA fragment was obtained by polymerase chain reaction (PCR) in accordance with the method mentioned above using both cDNA prepared from human lymph node as a template and the primer which was prepared from mouse OBM cDNA. As a result, cDNA encoding the human protein which specifically binds to OCIF was isolated and the nucleotide sequence of the cDNA encoding this human OCIF-binding protein molecule (i.e. the cDNA encoding human OBM) was determined. Similar to mouse OBM, this human OBM encoded by the cDNA has characteristics to bind to OCIF strongly and specifically on the cell membrane and exhibits the activity to support and promote differentiation and maturation of osteoclasts from mouse spleen cells. Specifically, the present invention provides DNA encoding novel human OBM protein which binds to osteoclastogenesis inhibitory factor (OCIF), a protein which possesses the amino acid sequence encoded by the DNA, a method for producing the protein exhibiting characteristics of specifically binding to OCIF and the activity to support and promote differentiation and maturation of osteoclasts from mouse spleen cells by genetic engineering techniques, pharmaceutical compositions comprising this protein for the treatment of diseases caused by abnormality of bone metabolism, a method for screening substances regulating expression of human OBM, a method for screening substances which inhibit or modulate the activity of human OBM by binding to it, a method for screening receptors which bind to human OBM and transmit the action of OBM, and a pharmaceutical compositions comprising the substances obtained by these screenings.

The present invention further provides DNA encoding novel human OBM protein which specifically binds to OCIF and exhibits the biological activity to support and promote differentiation and maturation of osteoclasts, a protein which possesses the amino acid sequence encoded by the DNA, a method for producing the protein exhibiting characteristics of specifically binding to OCIF and the activity to support and promote differentiation and maturation of osteoclasts by genetic engineering techniques, and pharmaceutical compositions comprising this protein for the treatment of diseases causing abnormality of bone metabolism. Furthermore, the present invention provides a method for screening substances regulating expression of human OBM, a method for screening substances which inhibit or modulate the activity of human OBM by binding to it, a method for screening receptors binding to human OBM and transmitting the action of OBM, antibodies against human OCIF binding protein, and, pharmaceutical compositions comprising these antibodies for the prevention or treatment of diseases causing abnormality of bone metabolism.

The novel, human OCIF-binding protein molecule (OBM) which is encoded by the DNA of the present invention has the following physicochemical properties and biological activity.
(a) binds specifically to osteoclastogenesis inhibitory factor (OCIF) (WO 96/26217),
(b) has a molecular weight of approximately 40,000 (±5,000) when determined by SDS-PAGE under reducing conditions and an apparent molecular weight of approximately 90,000-110,000 when crosslinked with a monomer form OCIF, and
(c) exhibits activity to support and stimulate differentiation and maturation of osteoclasts.

Mouse OBM cDNA which encodes mouse OCIF-binding protein and used as a probe to isolate and identify the cDNA encoding human OBM of the present invention, can be isolated according to the above-mentioned method from a cDNA library of mouse osteoblastic stromal cell line, ST2. Human osteoclastogenesis inhibitory factor (OCIF) which is necessary to evaluate the properties and the biological activity of the protein obtained by expression of human OBM cDNA, can be prepared according to the method described in WO 96/26217 by isolating from a culture broth of human fibroblast cell line, IMR-90, or by genetic engineering techniques using the DNA encoding OCIF. Recombinant human OCIF, recombinant mouse OCIF, recombinant rat OCIF, or the like can be used for the assessment of the properties and biological activity of human OBM. These recombinant OCIF can be obtained according to conventional methods by inserting cDNA into an expression vector, expressing the cDNA in animal cells such as CHO cells, BHK cells, or Namalwa cells, or in insect cells, and purifying the expressed proteins.

The following methods can be used to isolate human cDNA encoding the target protein (cDNA cloning). ① A method comprising purifying the protein, determining the partial amino acid sequence of the protein, and isolating the target cDNA by hybridization using the DNA fragment comprising nucleotide sequence corresponding to the amino acid sequence as a probe, ② a method applied even in the case where the amino acid sequence of the protein is not known, which comprises constructing a cDNA library in a expression vector, introducing the cDNA library into cells, and screening for the expression of the target protein to isolate the objective cDNA (expression cloning method), and ③ a method of isolating cDNA encoding the target human protein from the cDNA library constructed using human cells or tissues by hybridization or by the use of polymerase chain reaction (PCR) using the cDNA encoding the protein of mammalian origin (other than human) which possesses the same characteristics and biological activity as the target protein of human origin as a probe, assuming that the cDNA probe has high homology with the human-origin cDNA which to be cloned. Based on the assumption that human OBM cDNA has a high homology with mouse OBM cDNA, it is possible to determine which cells or tissues produce human OBM by Northern hybridization method using the mouse OBM cDNA as a probe. Human OBM cDNA can be obtained by the following method using the mouse OBM primer prepared from the mouse OBM cDNA. Human OBM cDNA fragments can be prepared by the PCR method using cDNA prepared from human OBM-producing tissues such as human lymph nodes as a template. These human OBM cDNA fragments are used as probes for screening the cDNA library of human OBM-producing cells or tissues which were identified according to the method mentioned above. The present invention relates to the DNA encoding human OBM which has characteristics of specific binding to OCIF and exhibits activity to support and promote differentiation and maturation of osteoclasts. Because the OBM which is encoded by the DNA of the present invention is a membrane-bound type protein which comprises a transmembrane domain, this protein can be detected by labeling OCIF and by examining the binding of the labeled OCIF to the surface of animal cells in which the cDNA of the present invention was expressed. The above-described labeling method using radioisotope or fluoresceine conventionally applied to labeling proteins can be used for labeling OCIF.

The molecular weight of the protein expressed by the human OBM cDNA of the present invention can be accessed by gel filtration chromatography, SDS-PAGE, or the like. In order to accurately determine the molecular weight, it is desirable to use the SDS-PAGE method, by which human OBM was specified as a protein having a molecular weight of approximately 40,000 (40,000±5,000) under reducing conditions.

Comparatively mild conditions for hybridization of DNA in the present invention are the conditions, for example, wherein DNA is transferred to a nylon membrane and immobilized thereto according to a conventional method and hybridized with a probe DNA labeled with an isotope in a buffer solution for hybridization at a temperature of 40-70° C.

for about 2 hours to overnight, followed by washing in 0.5× SSC (0.075 M sodium chloride and 0.0075 M sodium citrate) at 45° C. for 10 minutes. Specifically, Highbond N (Amersham Co.) is used as the nylon membrane to transfer and immobilize DNA thereon. The DNA is then hybridized with a probe DNA labeled with $^{32}$P in a rapid hybridization buffer (Amersham Co.) at 65° C. for 2 hours, followed by washing with 0.5×SSC at 45° C. for 10 minutes.

A co-culture system of mouse osteoblastic stromal cells, ST2, and mouse spleen cells in the presence of active-form vitamin $D_3$ or PTH is well known as a typical in vitro culture system for osteoclast-formation. Interaction by adhesion of osteoblastic stromal cells and spleen cells and presence of an osteotropic factor such as active-form vitamin $D_3$ or PTH are indispensable for the osteoclasts formation in this in vitro culture system. In this in vitro culture system, COS cells, monkey kidney cells having no osteoclast formation-supporting capability, acquire capability to support osteoclasts formation from spleen cells in the absence of an osteotropic factor when the cDNA of the present invention was expressed as osteoblastic stromal cell line ST2 did. Based on the fact that the cDNA of the present invention encodes a protein comprising a transmembrane domain form, this cDNA can be expressed as a secretion form or soluble-form by removing the part which encodes this transmembrane domain. It was confirmed that osteoclasts can be formed by the addition of the secretion form human OBM to the above-mentioned in vitro culture system in the absence of osteotropic factors. Based on these results, the human OBM which is encoded by the cDNA of the present invention is specified as the factor involved in the differentiation and maturation of osteoclasts.

A recombinant human OBM can be prepared by inserting the cDNA of the present invention into an expression vector, preparing a human OBM expression plasmid, introducing the plasmid into various cell strains and expressing OBM in the cells. Mammalianian cells such as COS-7, CHO, Namalwa cells, or bacteria such as *Escherichia coli* can be used as a host for expressing OBM. In this case, OBM may be expressed as a membrane-bound-form protein, using the full length DNA, or as a secretion-form or soluble-form protein by removing the part encoding the transmembrane domain. The recombinant OBM thus produced can be efficiently purified using a suitable combination of conventional purification methods used for common proteins such as affinity chromatography using OCIF immobilized columns, ion exchange chromatography, and gel filtration chromatography. Human OBM of the present invention thus obtained is useful as an agent for treating diseases caused by abnormality of bone metabolism such as osteopetrosis or as a reagent for research and diagnosis of such diseases.

The following screening operations can be carried out using the protein OBM encoded by the DNA of the present invention: (1) screening of substances which can regulate expression of human OBM, (2) screening of substances which specifically bind to human OBM and inhibit or modify the biological activity of OBM, and (3) screening of human proteins which are present in osteoclast precursor cells and transmit the biological activity of human OBM (human OBM receptor). It is also possible to develop antagonists and agonists using this human OBM receptor. In the combinatorial chemistry using the human OBM or human OBM receptor, peptide libraries required for the screening of antagonists or agonists can be produced by the same method as used for the screening using mouse OBM. A peptide with extremely high specificity and affinity can be obtained by screening peptide libraries using human OBM instead of mouse OBM.

Although this OBM is very useful as mentioned above and antibodies specifically recognizing OBM and enzyme immunoassay using these antibodies are indispensable in determination of OBM concentration, no antibodies useful for the access of OBM concentration have been so far available. In addition, an anti-OBM antibody or anti-sOBM antibody which neutralizes the biological activity of OBM or sOBM is supposed to suppress the activity of OBM or sOBM, specifically the activity to induce osteoclasts formation. These are expected to be useful as therapeutic agents to treat abnormality of bone metabolism. However, no such antibodies have so far been available.

In view of this situation, the present inventors have conducted extensive studies. As a result, the present inventors have found antibodies (anti-OBM/sOBM antibodies) which recognize both OBM, a membrane-bound protein which specifically binds to osteoclastogenesis inhibitory factor (OCIF), and soluble OBM (sOBM) which lack a transmembrane domain. Accordingly, the present invention provides antibodies (anti-OBM/sOBM antibodies) which recognizes both OBM, a membrane-bound protein which specifically binds to osteoclastogenesis inhibitory factor (OCIF), and sOBM which lack a transmembrane domain; a method for the preparation thereof; a method for determination of OBM and sOBM concentrations using these antibodies; and agents for the prevention or treatment of diseases resulting from abnormality of bone metabolism.

The present invention relates to antibodies (anti-OBM/sOBM antibodies) which recognize both the OBM, a membrane-bound protein which specifically binds to osteoclastogenesis inhibitory factor (OCIF), and soluble OBM (sOBM) which lack a transmembrane domain; a method for the preparation thereof; a method for quantifying OBM and sOBM using these antibodies; and agents for the prevention or treatment of diseases resulting from abnormality of bone metabolism.

The antibodies of the present invention exhibit activity of neutralizing the osteoclastogenesis accelerating activity which is the biological activity of OBM and sOBM and comprises the antibodies having the following characteristics:

(a) polyclonal antibody which recognizes both mouse OBM and mouse sOBM (anti-mouse OBM/sOBM polyclonal antibody),
(b) polyclonal antibody which recognizes both human OBM and human SOBM (anti-human OBM/sOBM polyclonal antibody),
(c) monoclonal antibodies which recognizes both mouse OBM and mouse sOBM (anti-mouse OBM/sOBM monoclonal antibodies),
(d) monoclonal antibodies which recognize both human OBM and human sOBM (anti-human OBM/sOBM monoclonal antibodies), and
(e) anti-human OBM/sOBMmonoclonal antibodies which crossreact to both mouse OBM and mouse sOBM.

The polyclonal antibody which recognizes both mouse OBM and mouse sOBM (hereinafter called anti-mouse OBM/sOBM polyclonal antibody) and the polyclonal antibody which recognizes both human OBM and human sOBM (hereinafter called anti-human OBM/sOBM polyclonal antibody) were produced by the following method. The purified mouse OBM used as an antigen for immunization can be obtained according to the above-mentioned method. Especially, mouse osteoblastic stromal cell line, ST2, was treated with active-form vitamin $D_3$, and OBM on the cell membrane was purified using an OCIF-immobilized column and gel filtration chromatography, thereby obtaining natural mouse OBM (native OBM). The above-mentioned mouse OBM cDNA (SEQ ID NO:15) or human OBM cDNA (SEQ ID NO:12) was inserted into an expression vector according to conventional methods. Recombinant mouse OBM (SEQ ID NO:1) and recombinant human OBM (SEQ ID NO:11) can be obtained by expressing cDNA in animal cells such as CHO cells, BHK cells, Namalwa, or COS-7 cells, insect cells or *Eseherichia coli*, and purifying them using the same purification methods as mentioned above. These may be used as antigens for immunization. In this instance, purifying a large amount and a high level of mouse OBM or human OBM, which are membrane-bound proteins, is a task requiring a great deal of labor. On the other hand, as mentioned above, OBM, which is a membrane-bound protein, and a soluble OBM (sOBM), which is obtained by deleting transmembrane domain of OBM, are known to be almost the same in their osteoclast differentiation and maturation activities. It is possible to use mouse sOBM and human sOBM which are relatively easily expressed and purified to a high level, as antigens for immunization.

Mouse sOBM (SEQ ID NO:16) and human sOBM (SEQ ID NO:17) can be obtained by adding a nucleotide sequence encoding a known signal sequence originating from the other secretion protein in the upstream side of the 5' end of, respectively, mouse sOBM cDNA (SEQ ID NO:18) and human sOBM cDNA (SEQ ID NO:19), inserting these into an expression vector by the use of genetic engineering techniques, causing these proteins to be expressed in host cells such as various animal cells, insect cells, or *Escherichia coli*, and purifying the resultant products. The antigens for immunization thus obtained are dissolved in phosphate buffered saline (PBS), mixed with the same volume of Freund's complete adjuvant to emulsify the solution if required, and subcutaneously administered to animals about once a week to immunize these animals several times. A booster injection is given when the antibody titer reaches a maximum. Exsanguination is performed 10 days after the booster administration. The resulting antiserum is treated with ammonium sulfate precipitation. IgG fraction is purified using an anion exchange chromatography or purified by protein A-or protein G-Sepharose column chromatography after diluting the antiserum two-fold with Binding Buffer™ (BioRad Co.), to obtain the anti-mouse or anti-human OBM/sOBM polyclonal antibody.

The monoclonal antibodies of the present invention can be obtained according to the following method. In the same manner as in the case of the polyclonal antibodies, natural mouse OBM (native OBM), recombinant mouse or human OBM, or recombinant mouse or human sOBM can be used as immunogens to prepare monoclonal antibodies. Hybridomas are produced according to conventional methods by immunizing mammals with these antigens or by immunizing lymphocytes in vitro and fusing the immunized cells with myeloma cells. By analyzing the hybridoma culture supernatant thus obtained by a solid phase ELISA method, antibody-producing hybridomas recognizing the highly purified antigen are selected. The resulting hybridomas are cloned and established as stable antibody-producing hybridoma clones. These hybridomas are cultured to obtain the antibodies. Small mammals such as mice or rats are commonly used to produce hybridomas. Animals are immunized by intravenously or intraperitoneally injecting the antigen diluted to a suitable concentration using a suitable solvent such as physiological salt solution. Optionally, Freund's complete adjuvant maybe used together with antigen. These are usually injected 3-4 times, once a week or every two weeks. The immunized animals are dissected three days after final immunization. Splenocytes from the removed spleen are used as immunized cells. As mouse myeloma to be fused with immunized cells, p3/x63-Ag8, p3-U1, NS-1, MPC-11, SP-2/0, FO, P3x63 Ag8.653, and S194 can be given. A cell line such as R-210 is given as the cell of rat origin. Human antibodies are produced by immunizing human B lymphocytes in vitro and fusing the immunized cells with human myeloma cells or a cell line transformed with EB virus. The fusion of the immunized cells and myeloma cells can be carried out according to a conventional method such as the method of Koehler and Milstein (Koehler et al.: Nature 256, 495-497 (1975)). A method using electric pulse is also applicable. Immunized lymphocytes and myeloma cells are mixed at a conventionally accepted ratio and fused in an FCS-free (fetal bovine serum-free) culture medium with an addition of polyethylene glycol, and cultured in an FCS-containing HAT selection medium to select fused cells (hybridomas). Next, the hybridomas which produce antibodies were selected by using a conventional antibody detection method such as an ELISA, a plaque technique, Ouchterlony method, or aggregation method, to establish stable hybridomas. The hybridomas established in this way can be subcultured by a conventional culture method or can be stored by freezing as required. A hybridoma can be cultured by a conventional method to collect the culture supernatant or implanted in the abdominal cavity of mammals to obtain the antibody from the ascitic fluid. The antibody in the culture supernatant or ascitic fluid can be purified by a conventional method such as salting out, ion exchange and gel filtration chromatography, or protein A or protein G affinity chromatography. Almost all monoclonal antibodies obtained using sOBM as an antigen can specifically recognize not only sOBM but also OBM (such antibodies are hereinafter called anti-OBM/sOBM monoclonal antibodies). These antibodies can be used for the quantification of OBM or sOBM. The amounts of OBM and sOBM can be quantified by labeling these antibodies with a radioisotope or an enzyme and by applying the labeled antibodies to a quantification system known as a radioimmunoassay (RIA) or enzymeimmunoassay (EIA) Using these quantification systems, the amount of sOBM in a biological sample such as blood or urine can be determined with ease at high sensitivity. In addition, the amount of OBM binding to a tissue or surface of cells can be measured with ease at high sensitivity utilizing a binding assay using these antibodies.

When an antibody is used as a medication for humans, it is desirable to use a human-type anti-human OBM/sOBM antibody in view of antigenicity. The human-type anti-human OBM/sOBM antibody can be prepared according to the following methods ①, ②, or ③. In the method ①, human lymphocytes collected from human peripheral blood or spleen are immunized with an antigen human OBM or human sOBM in vitro in the presence of IL-4. The resulting immunized human lymphocytes are fused with K6H6/B5 (ATCC CRL1823) which is a hetero hybridoma of mouse and human, and screened to obtain the objective antibody producing hybridoma. The antibodies produced by the resulting antibody producing hybridomas are human type anti-human OBM/sOBM monoclonal antibodies. The antibodies neutralizing the activity of human OBM/sOBM are selected from these antibodies. However, in general, it is difficult to produce an antibody exhibiting high affinity to an antigen by the method of immunizing human lymphocytes in vitro. Therefore, in order to obtain monoclonal antibodies with high affinity to human OBM and sOBM, it is necessary to increase the affinity of the human-type anti-human OBM/sOBM monoclonal antibodies obtained by the above method. This can be done according to the following method. First, a random mutation is introduced into CDR region (particularly CDR3 region) of a human-type anti-human OBM/sOBM monoclonal antibody which neutralize OBM but have a low affinity, and make the phage to express protein. Phages which can strongly bind to human OBM/sOBM which are selected by a phage display method using plates on which human OBM/sOBM antigens are immobilized. The selected phages are grown in *Escherichia coli*. The amino acid sequence of the CDR which exhibits high affinity is determined from the nucleotide sequence of the DNA cloned in the phage. The thus-obtained DNA encoding the human type anti-human OBM/sOBM monoclonal antibodies is introduced into a commonly used expression vector for mammalian cells to produce the human type anti-human OBM/sOBM monoclonal antibodies. The target human type anti-human OBM/sOBM monoclonal antibodies exhibiting high affinity and capable of neutralizing the biological activity of human OBM/sOBM can be selected from these monoclonal antibodies. In the method ②, mouse type anti-human OBM/sOBM monoclonal antibodies are produced according to the same method as in the present invention using BALB/c mouse (Koehler et al.: Nature 256, 495-49, 1975), and monoclonal antibodies which can neutralize the biological activity of human OBM/sOBM and exhibiting high affinity are selected. These high affinity mouse anti-human OBM/sOBM monoclonal antibodies can be converted into human-type using the CDR-grafting technique (Winter and Milstein: Nature 349, 293-299, 1991) by implanting its CDR regions (CDR-1, 2 and 3) into the CDR regions of human IgG. In the method ③, human peripheral blood lymphocytes are implanted into a severe combined immune deficiency (SCID) mouse. Because the implanted SCID mouse can produce human antibodies (Mosier D. E. et al.: Nature 335, 256-259, 1988; Duchosal M. A. et al.: Nature 355, 258-262, 1992), lymphocytes which can produce the human monoclonal antibodies having specificity to human OBM/sOBM can be collected by screening SCID mouse immunized with human OBM or sOBM. The resulting lymphocytes are fused with K6H6/B5 (ATCC CRL1823) which is a heterohybridoma of mouse and human, according to the procedure described above for the human antibodies in the method ①. The resulting hybridomas are screened to obtain hybridomas which can produce the objective human monoclonal antibodies. The thus-obtained hybridomas are cultured to produce large amounts of the objective human monoclonal antibodies. The antibodies can be purified by the above-mentioned purification method. In addition, it is possible to produce recombinant human monoclonal antibodies in large amounts by constructing a cDNA library from the hybridoma which can produce the objective human monoclonal antibodies to obtain a gene (cDNA) encoding the objective human-type monoclonal antibodies by cloning, inserting this gene into a suitable expression vector by using genetic engineering techniques, and expressing the monoclonal antibodies in host cells such as various animal cells, insect cells, or *Escherichia coli*. A large amounts of purified human monoclonal antibodies can be obtained by purifying from the resulting culture supernatant by the purification methods mentioned above.

The antibodies which can neutralize the biological activity of OBM/sOBM can be obtained from the anti-OBM/sOBM monoclonal antibodies produced according to this method. The antibodies which neutralize the biological activity of OBM/sOBM are expected to be useful as agents for the treatment or prevention of bone metabolism abnormality because of their capability of blocking in vivo biological activity of OBM/sOBM, specifically the capability of preventing the induction osteoclast formation. The activity of anti-OBM/sOBM antibodies to neutralize the biological activity of OBM or sOBM can be measured by determining the activity to suppress osteoclast formation in the in vitro system. Specifically, the following in vitro osteoclastogenesis culture system can be given: ① a co-culture system of mouse osteoblastic stromal cell strain, ST2 cells, and mouse spleen cells in the presence of active-form vitamin $D_3$ and dexamethasone, ② a co-culture system comprising OBM expressing monkey kidney cell strain, COS-7, immobilizing the OBM-expressing cells with formaldehyde, and culturing mouse spleen cells on those cells in the presence of M-CSF, and ③ a culture system of mouse spleen cells in the presence of recombinant sOBM and M-CSF. The osteoclastogenesis-inhibitory activity of the anti-OBM/sOBM antibodies can be measured by adding the anti-OBM/sOBM antibodies at various concentrations to these culture systems and investigating their effects on osteoclast formation. The osteoclastogenesis-inhibitory activity of the anti-OBM/sOBM antibodies can also be evaluated by measuring their bone resorption-inhibitory activity utilizing experimental animals in vivo. Especially, ovariectomized animal model is given as an animal model with progressive osteoclast formation. The osteoclastogenesis-inhibitory activity of the anti-OBM/sOBM antibodies can be determined by administering the anti-OBM/sOBM antibodies to such experimental animals and evaluating the suppression of bone resorption (a bone density increasing activity).

The thus-obtained antibodies capable of neutralizing the OBM/sOBM biological activity are useful in pharmaceutical compositions, particularly pharmaceutical compositions to prevent or treat bone metabolism abnormality or as antibodies for an immunological diagnosis of such diseases. The preparations comprising the antibodies of the present invention can be administered either orally or non-orally. Such preparations can be safely administered to humans or animals as pharmaceutical compositions which contain the antibodies recognizing OBM and/or sOBM as an active component. As the forms of pharmaceutical composition, injection agents including intravenous drip, suppository agents, sublingual agents, percutaneous absorption agents, and the like are given. Because monoclonal antibodies are macromolecule proteins, they not only readily adhere to a glass container such as a vial or a syringe, but also are easily denatured by physicochemical factors such as heat, pH, or humidity. Therefore, the preparations should be stabilized by the addition of stabilizers, pH adjusters, buffering agents, solubilizing agents, or detergents. As the stabilizers, amino acids such as glycine and alanine, saccharides such as dextran 40 and mannose, and sugar alcohols such as sorbitol, mannitol, and xylytol can be given. These stabilizers may be used either individually or in combinations of two or more. The amount of stabilizers to be added is preferably from 0.01 to 100 times, particularly preferably from 0.1 to 10 times, the amount of the antibody. The addition of these stabilizers increases storage stability of liquid preparations or lyophilized products thereof. Phosphate buffers and citrate buffers are given as examples of the buffering agents. The buffering agents not only adjust the pH of the liquid preparations or aqueous solutions obtained by re-dissolving the lyophilized products thereof, but also increase stability and solubility of the antibody. It is desirable to add the buffering agent in an amount to make from 1 mM to 10 mM concentration of the liquid preparation or of the aqueous solution prepared from the lyophilized product. Polysolbate 20, Pulluronic F-68, and polyethylene glycol are given as examples of the detergent. A particularly preferred example is Polysolbate 80. These detergents may be used either individually or in combinations of two or more. Macromolecule proteins such as an antibody is easily adhere to glass containers.

Adherence to containers of the antibody in a liquid preparation or in an aqueous solution prepared by re-dissolving a lyophilized product can be prevented by adding such detergents at a concentration from 0.001 to 1.0%. The preparations comprising the antibodies of the present invention can be obtained by adding stabilizers, buffering agents, or agents which prevent adsorption. When the preparations are used as injection agents for medication or for animals, such injection agents should preferably have an osmotic pressure ratio of 1 to 2. The osmotic pressure ratio can be adjusted by increasing or decreasing the amount of sodium chloride when making the preparations. The amount of an antibody in a preparation can be suitably adjusted depending on the disease, route of administration, and the like. A dose of a human antibody to humans may be changed depending on the affinity of the antibody to human OBM/sOBM, especially, on the dissociation constant (Kd value) to human OBM/sOBM. The higher the affinity (or the smaller the Kd value), the less the dose to be administered to humans to obtain a certain medicinal effect. Because a human-type antibody has a long half-life in blood of about 20 days, it is sufficient to administer it to humans at a dose of about 0.1-100 mg/kg once or more in a 1-30 day period.

<Explanation of Symbols>
(A): Lane 1: Molecular weight markers
  Lane 2: A partially purified sample (Gly-HCl (pH 2.0) elution fraction) obtained from ST2 cells cultured in the presence of active-form vitamin $D_3$ and dexamethasone.
  Lane 3: A partially purified sample (Gly-HCl (pH 2.0) elution fraction) obtained from ST2 cells cultured in the absence of active-form vitamin $D_3$ and dexamethasone.
(B): Lane 1: Molecular weight markers
  Lane 2: Mouse OBM protein of the present invention after purification by reverse phase high performance liquid chromatography (Example 3)

Figure 2:
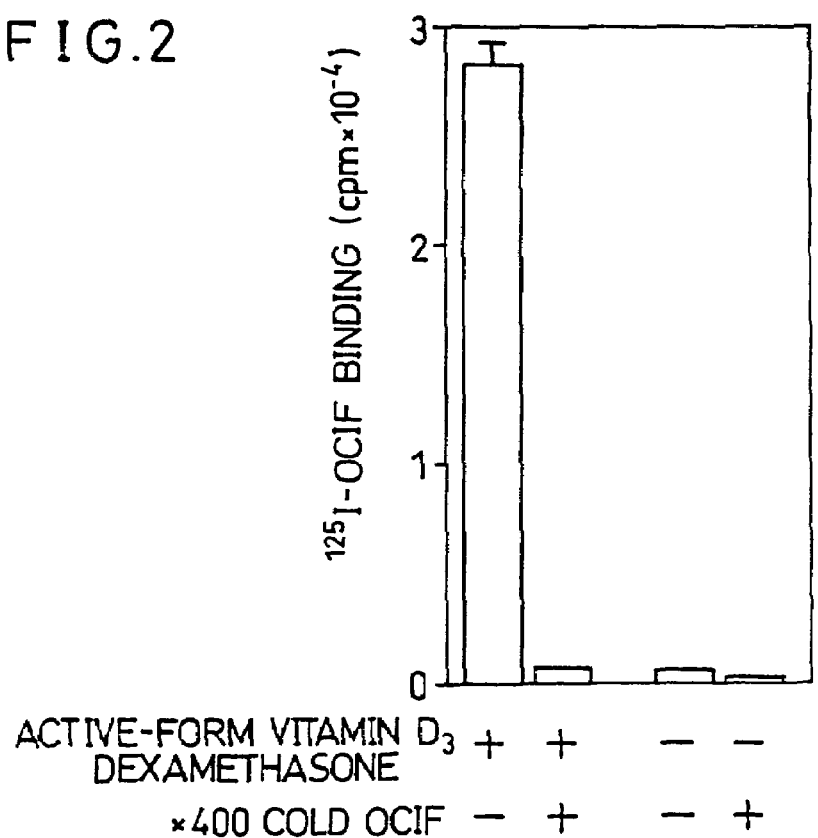

FIG. 2 shows the result of the binding assay of $^{125}I$ labeled OCIF to osteoblastic stromal cells, ST2, in Example 4.

Figure 3:
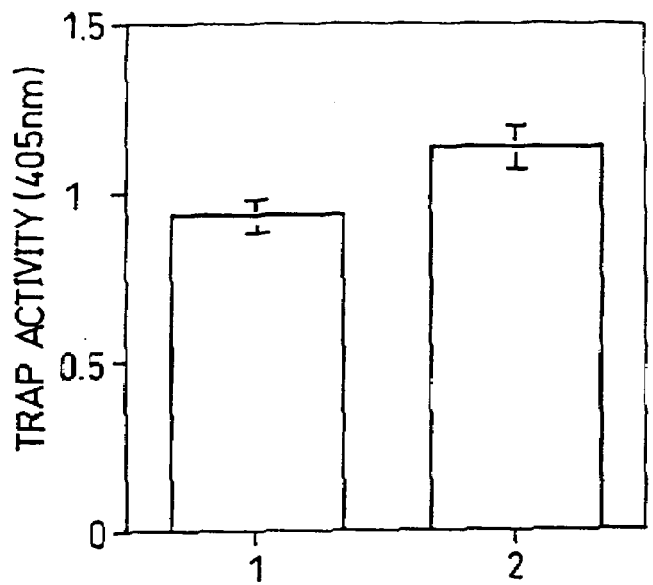

FIG. 3 shows the osteoclast formation capability of osteoblastic stromal cells ST2 from different generations in Example 5(1).

<Explanation of Symbols>
1: Ability of ST2 cells from about a $10^{th}$ subculture to support osteoclast formation.
2: Ability of ST2 cells from about a $40^{th}$ subculture to support osteoclast formation.

Figure 4:
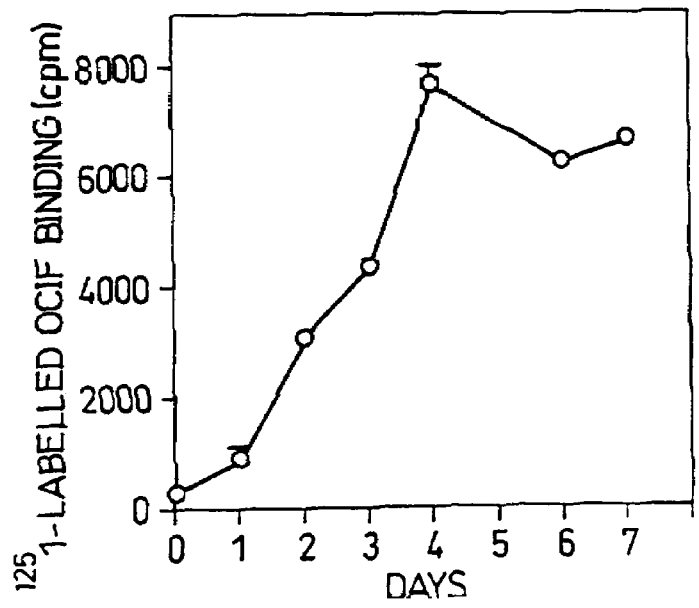

FIG. 4 shows change with the passage of time in expression of the protein of the present invention on the cell membrane of osteoblastic stromal cells cultured in the presence of active-form vitamin $D_3$ and dexamethasone in Example 5(2).

Figure 5:
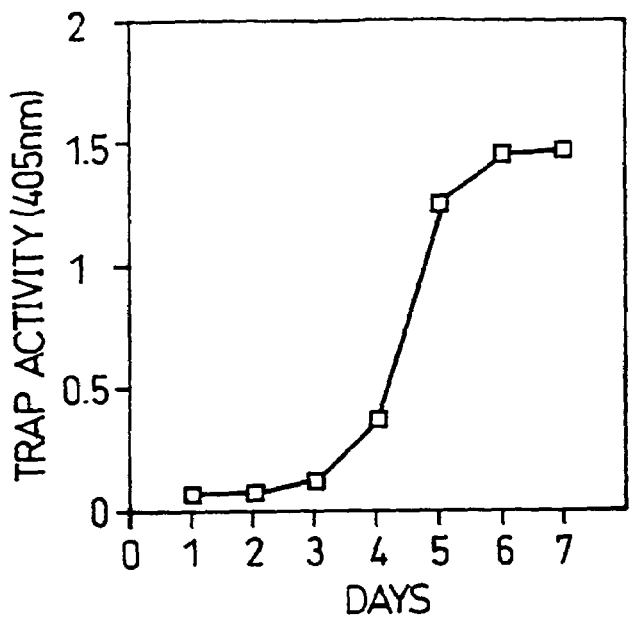

FIG. 5 shows change with the passage of time in osteoclast formation in the co-culture system of Example 5(2).

Figure 6:
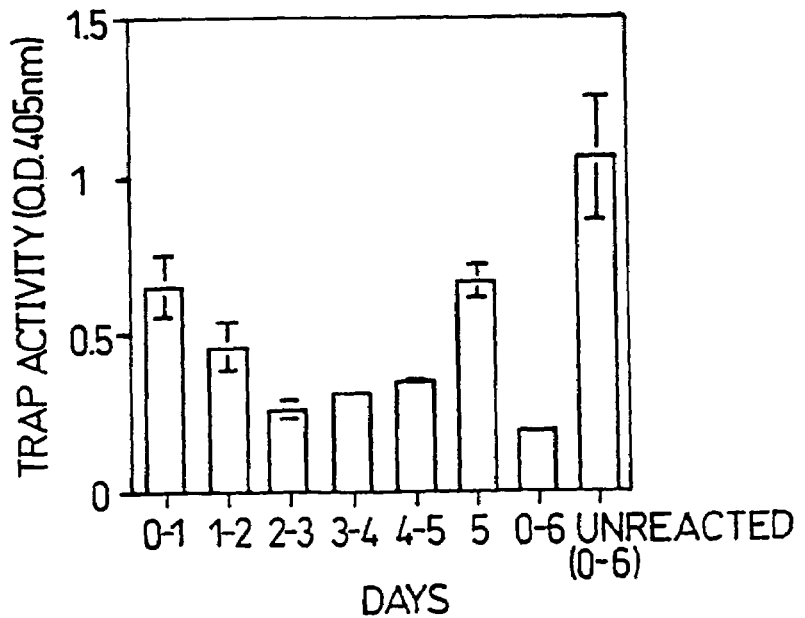

FIG. 6 shows the inhibitory effect on osteoclast formation when treated with OCIF for different culture periods during the co-culture period in Example 5(3).

Figure 7:
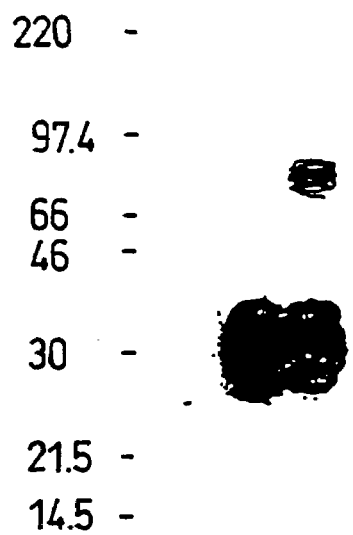

FIG. 7 shows the results of a crosslinking test of $^{125}I$-labeled OCIF with the protein of the present invention in Example 6.

Figure 8:
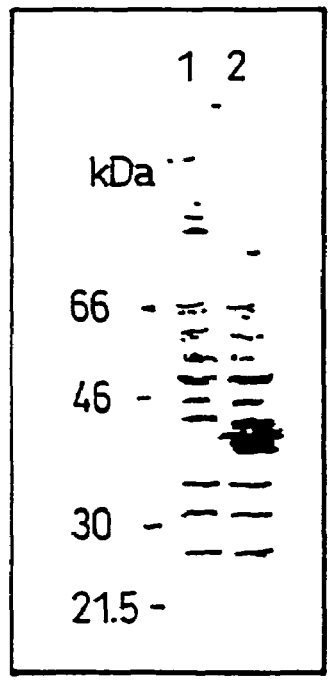

<Explanation of Symbols>
Lane 1: $^{125}I$-labeled OCIF-CDD1
Lane 2: $^{125}I$-labeled OCIF-CDD1 crosslinked with ST2 cells
Lane 3: $^{125}I$-labeled OCIF-CDD1 crosslinked in the presence of 400-fold excess of unlabeled OCIF FIG. 8 shows the result of SDS-PAGE in Example 9.

Figure 9:
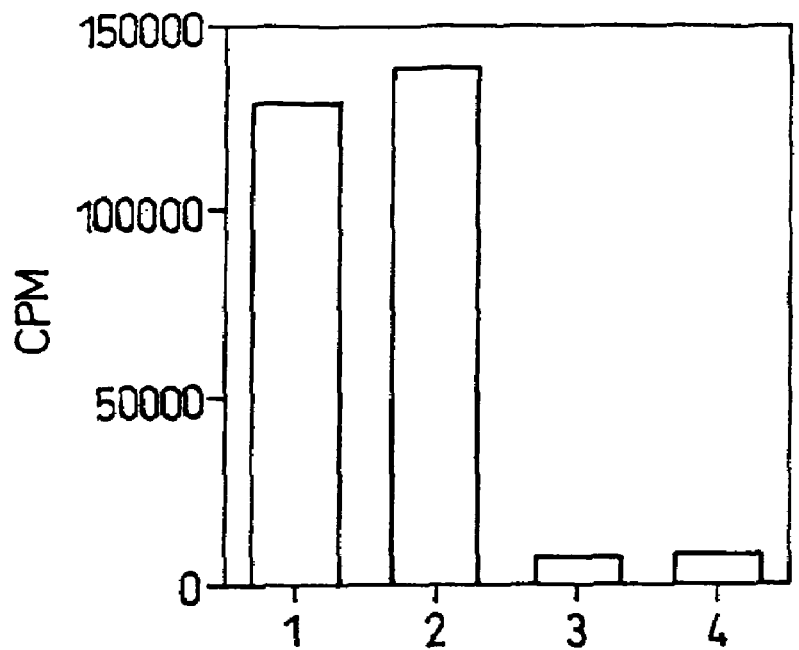

<Explanation of Symbols>
Lane 1: Proteins of pOBM291-transfected COS-7 cells immonoprecipitated in the absence of OCIF
Lane 2: Proteins of pOBM291-transfected COS-7 cells immunoprecipitated in the presence of OCIF FIG. 9 shows the results of analysis of binding capability of $^{125}I$-labeled OCIF to COS-7 cells transfected with pOBM291 in Example 10.

Figure 10:
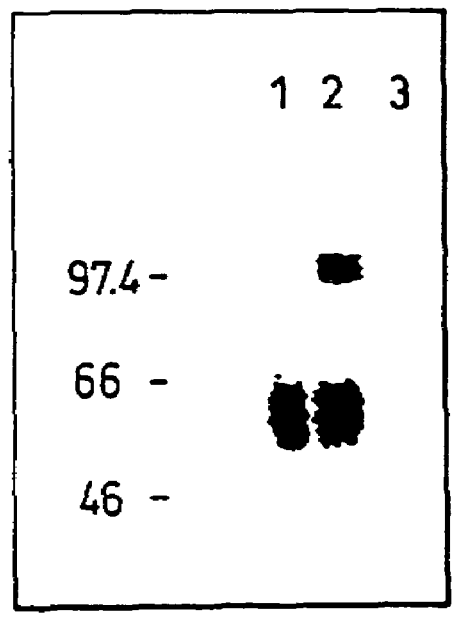

<Explanation of Symbols>
Lanes 1 and 2: The amount of the $^{125}I$-labeled OCIF binding to COS-7 cells transfected with pOBM291
Lanes 3 and 4: The amount of the $^{125}I$-labeled OCIF binding to COS-7 cells transfected with pOBM291 in the presence of 400-fold excess of unlabeled OCIF FIG. 10 shows the result of a crosslinking test using OCIF labeled with $^{125}I$ in Example 11.

<Explanation of Symbols>
Lane 1: $^{125}I$-labeled OCIF
Lane 2: $^{125}I$-labeled OCIF crosslinked with COS-7 cells transfected with pOBM291
Lane 3: $^{125}I$-labeled OCIF crosslinked with COS-7 cells transfected with pOBM291 in the presence of 400-fold excess of unlabeled OCIF FIG. 11 shows the result of a Northern Blot in Example 12.

<Explanation of Symbols>
Lane 1: RNA originating from ST2 cells cultured without addition of Vitamin D and dexamethasone
Lane 2: RNA originating from ST2 cells cultured with the addition of Vitamin D and dexamethasone FIG. 12 shows the OCIF-binding capability of the proteins in the conditioned medium at various OCIF concentrations in Example 14(2).

<Explanation of Symbols>
○: pCEP4
●: pCEP sOBM

Figure 13:
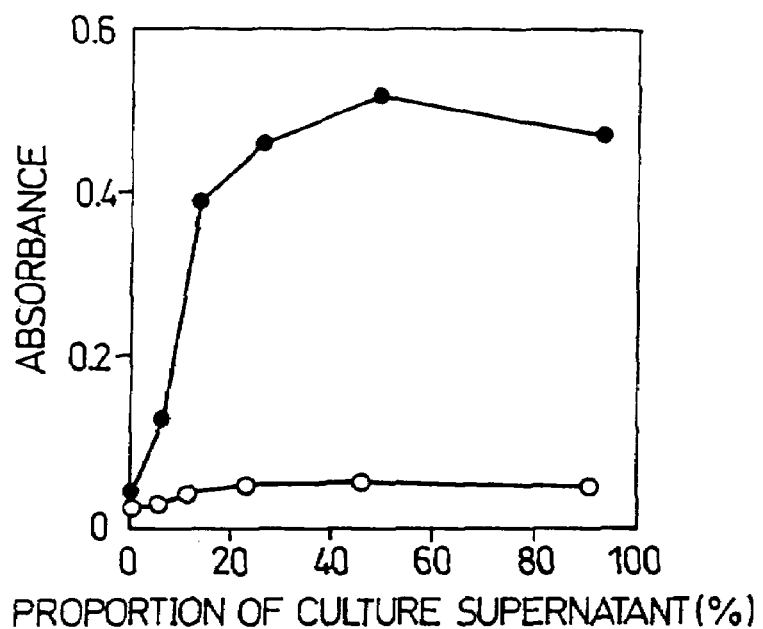

FIG. 13 shows the OCIF-binding capability of the protein in the conditioned medium at various proportions of the conditioned medium in Example 13(2).

<Explanation of Symbols>
○: PCEP4
●: PCEP sOBM

Figure 14:
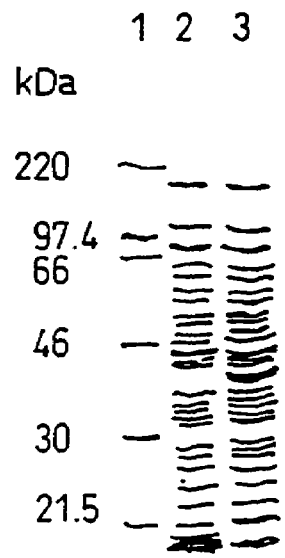

FIG. 14 shows the result of SDS-PAGE of a fusion protein consisting of thioredoxin and mouse OBM expressed in *Escherichia coli* in Example 15(2).

<Explanation of Symbols>
Lane 1: Molecular weight markers
Lane 2: Soluble protein fractions originating from GI724/pTrxFus
Lane 3: Soluble protein fractions originating from GI724/pTrxOBM25

Figure 15:
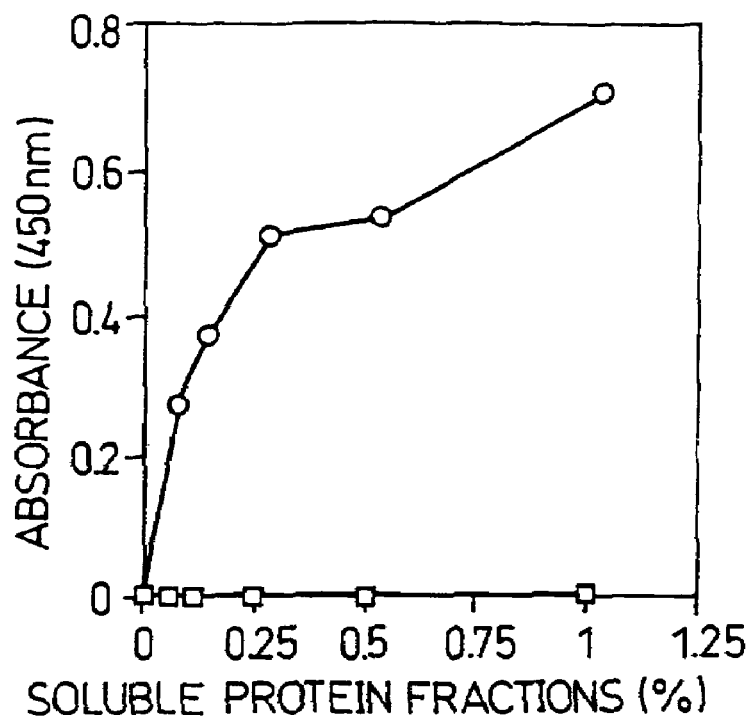

FIG. 15 shows the OCIF-binding capability at various proportions of soluble protein fractions in Example 15(3).

<Explanation of Symbols>
□: GI724/pTrxFus
○: GI724/pTrxOBM25

Figure 16:
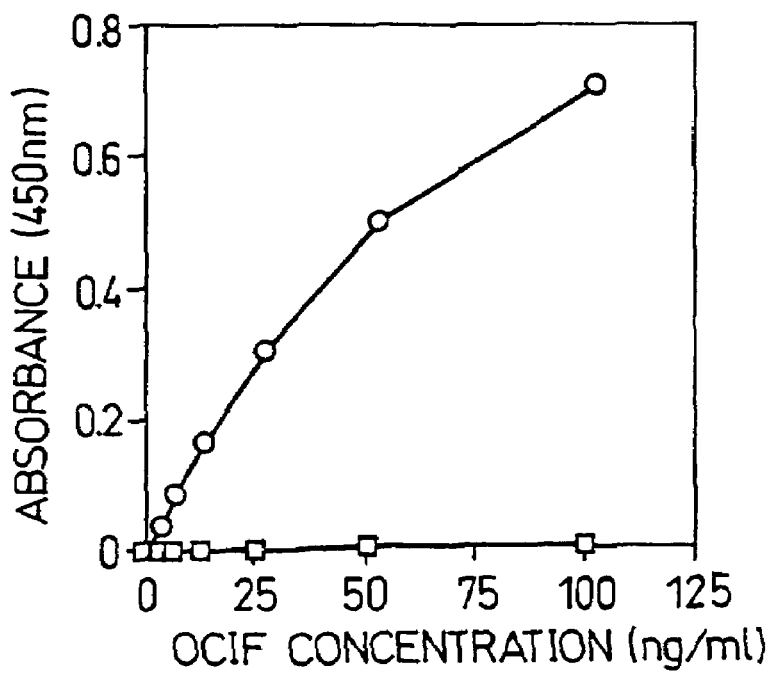

FIG. 16 shows the OCIF-binding capability of soluble protein fractions (1%) at various concentrations of OCIF in Example 15(3).

<Explanation of Symbols>
≡: GI724/pTrxFus
○: GI724/pTrxOBM25

Figure 17:
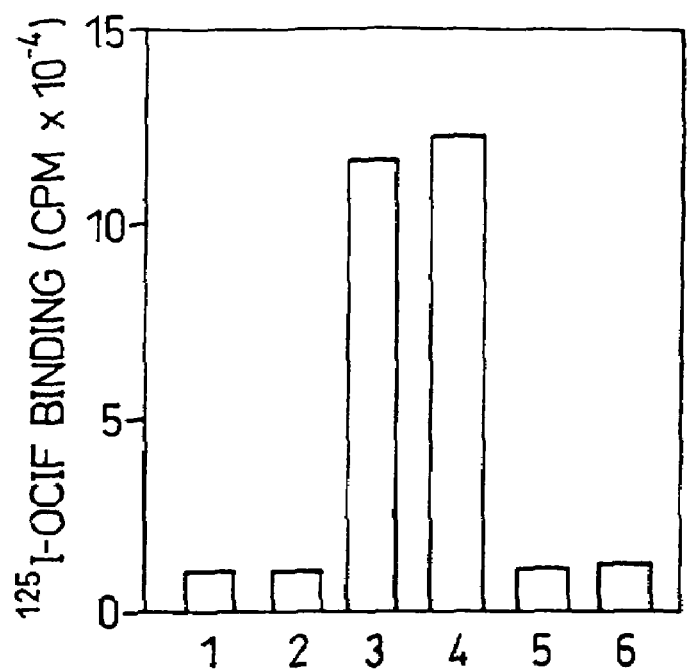

FIG. 17 shows the results of inhibition of specific binding to OCIF of mouse OBM obtained by expression of mouse OBM cDNA of the present invention and purification or natural OCIF-binding protein by a rabbit anti-mouse OBM antibody.

<Explanation of Symbols>
1: Purified OBM prepared by expression of the cDNA in the presence of the antibody, OBM+$^{125}$I-OCIF
2: The natural protein in the presence of the antibody+$^{125}$I-OCIF
3: Mouse OBM prepared by expression of the cDNA in the absence of the antibody, mouse OBM+$^{125}$I-OCIF
4: The natural protein in the absence of the antibody+$^{125}$I-OCIF
5: 3+unlabeled-OCIF (400-fold more than $^{125}$I-OCIF)
6: 4+unlabeled OCIF (400-fold more than $^{125}$I-OCIF)

Figure 18:
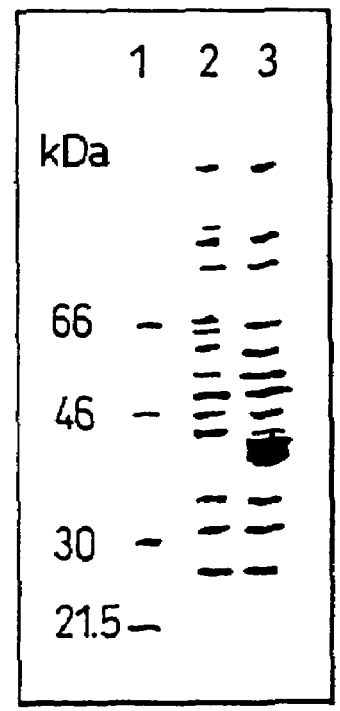

FIG. 18 shows the result of SDS-PAGE of human OBM protein expressed by the cDNA of the present invention.

Figure 19:
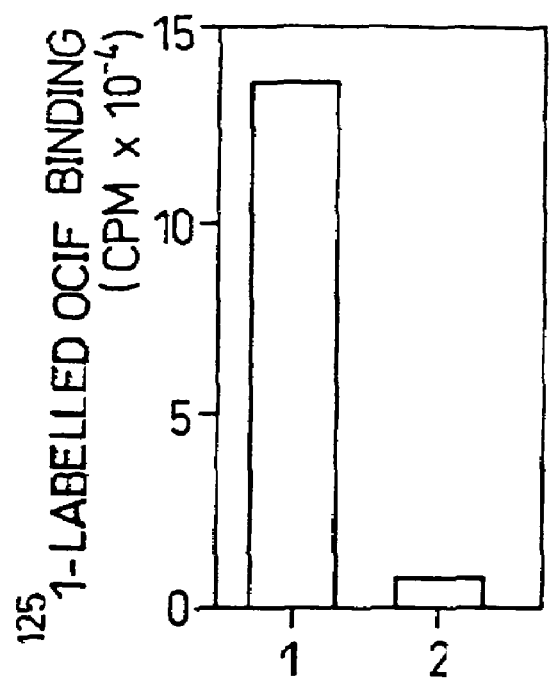

<Explanation of Symbols>
Lane 1: Molecular weight markers
Lane 2: Proteins of COS-7 cells transfected with phOBM (an expression vector containing a cDNA of the present invention), immunoprecipitated with a rabbit anti-OCIF polyclonal antibody in the absence of OCIF
Lane 3: Proteins of COS-7 cells transfected with phOBM (an expression vector containing a cDNA of the present invention), immunoprecipitated with a rabbit anti-OCIF polyclonal antibody in the presence of OCIF FIG. 19 shows the result of analysis of binding of OCIF to COS-7 cells transfected with phOBM, an expression vector containing a cDNA of the present invention.

Figure 20:
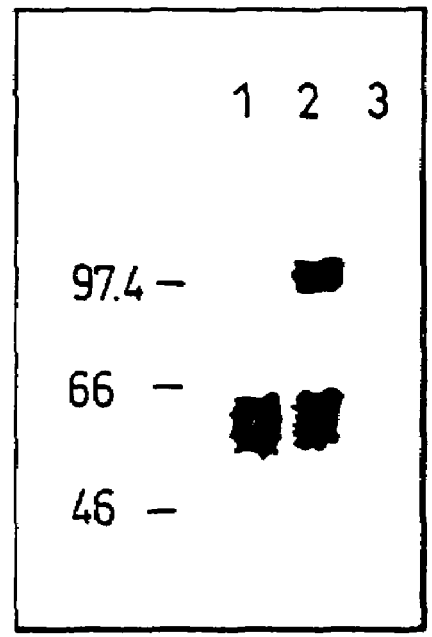

<Explanation of Symbols>
Lane 1: COS-7 cells transfected with phOBM and the addition of $^{125}$I-OCIF.
Lane 2: COS-7 cells transfected with phOBM and the addition of $^{125}$I-OCIF, in the presence of a 400-fold more unlabeled OCIF FIG. 20 shows the result of crosslinking of human OBM, which is a protein encoded by a cDNA of the present invention, with $^{125}$I-OCIF (monomer-type).

<Explanation of Symbols>
Lane 1: $^{125}$I-OCIF
Lane 2: The crosslinked products of $^{125}$I-OCIF with the proteins on the membrane of COS-7 cells transfected with phOBM.
Lane 3: The crosslinked products of $^{125}$I-OCIF with the proteins on the membrane of COS-7 cells transfected with pHOBM, in the presence of a 400-fold more unlabeled OCIF.

Figure 21:
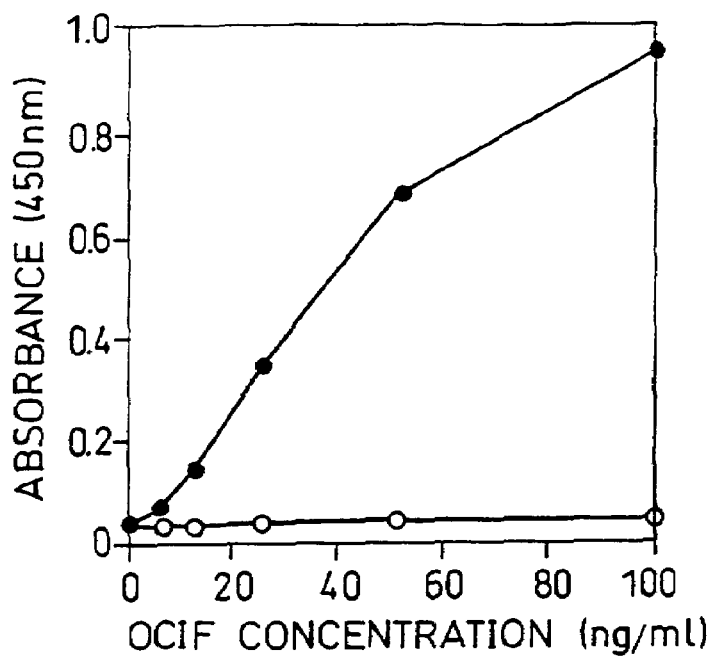

FIG. 21 shows the OCIF-binding capability of the protein (secreted-form hOBM) in the conditioned medium at various OCIF concentrations in Example 24(2).

Figure 22:
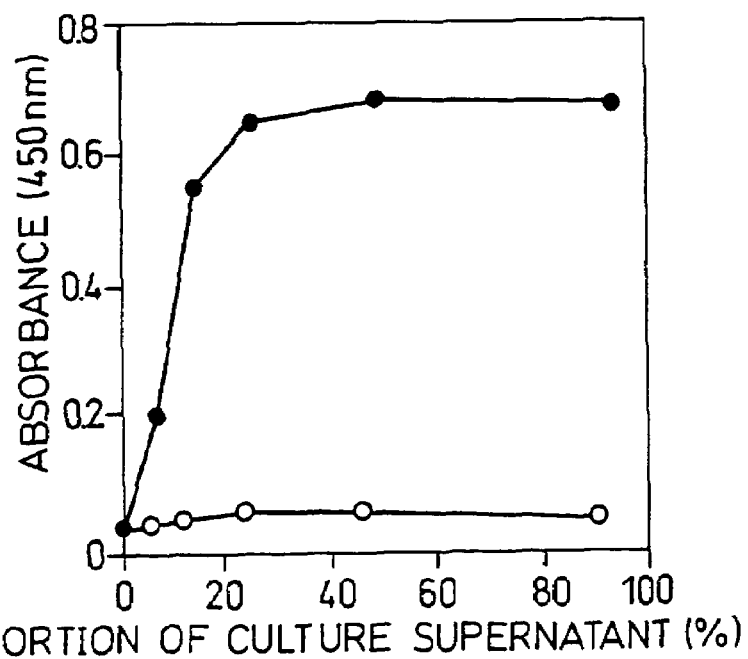

<Explanation of Symbols>
○: Conditioned medium of 293-EBNA cells transfected with pCEP4, which does not contain cDNA encoding secreted-form human OBM
●: Conditioned medium of 293-EBNA cells transfected with pCEPshOBM, which contains cDNA encoding secreted-form human OBM FIG. 22 shows the OCIF-binding capability of the protein (secreted-form human OBM) in the conditioned medium at a specific OCIF concentration while changing the amount of conditioned medium added in Example 24(2).

Figure 23:
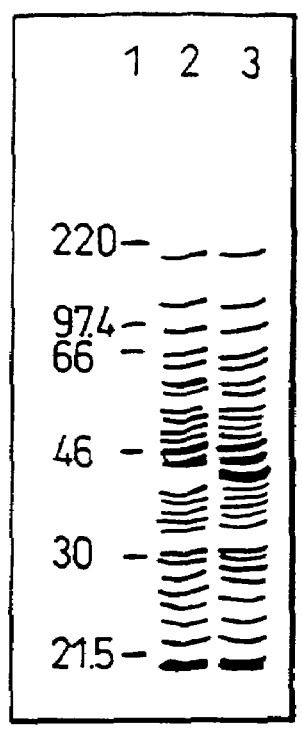

<Explanation of Symbols>
○: Conditioned medium of 293-EBNA cells transfected with pCEP4, which does not contain cDNA encoding secreted-form human OBM
●: Conditioned medium of 293-EBNA cells transfected with pCEPshOBM, which contains cDNA encoding secreted-form human OBM FIG. 23 shows the result of SDS-PAGE of a fusion protein consisting of thioredoxin and human OBM expressed in *Escherichia coli*.

Figure 24:
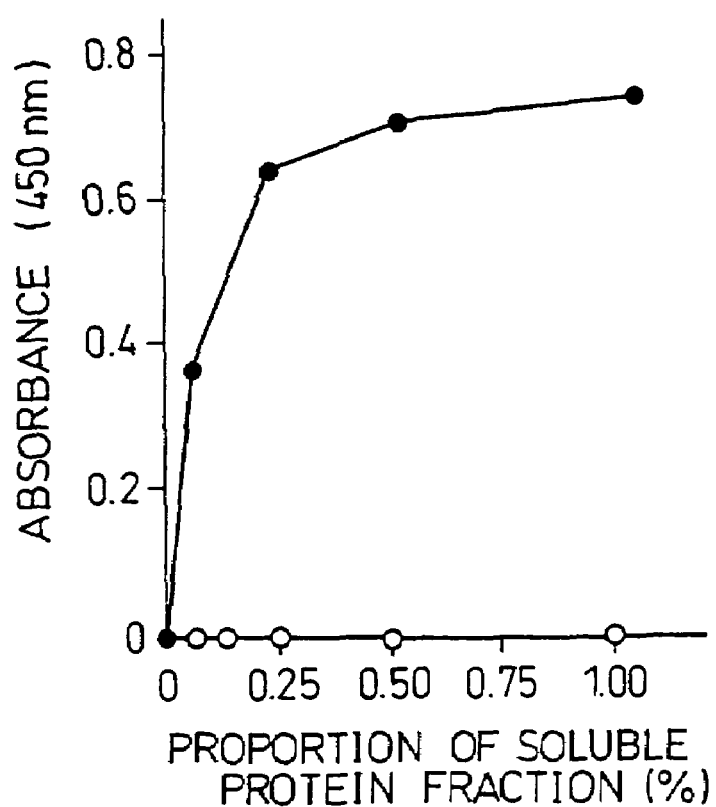

<Explanation of Symbols>
Lane 1: Molecular weight markers
Lane 2: Soluble protein fractions originating from *Escherichia coli* GI724/pTrxFus
Lane 3: Soluble protein fractions originating from *Escherichia coli* GI724/pTrxhOBM FIG. 24 shows the OCIF-binding capability of the fusion protein consisting of thioredoxin and human OBM to OCIF, when the amount of the soluble protein fraction originating from *Escherichia coli* including the fusion protein added was varied in Example 25(3).

Figure 25:
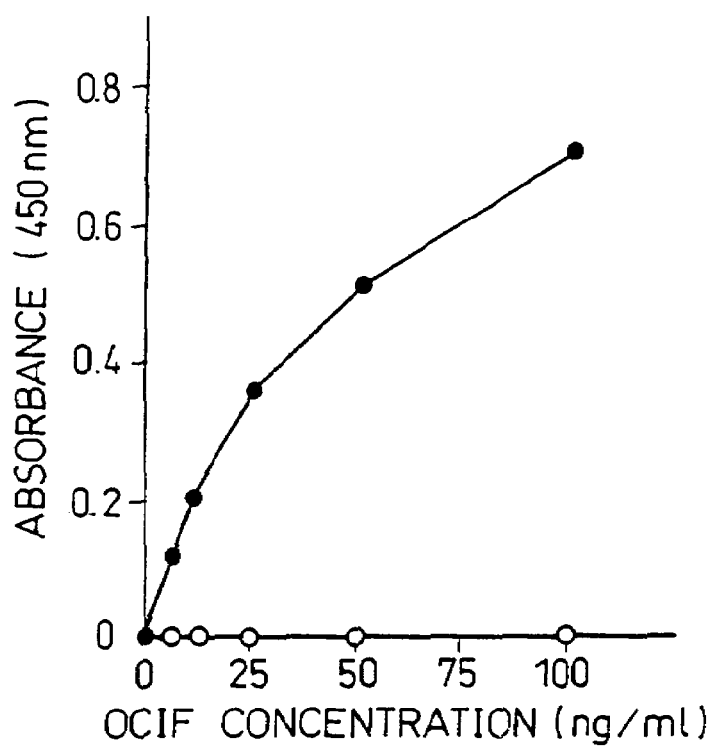

<Explanation of Symbols>
○: Soluble protein fractions originating from *Escherichia coli* GI724/pTrxFus
●: Soluble protein fractions originating from *Escherichia coli* GI724/pTrxshOBM FIG. 25 shows the OCIF-binding capability of the fusion protein of thioredoxin and human OBM in soluble protein fractions originating from *Escherichia coli* to OCIF in various concentrations in Example 25(3).

Figure 26:
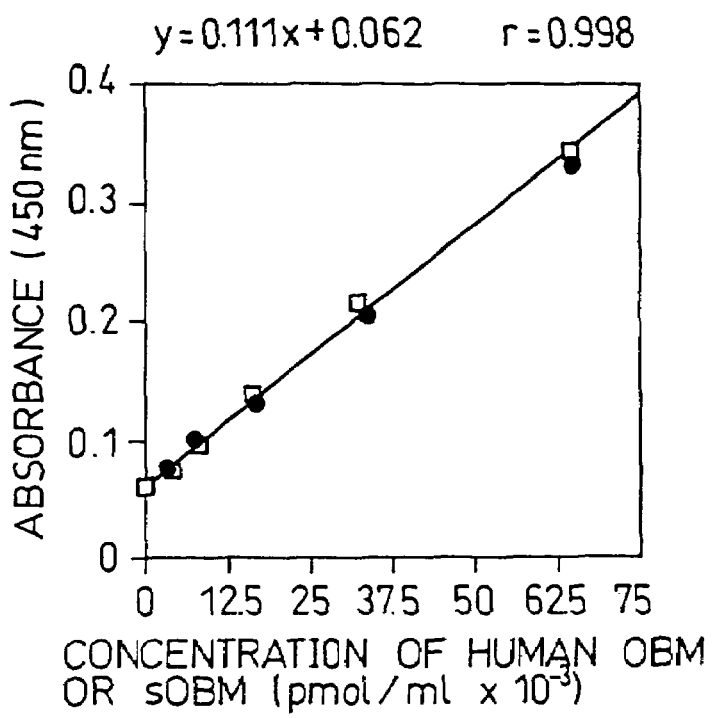

<Explanation of Symbols>
○: Soluble protein fractions originating from *Escherichia coli* GI724/pTrxFus
●: Soluble protein fractions originating from *Escherichia coli* GI72/pTrxshOBM FIG. 26 shows the result of quantifying human OBM and human sOBM by the sandwich ELISA method using the rabbit anti-human OBM/sOBM polyclonal antibody of the present invention.

<Explanation of Symbols>
≡: Human OBM
●: Human sOBM

Figure 27:
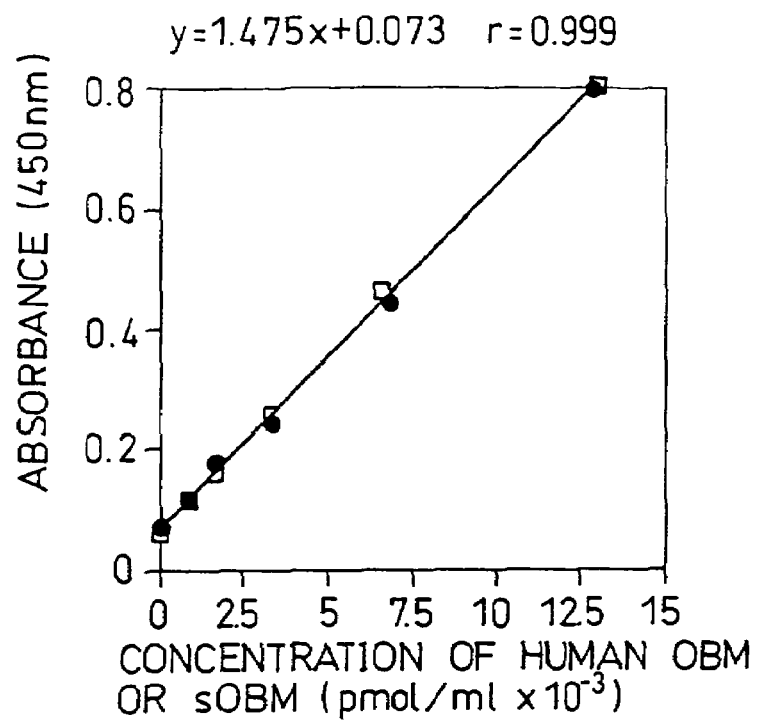

FIG. 27 shows the result of quantifying human OBM and human sOBM by the sandwich ELISA method using the anti-human OBM/sOBM monoclonal antibodies of the present invention.

<Explanation of Symbols>
≡: Human OBM
●: Human sOBM

Figure 28:
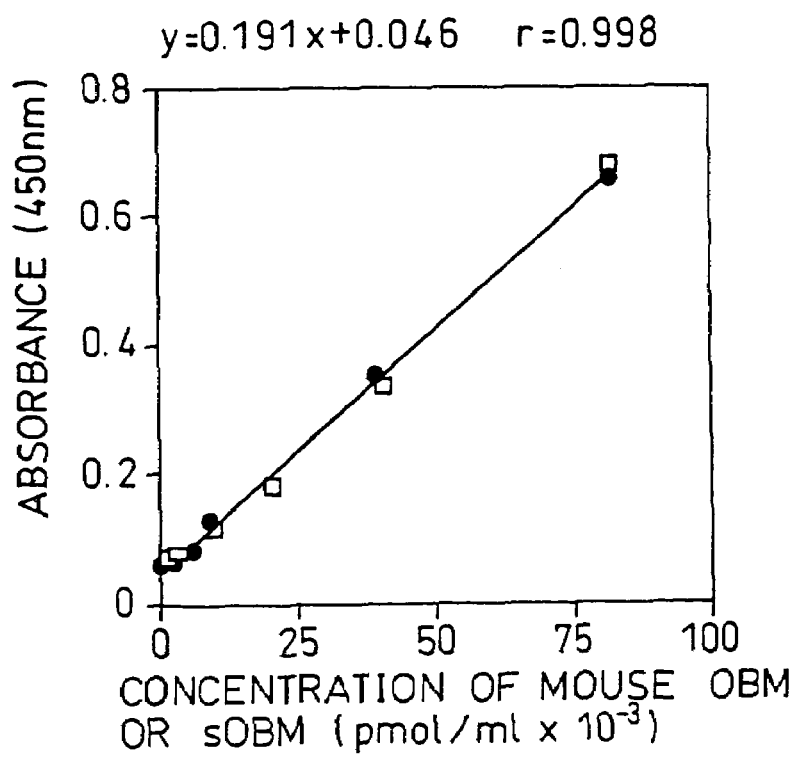

FIG. 28 shows the result of quantifying mouse OBM and sOBM by the sandwich ELISA method using the anti-human OBM/sOBM monoclonal antibodies of the present invention which cross react mouse OBM and sOBM.

<Explanation of Symbols>
≡: Mouse OBM
●: Mouse sOBM

Figure 29:
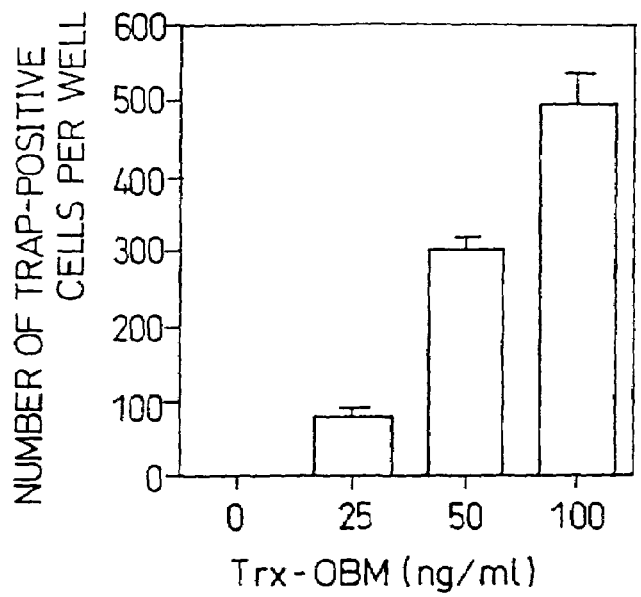

FIG. 29 shows the activity of the fusion protein consisting of thioredoxin and mouse OBM to stimulate human osteoclast-like cell formation.

Figure 30:
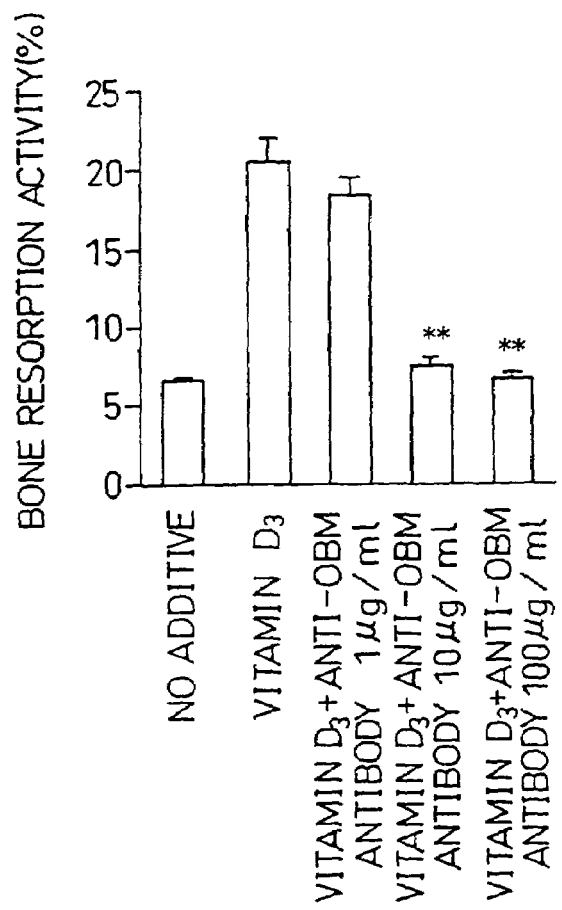

FIG. 30 shows the suppression of the anti-OBM/sOBM antibody of the bone resorption activity stimulated by vitamin $D_3$.

Figure 31:
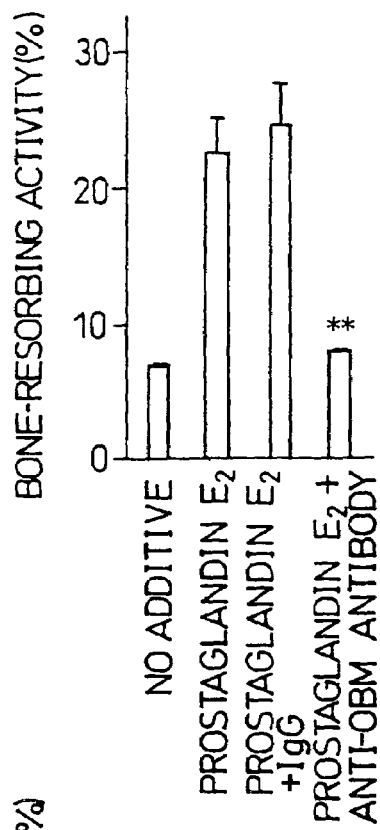

FIG. 31 shows the suppression of the anti-OBM/sOBM antibody of the bone resorption activity stimulated by prostaglandin $E_2$ ($PGE_2$).

Figure 32:
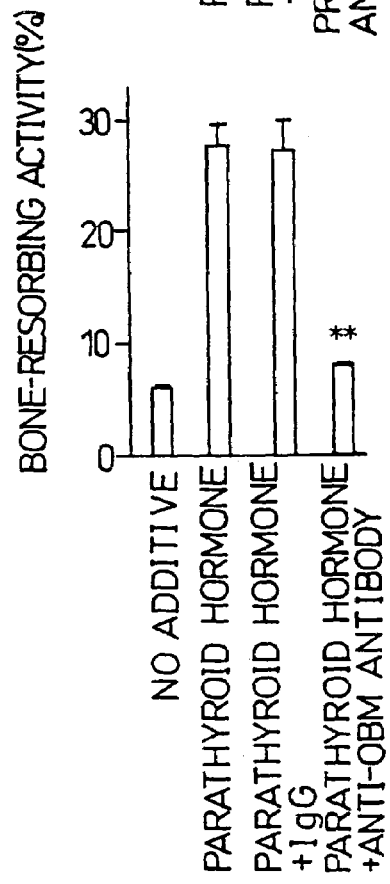

FIG. 32 shows the suppression by the anti-OBM/sOBM antibody of the bone-resorbing activity stimulated by parathyroid hormone (PTH).

Figure 33:
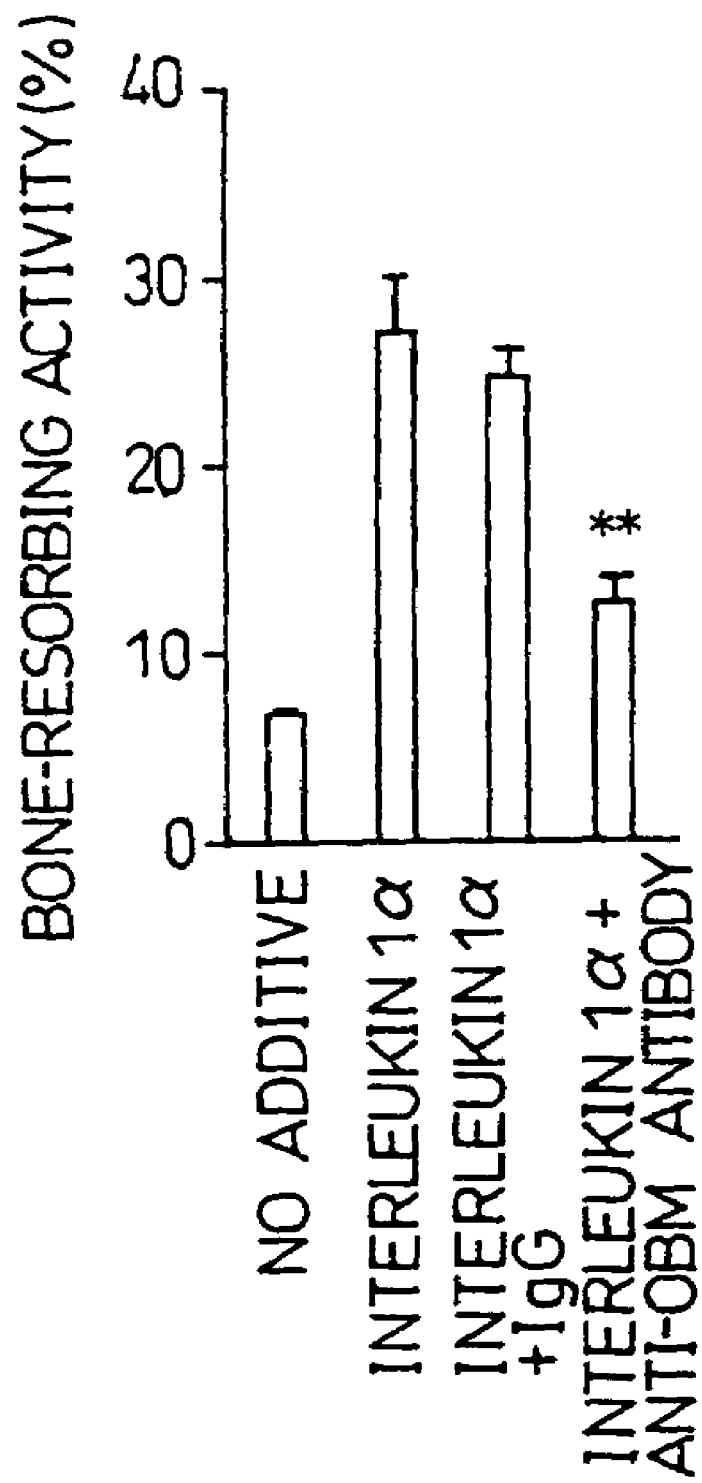

FIG. 33 shows the suppression by the anti-OBM/sOBM antibody of the bone-resorbing activity stimulated by interleukin 1α (1L-1)

BEST MODE FOR CARRYING OUT THE INVENTION

EXAMPLES

The present invention will be described in more detail by way of examples which are given for the purpose of illustration of the invention and are not limiting thereof in any way of the remainder of the disclosure.

Example 1

Preparation of the Protein of the Present Invention (1) Large-Scale Cultivation of ST2 Cells Mouse osteoblastic stromal cell line ST2 (RIKEN CELL BANK RCB0224) was cultured using α-MEM containing 10% fetal bovine serum. ST2 cells cultured to confluence in a 225 cm² T flask for adherent-cell culture were treated with trypsin and harvested from the T flask. After washing, the cells were transferred to five 225 cm² T flasks. After the addition of 60 ml of α-MEM containing $10^{-8}$ M active-form vitamin $D_3$ (Calcitriol), $10^{-7}$ M dexamethasone, and 10% fetal bovine serum, cells in each flask were cultured for 7-10 days in a $CO_2$ incubator. The cultured ST2 cells were harvested using a cell scraper and stored at −80° C. until use.

(2) Preparation of Membrane Fraction and Solubilization of Membrane-bound Proteins To the ST2 cells (volume, about 12 ml) described in Example 1(1), cultured using eighty 225 cm² T flasks, was added three times the volume (36 ml) of 10 mM Tris-HCl buffer (pH 7.2) containing protease inhibitors (2 mM APMSFP, 2 mM EDTA, 2 mM o-phenanthroline, 1 mM leupeptin, 1 μg/ml pepstatin A, and 100 unit/ml aprotinin). After vigorously agitating for 30 seconds using a vortex mixer, the cells were allowed to stand for 10 minutes on ice. The cells were homogenized using a homogenizer (DOUNCE TISSUE GRINDER, A syringe, WHEATON SCIENTIFIC Co.). The same volume (48 ml) of 10 mM Tris-HCl buffer (pH 7.2) containing the above-mentioned protease inhibitors, 0.5 M sucrose, 0.1 M potassium chloride, 10 mM magnesium chloride, and 2 mM calcium chloride was added to the homogenized cells. After stirring, the mixture was centrifuged at 600×g for 10 minutes at 4° C., thereby separating nuclei and non-homogenized cells as precipitate. The supernatant obtained by the centrifuge was centrifuged at 150,000×g for 90 minutes at 4° C., to obtain the membrane fraction of the ST2 cells as a precipitate. Eight ml of 10 mM Tris-HC1 buffer (pH 7.2) containing the above-mentioned protease inhibitors, 150 mM sodium chloride, and 0.1 M sucrose was added to this membrane fraction. After the addition of 200 μl of 20% CHAPS (3-[(3-cholamidopropyl)-dimethylamonio]-1-propanesulfonate, Sigma Co.), the mixture was stirred for 2 hours at 4° C. The mixture was then centrifuged at 150,000×g for 60 minutes at 4° C., to obtain supernatant as a solubilized membrane fraction.

Example 2

Purification of the Protein of the Present Invention (1) Preparation of OCIF-immobilized Affinity Column After replacing iso-propanol in a HiTrap NHS-activated column (1 ml, manufactured by Pharmacia Co.) with 1 mM hydrochloric acid, 1 ml of 0.2 M $NaHCO_3$/0.5 M NaCl solution (pH 8.3) containing 13.0 mg of recombinant OCIF prepared by the method of WO 96/26217 was added to the column using a syringe (5 ml, manufactured by Terumo Corp.), to effect coupling reaction at room temperature for 30 minutes. The column was fed with 3 ml of 0.5 M ethanolamine/0.5 M NaCl (pH 8.3) and 3 ml of 0.1 M acetic acid/0.5 M NaCl (pH 4.0) three times in turn to inactivate excess active groups, then the solution was replaced with 0.5 M ethanolamine/0.5 M NaCl (pH 8.3). After allowing to stand at room temperature for 1 hour, the column was washed twice alternately with 0.5 M ethanolamine/0. 5.M NaCl (pH 8.3) and 0.1 M acetic acid/0.5M NaCl (pH 4.0), and the solution was then replaced with 50 mM Tris/1 M NaCl/0.1% CHAPS buffer (pH 7.5).

(2) Purification of the Protein of the Present Invention Using OCIF-immobilized Affinity Column The purification of the OCIF-binding protein was carried out at 4° C., unless otherwise indicated. The above-mentioned OCIF-immobilized affinity column was equilibrated with 10 mM Tris-hydrochloride buffer (pH 7.2) to which the protease inhibitors described in Example 1(2), 0.15 M sodium chloride, and 0.5% CHAPS were added. About 8 ml of the solubilizedmembrane fraction described in Example 1(2) was applied to the column at a flow rate of 0.01 ml/minute. Then, the column was washed with 10 mM Tris-hydrochloride buffer (pH 7.2) to which the above-mentioned protease inhibitors, 0.15 M sodium chloride, and 0.5% CHAPS was added, for 100 minutes at a flow rate of 0.5 ml/minute. Next, the proteins adsorbed to the column was eluted with 0.1 M glycine-hydrochloride buffer (pH 3.3) containing the protease inhibitors, 0.2 M sodium chloride, and 0.5% CHAPS for 50 minutes at a flow rate of 0.1 ml/minute. In the same manner, the proteins adsorbed to the column was eluted with 0.1 M sodium citrate buffer (pH 2.0) containing the protease inhibitors, 0.2 M sodium chloride, and 0.5% CHAPS for 50 minutes at a flow rate of 0.1 ml/minute. The eluate was collected in 0.5 ml fractions. Each fraction was immediately neutralized by the addition of 2M Tris solution. The fractions derived from the elution with these buffers (each fraction consisting of 1.0-5.0 ml of eluate) were concentrated to 50-100 μl using Centricon-10 (manufactured by Amicon of U.S.A.). OCIF was added to a portion of each concentrated fraction and immunoprecipitated with anti-OCIF polyclonal antibody. The precipitated fractions were treated with SDS and subjected to SDS-PAGE. Fractions (Fr. No. 3-10) in which the band of the protein with specific binding ability to OCIF appeared were regarded as the protein fractions of the present invention.

(3) Purification of the Protein of the Present Invention by Gel Filtration

The concentrated OCIF-binding protein (the fractions obtain by the elution with 0.1 M glycine-hydrochloride buffer (pH 3.3) and 0.1 M sodium citrate buffer (pH 2.0)) prepared in Example 2(2) was applied to a Superose 12 HR10/30 column (1.0×30 cm, manufactured by Pharmacia Co.) which was equilibrated with 10 mM Tris-HCl, 0.5 M NaCl, 0.5% CHAPS (pH 7.0) and developed with the equilibration buffer as a mobile phase at a flow rate of 0.5 ml/min, and each 0.5 ml fraction was collected. The fractions containing the protein of the present invention (Fr. Nos. 27-32) were identified according to the same method as described above. Each of the fractions was concentrated using Centricon-10 (a product of Amicon).

(4) Purification by Reverse Phase High Performance Liquid Chromatography

The above-mentioned OCIF-binding protein purified by the gel filtration was applied to a $C_4$ column (2.1×250 mm, Vydac, USA) which was equilibrated with 0.1% trifluoroacetic acid (TFA) and 30% acetonitrile. The proteins bound to the column were eluted with linear gradients of acetonitrile from 30% to 55% for the first 50 minutes and from 55% to 80% during the next 10 minutes at a flow rate of 0.2 ml/min. Peaks of eluted proteins were detected by measuring optical density at 215 nm. Proteins in the different peaks were analyzed to identify the fractions containing the protein of the present invention, and a highly purified protein of the present invention was obtained.

Example 3

SDS-PAGE of the Purified Protein of the Present Invention

Figure 1:
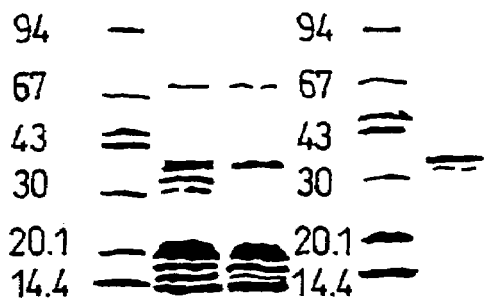
FIG. 1 shows the result of SDS-PAGE of mouse OBM protein of the present invention obtained in Example 3.

The solubilized membrane fraction prepared from ST2 cells which were cultured in the presence or absence of active-form vitamin $D_3$ was subjected to purification with the OCIF-immobilized affinity column. The purified preparations were subjected to SDS-PAGE. As shown in FIG. 1(A), a major protein band with MW of about 30,000-40,000 was detected only in the purified preparation from ST2 cells which was cultured in the presence of the active-form vitamin $D_3$, proving that the protein which specifically binds to OCIF (i.e. the protein of the present invention) can be selectively purified by the OCIF-immobilized affinity column. However, bands of several proteins (other than the protein of the present invention) which non-specifically bind to carriers or spacers of the OCIF-immobilized column were detected in both of the purified preparations. The proteins other than the protein of the present invention were removed according to the above-described method by gel filtration and C4 reverse phase chromatography. SDS-PAGE of the obtained highly purified protein of the present invention is shown in FIG. 1(B). The highly purified protein of the present invention was found to be electrophoretically homogeneous and had a molecular weight of about 30,000-40,000.

Example 4

Binding test of OCIF to Osteoblasts (1) Preparation of $^{125}$I-labeled OCIF

OCIF was labeled with $^{125}$I by the Iodogen method. Specifically, 20 μl of 2.5 mg/ml Iodogen-chloroform solution was transferred to a 1.5 ml Eppendorf tube and chloroform was evaporated off at 4° C., to obtain a tube coated with Iodogen. The tube was washed three times with 400 μl of 0.5 M sodium phosphate buffer (Na-Pi, pH 7.0). Five μl of 0.5 M Na-Pi (pH 7.0) was added to the tube. Immediately after the addition of 1.3 μl (18.5 MBq) of Na—$^{125}$I solution (NEZ-033H20, manufactured by Amersham Co.); 10 μl of 1 mg/ml rOCIF solution (monomer type or dimer type) was added to the tube. After mixing with a vortex mixer, the mixture was allowed to stand at room temperature for 30 seconds. The solution was transferred to a tube containing 80 μl of a solution of 10 mg/ml potassium iodide in 0.5 M Na-Pi (pH 7.0) and 5 μl of a phosphate buffered saline containing 5% bovine serum albumin, and stirred. The mixture was applied to a spin column (1 ml, G-25 fine, manufactured by Pharmacia Co.) which was equilibrated with phosphate buffered saline containing 0.25% bovine serum albumin and the column was centrifuged for 5 minutes at 2,000 rpm. Four hundred μl of a phosphate buffered saline containing 0.25% bovine serum albumin was added to the fraction eluted from the column and the mixture was stirred. A two μl of the aliquot was removed to measure the radioactivity using a gamma counter. The radiochemical purity of the $^{125}$I-labled OCIF was determined by measuring the radioactivity precipitated with 10% TCA. The biological activity of the $^{125}$I-labeled OCIF was measured according to the method described in WO 96/26217. The concentration of the $^{125}$I-labeled OCIF was measured by ELISA according to the following procedure.

(2) Measurement of the Concentration of $^{125}$I-labeled OCIF by ELISA

One hundred μl of 50 mM $NaHCO_3$ (pH 9.6) in which the anti-OCIF rabbit polyclonal antibody described in WO 96/26217 was dissolved to a concentration of 2 μg/ml was added to each well of a 96-well immuno-plate (MaxiSorp™, a product of Nunc Co.) The plate was allowed to stand overnight at 4° C. After removing the solution by suction, 300 μl of Block Ace™ (Snow Brand Milk Products Co., Ltd.)/phosphate buffered saline (25/75) solution was added to each well. The plate was then allowed to stand for two hours at room temperature. After removing the solution by suction, the wells were washed three times with phosphate buffered saline containing 0.01% Polysorbate 80 (P-PBS). Next, 300 μl of Block Ace™/phosphate buffered saline (25/75) solution to which $^{125}$I-labeled OCIF or the standard OCIF preparation was mixed, was added to each well. The plate was then allowed to stand for two hours at room temperature. After removing the solution by suction, each well was washed six times with 200 μl of P-PBS.

One hundred μl of Block Ace™ (Snow Brand Milk Products Co., Ltd.)/phosphate buffered saline (25/75) solution containing peroxidase labeled rabbit anti-OCIF polyclonal antibody was added to each well. The plate was allowed to stand for two hours at room temperature. After removing the solution by suction, the wells were washed six times with 200 μl P-PBS. Then, 100 μl of TMB solution (TMB Soluble Reagent, High Sensitivity, Scytek Co.) was added to each well. After incubating at room temperature for 2-3 minutes, 100 μl of stopping solution (Stopping Reagent, Scytek Co.) was added to each well. Absorbance of each well was measured at 490 nm using a microplate reader. The concentration of $^{125}$I-labeled OCIF was determined from a calibration curve prepared using the standard preparation of OCIF.

(3) Binding Test of OCIF to Osteoblasts or Spleen Cells

Mouse osteoblastic stromal cell line ST2 or spleen cells were suspended in α-MEM containing 10% fetal bovine serum (FBS), either with or without $10^{-8}$ M active-form vitamin $D_3$ (Calcitriol) and $10^{-7}$ M dexamethasone, to a concentration of $4\times10^4$ cells/ml (ST2 cells) or $2\times10^6$ cells/ml (spleen cells), respectively. Each cell suspension was inoculated into a 24-well micro plate. The cells were cultured for 4 days in a $CO_2$ incubator. After washing the cells with α-MEM, 200 μl of medium for the binding test (α-MEM to which 0.2% bovine serum albumin, 20 mM Hepes buffer, and 0.2% $NaN_3$ were supplemented), containing 20 ng/ml of above-described $^{125}$I-labeled OCIF (monomer form or dimer form), was added to each well. To the wells for the measurement of non-specific binding, 200 μl of the medium for the binding test containing 8 μg/ml of rOCIF (400 times concentration) in addition to 20 ng/ml of $^{125}$I-labeled OCIF was added. The cells were cultured for one hour in a $CO_2$ incubator and washed 3 times with 1 ml of a phosphate buffered saline. In this procedure, spleen cells were washed by centrifuging the 24-well plate in each washing step, because the spleen cells were non-adherent. After washing, 500 μl of 0.1 N NaOH solution was added to each well and the plate was allowed to stand for 10 minutes at room temperature to dissolve the cells. The amount of RI in each well was measured by a gamma counter.

As shown in FIG. 2, $^{125}$I-labeled OCIF did not bind to the cultured spleen cells, but specifically bound only to the osteoblastic stromal cells which were cultured in the presence of active-form vitamin $D_3$. The results indicated that the protein of the present invention is a membrane bound protein induced by active-form vitamin $D_3$ and dexamethasone on osteoblastic stromal cells.

Example 5

Biological Activity of the Protein of the Present Invention (1) Osteoclasts-formation Supported by Osteoblastic Stromal Cells The osteoclasts formation-supporting capability of osteoblastic stromal cells was evaluated by measuring tartaric acid resistant acid phosphatase activity (TRAP activity) of the formed osteoclasts. Specifically, spleen cells ($2 \times 10^5$ cells/100 μl/well) from a ddy mouse (8-12 weeks old) and mouse osteoblastic stromal cells ST2 ($5 \times 10^3$ cells/100 μl/well) were suspended in α-MEM to which $10^{-8}$ M active-form vitamin $D_3$, $10^{-7}$ M dexamethasone, and 10% fetal bovine serum were added. The cells were innoculated into 96-well plates and cultured for one week in a $CO_2$ incubator. After washing each well with phosphate buffered saline, 100 μl of ethanol/acetone (1:1) was added to each well, and the cells were immobilized at room temperature for one minute. After immobilization, 100 μl of 50 mM citrate buffer (pH 4.5) containing 5.5 mM p-nitrophenol phosphate and 10 mM sodium tartarate was added to each well. After 15 minutes of reaction at room temperature, 0.1 N NaOH solution was added to each well and absorbance at 405 nm was measured using a microplate reader. The results of osteoclasts-formation by ST2 cells with a passage number of about 10 or 40 after purchasing the cells from RIKEN CELL BANK are shown in FIG. 3. The results indicate that the ST2 cells with a higher passage number exhibit more potent ability to support osteoclasts-formation.

(2) Time Course Change of Expression of the Protein of the Present Invention on Membrane of Osteoblastic Stromal Cells in a Culture System Which Include Active-Form Vitamin $D_3$ and Dexamethasone and Time Course Change of Osteoclasts-Formation in the Co-Culture System In the same manner as in Example 4(3), osteoblastic stromal cell ST2 was cultured for 7 days in the presence of active-form vitamin $D_3$ and dexamethasone. The OCIF-binding test was carried out using $^{125}$I-labeled OCIF (monomer type) as described in the experiment in Example 4(1). Non-specific binding was measured by competing $^{125}$I-OCIF binding to ST2 cells with 400-fold concentration of unlabeled OCIF. As a result, it was confirmed that the amount of specific binding of $^{125}$I-labeled OCIF increase in accordance with increase in culture period in the presence of active-form vitamin $D_3$ and dexamethasone. Specifically, as shown in FIGS. 4 and 5, the protein of the present invention was expressed on the surface of ST2 cells by active-form vitamin $D_3$ in accordance with increase in culture period and the expression reached a maximum on the fourth day of culture. On the other hand, osteoclast-like cells are formed by coculturing mouse spleen cells and ST2 cells in the presence of active-form vitamin $D_3$. TRAP (a marker enzyme of osteoclasts)-positive mononuclear pre-osteoclast-like cells are formed on the third or fourth day of the culture. More differentiated and mature TRAP-positive multinuclear cells are formed on the fifth to sixth day of the culture. A good correlation between time-course of the expression of the protein of the present invention and osteoclasts-formation was thus demonstrated.

(3) Inhibition of Osteoclasts Formation by OCIF Treatment for Different Period During the Co-culture To make it clear that the protein of the present invention is a factor involved in the osteoclasts-formation, the cells were treated with 100 mg/ml OCIF for different culture periods during the six day co-culture period described in the above-mentioned Example 5(2) (two consequtive days in the six-day period, except for the 5th day for which a one-day period was applied). As a result, as shown in FIG. 6, OCIF treatment at 48-96 hours after start of the culture at which expression of the protein of the present invention on ST2 cells is maximal was found to be most effective for inhibiting formation of osteoclasts. Specifically, it was confirmed that OCIF controls osteoclast formation by binding to ST2 cells via the protein of the present invention.

Based on the results of the above experiments, the protein of the present invention was confirmed to be induced on cell membrane of osteoblastic stromal cells by active-form vitamin $D_3$ and dexamethasone and to exhibit a biological activity to support or accelerate differentiation or maturation of osteoclasts.

Example 6

Crosslinking Test for $^{125}$I-labeled OCIF and the Protein of the Present Invention To identify the protein of the present invention more clearly, the protein of the present invention was crosslinked with $^{125}$I-labeled OCIF. Mouse osteoblastic stromal cell line ST2 was cultured for four days in the presence or absence of active-form vitamin $D_3$ and dexamethasone in the same manner as described in Example 4 (3). After washing the cells with 1 ml of phosphate buffered saline, 200 μl of medium for binding test (α-MEM to which 0.2% bovine serum albumin, 20 mM Hepes buffer, 0.2% $NaN_3$, and 100 μg/ml heparinwere added), containing 25 ng/ml of $^{125}$I-labeled OCIF (monomer type) or 40 ng/ml of $^{125}$I-labeled OCIF-CDD1 which was obtained by expressing the protein of Sequence ID No. 76 (WO 96/26217) in animal cells, was added. The above-mentioned culture medium for the binding test was further supplemented with 400-fold concentration of OCIF and was added to the other wells to assess non-specific binding. After culturing for one hour in a $CO_2$ incubator, each well was washed three times with 1 ml of phosphate buffered saline containing 100 μg/ml heparin. Five hundred μl of phosphate buffered saline containing 100 μg/ml crosslinking agent, DSS (Disuccinimidyl suberate, Pierce Co.), was added to each well and the plate was kept for 10 minutes at 0° C. The wells were washed twice with 1 ml of phosphate buffered saline at 0° C. One hundred μl of 20 mM Hepes buffer containing 1% Triton X-100, 10 μM pepstatin, 101 μM leupeptin, 2 mM PMSF (phenylmethylsulfonyl fluoride), 10 μM antipain, and 2 mM EDTA, was then added to each well. The plate was allowed to stand for 30 minutes at room temperature to dissolve the cells. Fifteen μl of these samples were treated with SDS under non-reducing conditions according to conventional method and subjected to SDS-polyacrylamide gel electrophoresis(4-20% polyacrylamide gradient, manufactured by Daiichi Chemical Co., Ltd.). After electrophoresis, the gels were dried and exposed to BioMax MS film (manufactured by Kodak) for 24 hours at −80° C. using BioMax MS intensifying screens (manufactured by Kodak). After exposure, the film was developed by conventional method. A band of crosslinking product with a molecular weight of 90,000-110,000 was detected when the $^{125}$I-labeled OCIF (monomer type, 60 kDa) was used. When the $^{125}$I-labeled OCIF-CDD1 (31 kDa) was used, a band of crosslinking product of about 70-80 kDa (average, 78 kDa) was detected as shown in FIG. 7.

Example 7

Analysis of the Protein of the Present Invention Expressed on ST Cells by Scatchard Plot The above-mentioned $^{125}$I-labeled OCIF (monomer type) was added to a concentration of 1,000 pM to the culture medium for binding test (α-MEM containing 0.2% bovine serum albumin, 20 mM Hepes buffer, and 0.2% $NaN_3$) and the culture medium was serially diluted at a rate to ½ with the culture medium not containing $^{125}$I-labeled OCIF. Solutions for measuring non-specific binding were prepared by further adding 400-fold concentration of monomer-form OCIF to these solutions. Two hundred μl of the prepared solutions were added to the above-mentioned wells with ST2 cells cultured for 4 days (passage number, about 10) in the presence of $10^{-8}$ M active-form vitamin $D_3$ (Calcitriol) and $10^{-7}$ M dexamethasone, to assess binding of $^{125}$I-labeled OCIF in the same method as described in Example 4(3). The results were subjected to Scatchard Plot analysis to determine the dissociation constant of OCIF and OCIF-binding protein and the number (site) of OCIF-binding protein per a ST2 cell. As a result, the dissociation constant of OCIF and the protein of the present invention was found to be 280 pM, and the number of the site of OCIF-binding protein per a ST2 cell was approximately 33,000/cell. Based on the finding in Example 5(1) that osteoclasts-formation supported by the ST2 cells with passage number about 40 was more extensive than that with passage number about 10, the number (the site) of the protein of the present invention expressed on the ST2 cell with a passage number about 40 was assessed. The number (site) was 58,000/cell and was clearly larger than the ST2 cells with passage number about 10, indicating that the amount of the protein of the present invention expressed on ST2 cells is related to their potency to support osteoclasts-formation. The results indicated that the protein of the present invention is a factor that supports or induces differentiation or maturation of osteoclasts.

Example 8

Cloning of OBMcDNA (1) Extraction of RNA from mouse ST2 Cells

Mouse osteoblastic stromal cell line ST2 (RIKEN CELL BANK, RCB0224) was cultured in α-MEM (Gibco BRL Co.) containing 10% fetal bovine serum. ST2 cells cultured to confluent in a 225 $cm^2$ T-flask for adherent cells were treated with trypsin to harvest the cells from the T-flask. The cells were washed and transferred to five 225 $cm^2$ T-flasks. Sixty ml of α-MEM containing $10^{-8}$ M active-form vitamin $D_3$ (Calcitriol, Wako Pure Chemicals Co., Ltd.), $10^{-7}$ M dexamethasone, and 10% fetal bovine serum was added to each flask and the cells were cultured for 5 days in a $CO_2$ incubator. Total RNA was extracted from the cultured ST2 cells using ISOGEN (Wako Pure Chemicals Co., Ltd.). Poly $A^+$ RNA was prepared from about 600 μg of the total RNA using an Oligo (dT)-cellulose column (5'-3' Prime Co.) About 8 μg of Poly $A^+$RNA was obtained.

(2) Construction of Expression Library

Double-stranded cDNA was synthesized from 2 μg of poly$A^+$ RNA obtained in Example 8(1) using a Great Lengths cDNA Synthesis kit (Clontech Co.) according to the instruction in the manual. Specifically, 2 μg of poly$A^+$ RNA and Oligo $(dT)_{25}$ (dN) primer were mixed and distilled water was added to the mixture to make the final volume to 6.25 μl. After incubation for about 3 minutes at 70° C., the mixture was cooled on ice for 2 minutes. To the mixture were added 2.2 μl of distilled water, 2.5 μl of 5× First-strand buffer, 0.25 μl of 100 mM DTT (dithiothreitol), 0.5 μl of PRIME RNase inhibitor (1 U/ml) (5'-3' Prime Co.), 0.5 μl of [α-$^{32}$P]dCTP (Amersham Co., 3000 Ci/mmol) diluted 5-fold with distilled water to make 2 μCi/μl, 0.65 μl of dNTP (20 mM each), and 1.25 μl (250 unit) of MMLV (RNaseH$^-$) reverse transcriptase. The mixture was incubated for 90 minutes at 42° C., followed by the further addition of 62.25 μl of distilled water, 20 μl of 5× second-strand buffer, 0.75 μl of dNTP (20 mM each), and 5 μl of Second-strand enzyme cocktail. The resulting mixture was maintained at 16° C. for two hours. Then, 7.5 units of T4DNA polymerase was added to this reaction mixture. After incubation at 16° C. for 30 minutes, the reaction was terminated by the addition of 5 μl of 0.2 M EDTA. After a phenol-chloroform treatment, the product was precipitated with ethanol. An EcoRI-SalI-NotI linker (Clontech Co.) was attached to the ends of the resultant double-stranded cDNA. Then, the ends were phospholylated and the product was applied on a size fractionation column to obtain cDNA with a length more than 500 bp. DNA was precipitated with ethanol, dissolved in water and ligated to pcDL-SR α296 (Molecular and Cellular Biology, Vol. 8, pp 466-472, 1988) which had been cut with a restriction enzyme EcoRI (Takara Shuzo Co.) and treated with CIAP (calf intestine alkaline phophatase, Takara Shuzo Co.).

(3) Screening of Expression Library by Means of Binding to OCIF

An *escherichia coli* strail, XL2 Blue MRF' (Toyobo Co., Ltd.), was transformed using the DNA produced in Example 8(2) and cultured on L-Carbenisilin agar (1% trypton, 0.5% yeast extract, 1% NaCl, 60 μg/ml carbenisilin, 1.5% agar) prepared in a 24-well plastic plates, to produce about 100 colonies per well. Transformants in each well were suspended in 3 ml of Terrific Broth ampicillin culture medium (1.2% trypton, 2.4% yeast extract, 0.4% glycerol, 0.017 M $KH_2PO_4$, 0.072 M $K_2HPO_4$, 100 μg/ml ampicillin) and cultured at 37° C. overnight with shaking. Cells were collected by centrifugation to prepare plasmid DNA using a QIAwell kit (QIAGEN Co.). DNA concentration was determined by measuring absorbance at 260 nm. DNA was concentrated by precipitating with ethanol and dissolved in distilled water to a concentration of 200 ng/μl. Five hundred DNA pools, each of which was obtained from about 100 colonies were prepared and were used for transfection into COS-7 cells (RIKEN CELL BANK, RCB0539). COS-7 cells were seeded into DMEM containing 10% fetal bovine serum in each well of 24-wel-l plates at a cell density of $8 \times 10^4$ cells/well and cultured overnight at 37° C. in a $CO_2$ incubator. Next day, the culture medium was removed and the cells were washed with serum-free DMEM culture medium. The above-described plasmid DNA which was previously diluted with an OPTI-MEM culture medium (Gibco BRL Co.) and mixed with Lipofectamine (a transfection reagent, manufactured by Gibco BRL Co.) according to the protocol supplied with Lipofectamine. After 15 minutes, the mixture was added to the cells in each well. The amount of Lipofectamine and DNA used were, respectively, 1 µg and 4 µl per well. After 5 hours, the culture medium was removed and 1 ml of DMEM culture medium (Gibco BRL Co.) containing 10% fetal bovine serum was added to each well. The plates were incubated for 2-3 days at 37° C. in a $CO_2$ incubator (5% $CO_2$). The COS-7 cells transfected and cultured for 2-3 days in this manner were washed with a serum-free DMEM culture medium. Then, 200 µl of a culture medium for the binding assay (serum-free DMEM culture medium containing 0.2% calf serum albumin, 20 mM Hepes buffer, 0.1 mg/ml heparin, and 0.02% $NaN_3$) with 20 ng/ml of $^{125}$I-labeled OCIF added thereto was added to each well. After culturing for one hour at 37° C. in a $CO_2$ incubator (5% $CO_2$), the cells were washed twice with 500 µl of a phosphate buffered saline containing 0.1 mg/ml heparin. After washing, 500 µl of 0.1 N NaOH solution was added to each well. The plates were allowed to stand for 10 minutes at room temperature to lyse the cells. The amount of $^{125}$I in each well was measured using a gamma counter (Packard Co.). One DNA pool containing cDNA encoding the protein which specifically binds to OCIF was found by screening a total of 500 pools. The DNA pool containing the cDNA was further divided, and the above-described transfection and screening operations were repeated to isolate the cDNA which encodes the protein which binds to OCIF. The plasmid containing this cDNA was named pOBM291. The *Escherichia coli* containing this plasmid was deposited with The National Institute of Bioscience and Human Technology, Agency of Industrial Science and Technology, Biotechnology Laboratory, as pOBM291 on May 23, 1997 under the deposition No. FERM BP-5953.

The methods of labeling OCIF with $^{125}$I and quantitative analysis of the $^{125}$I-labeled OCIF by ELISA are shown below. Labeling of OCIF with $^{125}$I was carried out according to the Iodogen method. Twenty µl of 25 mg/ml Iodogen-chloroform solution was added to a 1.5 ml Eppendorf tube and chloroform was evaporated by heating at 40° C., to prepare an Iodogen-coated tube. The tube was washed three times with 400 µl of 0.5 M sodium phosphate buffer (Na-Pi, pH 7.0), and 5 µl of 0.5 M Na-Pi (pH 7.0) was added. Immediately after the addition of 1.3 µl (18.5 MBq) of Na—$^{125}$I solution (NEZ-033H20, Amersham Co.), 10 µl of 1 mg/ml rOCIF solution (monomer type or dimer type) was added to the tube. After mixing the contents with a vortex mixer, the tube was allowed to stand at room temperature for 30 seconds. The solution in the tube was transferred to a tube to which 80 µl of 10 mg/ml potassium iodide, 0.5 M Na-Pi (pH 7.0) and 5 µl of a phosphate buffered saline containing 5% bovine serum albumin (BSA-PBS) were previously added. After stirring, the mixture was applied to a spin column (1 ml, G-25 fine, manufactured by Pharmacia Co.) equilibrated with BSA-PBS, and the column was centrifuging for 5 minutes at 2000 rpm. Four hundred µl of BSA-PBS was added to the fraction eluted from the column. After stirring, 2 µl of an aliquot of this solution was sampled to measure the radioactivity by a gamma counter. The radiochemical purity of the $^{125}$I-labeled OCIF solution thus prepared was determined by measuring radioactivity precipitated by 10% TCA. The biological activity of the $^{125}$I-labeled OCIF was measured according to the method of WO 96/26217. The concentration of the $^{125}$I-labeled OCIF was determined by the ELISA as follows. Specifically, 100 µl of 50 mM $NaHCO_3$ (pH 9.6) in which the anti-OCIF rabbit polyclonal antibody described in WO 96/26217 was dissolved to a concentration of 2 µg/ml was added to each well of a 96-well immuno-plate (MaxiSorp™, a product of Nunc Co.). The plate was allowed to stand over night at 4° C. After removing the solution by suction, 300 µl of Block Ace™ (Snow Brand Milk Products Co., Ltd.)/phosphate buffered saline (25/75) (B-PBS) was added to each well. The plate was then allowed to stand for two hours at room temperature. After removing the solution by suction, the wells were washed three times with phosphate buffered saline containing 0.01% Polysorbate 80(P-PBS). Next, 100 µl of B-PBS containing $^{125}$I-labeled OCIF or standard OCIF was added to each well. The plate was then allowed to stand for two hours at room temperature. After removing the solution by suction,, each well was washed six times with 200 µl of P-PBS. One hundred µl of peroxidase-labeled rabbit anti-OCIF polyclonal antibody diluted with B-PBS was added to each well. The plate was allowed to stand for two hours at room temperature. After removing the solution by suction, the wells were washed six times with 200 µl of P-PBS. Then, 100 µl of TMB solution (TMB Soluble Reagent, High Sensitivity, Scytek Co.) was added to each well. After incubating the plate at room temperature for 2-3 minutes, 100 µl of stopping solution (Stopping Reagent, Scytek Co.) was added to each well. Absorbance at 450 nm of each well was measured using a microplate reader. The concentration of $^{125}$I-labeled OCIF was determined based on a calibration curve drawn using the standard preparation of OCIF.

(4) Determination of the Nucleotide Sequence of the cDNA Encoding the Entire Amino Acid Sequence of OBM The nucleotide sequence of the OBM cDNA obtained in the Example 8(3) was determined using a Taq DyeDeoxy Terminator Cycle Sequencing kit (a product of Perkin Elmer Co.). Specifically, the nucleotide sequence of the insert fragment was directly determined using pOBM291 as a template. Fragments with a length of about 1.0 kb and 0.7 kb which were obtained by digesting pOBM291 with a restriction enzyme EcoRI were inserted into the EcoRI site of plasmid-pUCl9 (Takara Shuzo Co.). The nucleotide sequences of these fragments were also determined. The following primers were used: primer SRR2 which was used to determine nucleotide sequences of DNA fragments inserted into pcDL-SR α296, M13PrimerM3 and M13PrimerRV (both manufactured by Takara Shuzo Co.) which were used to determine the nucleotide sequences of DNA fragments inserted into plasmid pUCl9, and synthesized primer OBM#8 designed based on the nucleotide sequence of OBM cDNA. Sequences of these primers are shown as SEQ ID NO:3, SEQ ID NO:4, SEQ ID NO:5, and SEQ ID NO:6.

In addition, the nucleotide sequence of OBM cDNA is shown as SEQ ID NO:2 and the amino acid sequence determined therefrom is shown as the SEQ ID NO:1.

Example 9

Expression of the Protein Encoded by the cDNA of the Present Invention

Plasmid pOBM291 was transfected into COS-7 cells in each well of a 6-well plate using Lipofectamine and the transfected COS-7 cells were cultured for two days in DMEM containing 10% fetal bovine serum. The medium was replaced with a cysteine-methionine-free DMEM (Dainippon Seiyaku Co. Ltd.) (800 μl/well) containing 5% dialyzed fetal bovine serum. The cells were cultured for 15 minutes, followed by the addition of 14 μl of Express Protein Labeling Mix (10 mCi/ml, manufactured by NEN Co.). After culturing for four hours, 200 μl of DMEM including 10% fetal bovine serum was added. After one hour culturing, the cells were washed twice with PBS. Then, 0.5 ml of a TSA buffer (10 mM Tris-HCl (pH 8.0) containing 0.14 M NaCl, 0.025% $NaN_3$), containing 1% TritonX-100, 1% bovine hemoglobin, 10 μg/ml leupeptin, 0.2 TIU/ml aprotinin, 1 mM PMSF, was added and the mixture was allowed to stand for one hour on ice. Cells were disrupted by pipetting and centrifuged at 3000×g for 10 minutes at 4° C. to obtain supernatant. 200 μl of dilution buffer (TSA buffer containing 0.1% TritonX-100, 0.1% bovine hemoglobin, 10 μg/ml leupeptin, 0.2 TIU/ml aprotinin, 1 mM PMSF) was added to 100 μl of this supernatant. The mixture was shaken for one hour at 4° C. with protein A Sepharose (50 μl). The resultant mixture was centrifuged at 1500×g for one minute at 4° C. to collect supernatant, and thereby fraction(s) which is non-specifically adsorbed to Protein A Sepharose was removed. OCIF (1 μg) was added to this supernatant and the mixture was shaken at 4° C. for one hour to achieve the binding of OCIF to OBM. Anti-OCIF polyclonal antibody (50 μg) was added and the mixture was shaken for one hour at 4° C. Then, Protein A Sepharose (10 μl) was added and the mixture was shaken for an additional hour at 4° C., followed by centrifuge at 1500×g for 1 minute at 4° C. to collect precipitate. The precipitate was washed twice with dilution buffer, twice with a bovine hemoglobin-free dilution buffer, once with TSA buffer, and once with 50 mM Tris-HCl (pH 6.5). After washing, SDS buffer (0.125 M Tris-HCl, 4% sodium dodecylsulfate, 20% glycerol, 0.002% Bromophenol Blue, pH 6.8) containing 10% β-mercaptoethanol was added to the precipitate. The mixture was heated for 5 minutes at 100° C. and subjected to SDS-PAGE (12.5% polyacrylamide gel, Daiichi Chemical Co., Ltd.). The gel was fixed according to a conventional method. Isotope signals were amplified using Amplify™ (Amersham Co.) and the sample was exposed to Bio Max MR film (KODAK Co.) at −80° C. The results are shown in FIG. 8, which indicates that the protein encoded by the cDNA of the present invention has a molecular weight of about 40,000.

Example 10

Binding of the Protein Encoded by the cDNA of the Present Invention to OCIF

Plasmid pOBM291 was transfected into COS cells in each well of a 24-well plate using Lipofectamine. After culturing for 2-3 days, the cells were washed with serum-free DMEM culture medium. 200 μl of culture medium for the binding assay (serum-free DMEM culture medium containing 0.2% calf serum, albumin, 20 mM Hepes, 0.1 mg/ml heparin, and 0.2% $NaN_3$), supplemented with 20 ng/ml $^{125}$I-labeled OCIF, was added to the wells. To the other wells, 200 μl of culture medium for the binding assay to which 8 μg/ml of unlabelled OCIF had been added, in addition to 20 ng/ml $^{125}$I-labeled OCIF, was added. After culturing for one hour at 37° C. in a $CO_2$ incubator (5% $CO_2$), the cells were washed twice with 500 μl of phosphate buffered saline containing 0.1 mg/ml of heparin. Then, 500 μl of 0.1 N NaOH solution was added to each well and the plate was allowed to stand for 10 minutes at room temperature to dissolve the cells. The amount of $^{125}$I in each well was measured by a gamma counter. As a result, as shown in FIG. 9, the $^{125}$I-labeled OCIF was found to bind only to the cells in which plasmid pOBM291 was transfected. In addition, the binding was confirmed to be conspicuously inhibited by the addition of (unlabeled) OCIF at a 400-fold concentration. These results have demonstrated that the protein OBM encoded by the cDNA on plasmid pOBM291 specifically binds to OCIF on the surface of the transfected COS-7 cells.

Example 11

Crosslinking of $^{125}$I-labeled OCIF and the Protein Encoded by the cDNA of the Present Invention Crosslinking of $^{125}$I-labeled monomer type OCIF and the protein encoded by the cDNA of the present invention was carried out to investigate the characteristics of the protein encoded by the cDNA of the present invention in further detail. After transfection of plasmid pOBM291 into COS-7 cells according to the method used in the Example 8(3), 200 μl of the culture medium for the binding assay, as described above, containing $^{125}$I-labeled OCIF (25 ng/ml) was added to the wells. The culture medium for the binding assay to which unlabeled OCIF at a 400-fold concentration was added in addition to $^{125}$I-labeled OCIF was added to the other wells. After culturing for one hour at 37° C. in a $CO_2$ incubator (5% $CO_2$), the cells were washed twice with 500 μl of phosphate buffered saline containing 0.1 mg/ml heparin. Five hundred μl of phosphate buffered saline containing 100 μg/ml of a crosslinking agent, DSS (disuccinimidyl suberate, manufactured by Pierce Co.) was added to the cells, followed by a reaction for 10 minutes at 0° C. The cells in these wells were washed twice with 1 ml of cold phosphate buffered saline (0° C.). After the addition of 100 μl of 20 mM Hepes buffer containing 1% Triton X-100 (Wako Pure Chemicals Co., Ltd.), 2 mM PMSF (Phenylmethylsulfonyl fluoride, Sigma Co.), 10 μM Pepstatin (Wako Pure Chemicals Co., Ltd.), 10 μM Leupeptin (Wako Pure Chemicals Co., Ltd.), 10 μM antipain (Wako Pure Chemicals Co., Ltd.) and 2 mM EDTA (Wako Pure Chemicals Co., Ltd.), the wells were allowed to stand for 30 minutes at room temperature to dissolve the cells. Fifteen μl aliquots of these samples were heated in the presence of SDS under reducing conditions according to a conventional method and subjected to SDS-electrophoresis using 4-20% polyacrylamide gradient gel (Daiichi Pure Chemical Co., Ltd.). After the electrophoresis, the gel was dried and exposed for 24 hours at −80° C. to a BioMax MS film (Kodak Co.) using a BioMax MS sensitization screen (Kodak Co.). The exposed film was developed according to a conventional method. As a result, a band with a molecular weight of a range of 90,000-110,000, shown in FIG. 10, was detected by crosslinking the $^{125}$I-labeled monomer type OCIF and the protein encoded by the cDNA of the present invention.

Example 12

Northern Blotting Analysis

ST2 cells cultured to become confluent in a 25 $cm^2$ T flask for attached-cell cultures were treated with trypsin and stripped from the T flask. After washing, the cells were seeded into a 225 $cm^2$ T flask and cultured for 4 days in a $CO_2$ incubator with 60 ml of an α-MEM culture medium containing $10^{-8}$ M active-form vitamin $D_3$, $10^{-7}$ M dexamethasone, and 10% fetal bovine serum. Total RNA was extracted from the cultured ST2 cells using ISOGEN (Wako Pure Chemicals Co., Ltd.). The total RNA was also extracted in the same manner from ST2 cells which were cultured in the absence of the active-form vitamin $D_3$ and dexamethasone. After the addition of 2.0 μl of 5× gel electrophoresis buffer solution (0.2 M morpholino propane sulfonic acid, pH 7.0, 50 mM sodium acetate, 5 mM EDTA) and 3.5 μl of formaldehyde, and 10.0 μl of formamide to 20 μg (4.5 μl) of each of the total RNAs, the mixtures were incubated for 15 minutes at 55° C. and subjected to electrophoresis. The gel for electrophoresis was prepared according to the formulation of 1.0% agarose, 2.2 M deionized formaldehyde, 40 mM morpholinopropane sulfonic acid (pH 7.0), 10 mM sodium acetate, and 1 mM EDTA. The electrophoresis was carried out in a buffer solution of 40 mM morpholino propane sulfonic acid, pH 7.0, 10 mM sodium acetate, and 1 mM EDTA. After the electrophoresis, RNA was transferred onto nylon membrane. About 1.0 kb DNA fragment was obtained by digesting pOBM291 with a restriction enzyme, EcoRI. Hybridization was carried out using this DNA fragment, labeled with a Megaprime DNA labeling kit (Amersham Co.) and $\alpha\text{-}^{32}$p-dCTP (Amersham Co.), as a probe. As a result, as shown in FIG. 11, it was confirmed that when ST2 cells were cultured in the presence of active-form vitamin $D_3$ and dexamethasone, gene expression of the protein encoded by the cDNA of the present invention (OBM) is induced strongly.

Example 13

Osteoclasts Formation Supporting Capability of the Protein encoded by the cDNA of the Present Invention pOBM291 was transfected into COS cells according to the same method described in the Example 8(3). After three days, trypsinized cells were washed once with phosphate buffered saline solution by centrifugation, then fixed with PBS containing 1% paraformaldehyde at room temperature for 5 minutes, followed by washing with PBS six times by centrifugation. 700 μl of $1\times10^6$/ml mouse spleen cells and 350 μl of $4\times10^4$/ml ST2 cells which were suspended in α-MEM culture medium containing $10^{-8}$ M active-form vitamin $D_3$, $10^{-7}$ M dexamethasone, and 10% fetal bovine serum, were added to a 24-well plate. TC insert (Nunc Co.) was set in each well. The above-described fixed COS cells (350 μl) diluted to various concentrations with the above-mentioned culture medium and OCIF solution (50 μl) were added to the TC insert and cultured for 6 days at 37° C. As a result, it was confirmed that the osteoclasts formation inhibitive activity of OCIF can be inhibited by the protein encoded by the cDNA of the present invention.

Example 14

Expression of Secreted-form OBM (1) Construction of a Plasmid for the Expression of Secreted-form OBM A PCR reaction was carried out using OBM HF (SEQ ID No:7) and OBM XR (SEQ ID NO:8) as primers and pOBM291 as a template. After purification by agarose gel electrophoresis, the product was digested with restriction enzymes HindIII and EcoRI, and further purified by agarose gel electrophoresis. The purified fragment (0.6 kb), Hind III/EcoRI fragment (5.2 kb) of pSec TagA (Invitrogen Co.), and EcoRI/PmacI fragment (0.32 kb) of OBM cDNA were ligated using a ligation kit ver. 2 (Takara Shuzo Co.). *Escherichia coli* DH5α was transformed using the reaction product. Plasmids were purified by means of alkali SDS method from the resulting ampicillin resistant strains and digested with restriction enzymes to select a plasmid with fragments of a length of 0.6 Kb and 0.32 kb being inserted into pSec TagA. Selected plasmid was identified as having a sequence encoding the secreted-form OBM (nucleotide sequence: 338-1355 in SEQ ID NO:2, amino acid sequence: 72-316 in the SEQ ID NO:1) by sequencing using a dyeterminator cycle sequencing FS kit (Perkin Elmer Co.). This plasmid was digested with restriction enzymes NheI and XhoI to isolate a fragment (1.0 kb) containing the secreted-form OBM cDNA by agarose gel electrophoresis. This fragment was inserted into the NheI/XhoI fragment (10.4 kb) of an expression vector, pCEP4 (Invitrogen Co.), using a ligation kit and *Escherichia coli* DH5 α was transformed using the reaction product thereof. Plasmids were purified by alkali SDS method from the resulting ampicillin resistant strains and digested with restriction enzymes to select an *Escherichia coli* strain having the secreted-form OBM expression plasmid (pCEP sOBM) with the correct structure. The *Escherichia coli* strain containing the pCEP SOBM was cultured and pCEP sOBM was purified using QIA™ filter plasmid midi kit (QIAGEN Co.).

(2) Expression of Secreted-form OBM

293-EBNA cells were suspended in IMDM containing 10% FCS (IMDM-10% FCS)and seeded into a 24-well plate coated with collagen (manufactured by Sumitomo Bakelite Co., Ltd.) in a cell density of $2\times10^5$/2 ml/well and cultured overnight. The cells were transfected with 1 μg of pCEP sOBM or pCEP4 using 4 μl of Lipofectamine (Gibco Co.). After culturing for two days in 0.5 ml of a serum-free IMDM or IMDM-10% FCS, the conditioned medium was collected. Expression of the secreted-form OBM in the conditioned medium was confirmed as follows. Sodium hydrogen carbonate was added to the conditioned medium to a final concentration of 0.1 M and the solution was added to a 96-well plate. The plate was allowed to stand overnight at 40° C., thereby immobilizing OBM in the conditioned medium on the 96-well plate. The plate was filled with a Block Ace™ (Snow Brand Milk Products Co., Ltd.) solution diluted four-fold with PBS (B-PBS) and allowed to stand for two hours at room temperature to block residual binding sites of the plate. After the addition to each well of 100 μl of 3-100 ng/ml of OCIF which was diluted with B-PBS, the plate was allowed to stand for two hours at 37° C., followed by washing with PBS containing 0.05% Tween 20(PBS-T). Then, 100 μl of a peroxidase-labeled rabbit anti-OCIF polyclonal antibody described in WO 96/26217 which was diluted with B-PBS was added to each well. After allowing to stand for two hours at 37° C., the wells were washed six times with PBS-T. Then, a TMB solution (TMB Soluble Reagent, High Sensitivity, Scytek Co.) was added in the amount of 100 μl per well and allowed to stand at room temperature for about 10 minutes, whereupon the reaction was terminated by the addition of 100 μl of a termination solution (Stopping Reagent, Scytek Co.) to each well. Absorbance at 450 nm of each well was measured by a microplate reader. The results are shown in FIG. 12 which indicates that the absorbance at 450 nm increased according to the concentration of the added OCIF in the plate in which the conditioned medium of the cells transfected with pCEP sOBM was immobilized. On the other hand, no increase in absorbance was seen in the plate in which the conditioned medium of the cells transfected with vector pCEP4 was immobilized. FIG. 13 shows the results of an experiment wherein the proportion of the conditioned medium which is used for immobilization was changed within a range of 5-90% and a specific concentration of OCIF (50 ng/ml) was added. It can be seen that the absorbance at 450 nm increased according to the increase in the proportion of the conditioned medium in the plate wherein the conditioned medium of the cells transfected with pCEPsOBM was immobilized, whereas no such increase in absorbance was seen in the plate wherein the conditioned medium of the cells transfected with vector pCEP4 was immobilized. From these results, it was confirmed that secreted-form OBM is produced into the conditioned medium of the cells transfected with pCBP sOBM.

Example 15

Expression of Thioredoxin-OBM Fusion Protein (Trx-OBM)

(1) Construction of a Thioredoxin-OBM Fusion Protein (Trx-OBM) Expression Vector Ten μl of 10× ExTaq buffer (Takara Shuzo Co.), 8 μl of 10 mM dNTP (Takara Shuzo Co.), 77.5 μl of sterilized distilled water, 2 μl of an aqueous solution of pOBM291 (10 ng/μl), 1 μl of primer OBM3 (100 pmol/μl, SEQ ID NO:9), 1 μl of primer OBMSalR2 (100 pmol/μl, SEQ ID NO:10), and 0.5 μl of ExTaq (5 u/μl) (Takara Shuzo Co.) were mixed and reacted (PCR reaction) in a micro centrifuge tube. After reacting at 95° C. for 5 minutes, at 50° C. for one second, at 55° C. for one minute, at 74° C. for one second, and at 72° C. for 5 minutes, a cycle reaction consisting of a reaction at 96° C. for one minute, at 50° C. for one second, at 55° C. for one minute, at 74° C. for one second, and at 72° C. for 3 minutes, was repeated 25 times. From the total reaction liquid DNA fragment of about 750 bp was purified by 1% agarose gel electrophoresis using QIAEX™ II gel extraction kit (QIAGEN Co.). The whole amount of purified DNA fragment was digested with restriction enzymes SalI and EcoRI (Takara Shuzo Co.) and subjected to an 1.5% agarose gel electrophoresis to purify a DNA fragment of about 160 bp (Fragment 1), which was dissolved in 20 μl of sterilized distilled water. In the same manner, a DNA fragment of about 580 bp (Fragment 2) obtained by digesting 4 μg of pOBM291 with restriction enzymes BamH1 and EcoRI (Takara Shuzo Co.) and a DNA fragment of about 3.6 kb (Fragment 3) obtained by digesting 2 μg of pTrXFus (Invitrogen Co.) with restriction enzymes BamHI and SalI (Takara Shuzo Co.) were respectively purified and dissolved in 20 μl of sterilized distilled water. The QIAEXII gel extraction kit was used for the purification of DNA fragments. Fragments 1-3 were ligated by incubating at 16° C. for 2.5 hours using DNA ligation kit ver.2 (Takara Shuzo Co.). Using the ligation reaction liquid, *Escherichia coli* strain GI724 (Invirogen Co.) was transformed according to the method described in the Instruction Manual of ThioFusion Expression System (Invirogen Co.). A microorganism strain with plasmid in which the OBM cDNA fragment (nucleotide sequence: 350-1111 in the SEQ ID NO:2, amino acid sequence: 76-316 in the SEQ ID NO:1) is fused in frame to a thioredoxin gene was selected from the resulting ampicillin resistant transformants by the analysis of restriction maps obtained by digestion with restriction enzymes and DNA sequence determination. The microorganism strain thus obtained was named GI724/pTrxOBM25.

(2) Expression of OBM in *Escherichia coli*

GI724/pTrxOBM25 and GI724 containing pTrxFus (GI724/pTrxFus) were respectively cultured six hours with shaking at 30° C. in 2 ml of RMG-Amp culture medium (0.6% $Na_2HPO_4$, 0.3% $KH_2PO_4$, 0.05% NaCl, 0.1% $NH_4Cl$, 1.2% casamino acid (Difco Co.), 1% glycerol, 1 mM $MgCl_2$, and 100 μg/ml ampicillin (Sigma Co.), pH 7.4). The broth 0.5 ml of the broth was added to 50 ml of Induction culture medium (0.6% $Na_2HPO_4$, 0.3% $KH_2PO_4$, 0.05% NaCl, 0.1% $NH_4Cl$, 0.2% casamino acid, 0.5% glucose, 1 mM $MgCl_2$, 100 μg/ml ampicillin, pH 7.4) and cultured with shaking at 30° C. When $OD_{600nm}$ reached about 0.5, L-tryptophan was added to a final concentration of 0.1 mg/ml, followed by shaking the culture at 30° C. for an additional 6 hours. The culture broth was centrifuged at 3000×g to collect the cells, which were suspended in 12.5 ml of PBS (10 mM phosphate buffer, 0.15 M NaCl, pH 7.4). The suspension was subjected to an ultrasonic generator (Ultrasonics Co.) to disrupt the cells. The disrupted cells were centrifuged at 7000×g for 30 minutes to obtain a supernatant liquid as a soluble protein fraction. Ten μl of this soluble protein fraction was subjected to SDS polyacrylamide (10%) electrophoresis under reducing conditions. As a result, a band with a molecular weight of 40 kDa which was not detected in the soluble protein fraction of GI724/pTrxFus was found in the soluble protein fraction of GI724/pTrxOBM25 (FIG. 14). Accordingly, it was confirmed that a fusion protein (Trx-OBM) of thioredoxin and OBM was expressed in *Escherichia coli*.

(3) Binding Capability of Trx-OBM to OCIF

Binding of the expressed Trx-OBM to OCIF was confirmed according to the following experiment. Anti-thioredoxin antibody (Invirogen Co.) which was diluted to 5000-fold with 10 mM sodium hydrogen carbonate solution was added to a 96-well immunoplate (Nunc Co.) in the amount of 100 μl per well. After being allowed to stand overnight at 4° C., the liquid in the wells was discarded. Two hundred μl of a solution prepared by diluting BlockAce™ (Snow Brand Milk Products Co., Ltd.) two-fold with PBS (BA-PBS) was added to each well. After being allowed to stand for one hour at room temperature, the solution was discarded and soluble protein fractions originating from the above-described GI724/pTrxOBM25 or GI724/pTrxFus, each diluted with BA-PBS in various concentrations were added to each well in the amount of 100 μl. After being allowed to stand for two hours at room temperature, each well was washed three times with PBS-T and charged with 100 μl of OCIF (100 ng/ml) which was diluted with BA-PBS. After being allowed to stand for two hours at room temperature, each well was washed three times with PBS-T and charged with 100 μl of peroxidase-labeled rabbit anti-OCIF polyclonal antibody (described in WO 96/26217) which was diluted 2,000-fold with BA-PBS. After being allowed to stand for two hours at room temperature, each well was washed six times with PBS-T and charged with 100 μl of TMB solution (TMB Soluble Reagent, High Sensitivity, Scytek Co.). After being allowed to stand for about 10 minutes at room temperature, each well was charged with 100 μl of termination solution (Stopping Reagent, Scytek Co.). Absorbance of each well at 450 nm was measured by a microplate reader. The results are shown in FIG. 15. There was no difference in absorbance between the sample with the soluble protein fraction originating from GI724/pTrxFus added thereto and the sample without the addition of this soluble protein fraction. On the other hand, the absorbance increased in the samples to which the soluble protein fraction originating from GI724/pTrxOBM25 was added in proportion to the concentration of the soluble protein fraction. The results of the other experiment wherein the dilution rate of the soluble protein fraction was maintained constant (1%) while adding OCIF diluted with BA-PBS in different concentrations (0-100 ng/ml) are shown in FIG. 16. It can be seen that the absorbance remained low at any concentrations of OCIF in samples using a soluble protein fraction originating from GI724/pTrxFus, whereas the absorbance increased in proportion to the OCIF concentration in the samples to which the soluble protein fraction originating from GI724/pTrxOBM25 was added. Based on these results, it was confirmed that Trx-OBM which is produced from GI724/pTrxOBM25 has a capability of binding to OCIF.

(4) Large-scale Cultivation of *Escherichia coli* which Produces Trx-OBM

GI724/pTrxOBM25 cells were spread on RMG-Amp agar (0.6% $Na_2PO_4$, 0.3% $KH_2PO_4$, 0.05% NaCl, 0.1% $NH_4Cl$, 2% casamino acid, 1% glycerol, 1 mM $MgCl_2$, 100 μg/ml ampicillin, 1.5% agar, pH 7.4) using a platinum transfer loop. The cells were cultured overnight at 30° C. The cultured cells were suspended in 10 ml of Induction medium. The suspension was added 5 ml for each to two 2 l Erlenmeyer flasks containing 500 ml of Induction medium and cultured at 30° C. with shaking. When the $OD_{600nm}$ reached about 0.5, L-tryptophan was added to a final concentration of 0.1 mg/ml. Culturing with shaking was continued for six hours at 30° C. The culture broth was centrifuged for 20 minutes at 3000×g to collect the cells, which were suspended in 160 ml of PBS. The suspension was subjected to an ultrasonic generator (Ultrasonics Co.) to disrupt the cells. The supernatant liquid was centrifuged for 30 minutes at 7000×g to obtain a soluble protein fraction.

(5) Preparation of OCIF-immobilized Affinity Column

Two g of TSKgel AF-Tolesyl Toyopal 650 (Tosoh Corp.) and 40 ml of 1.0 M potassium phosphate buffer (pH 7.5) containing 35.0 mg of recombinant OCIF, which was prepared according to the method described in WO 96/26217, were mixed. The mixture was gently shaken overnight at 4° C. to effect a coupling reaction. The reaction mixture was centrifuged to remove the supernatant. To inactivate excess active residues, 40 ml of 0.1 M Tris-HCl buffer (pH 7.5) was added to the precipitated carrier and the mixture was gently shaken at room temperature for one hour. The carrier in a column was washed with 0.1 M glycine-HCl buffer (pH 3.3) containing 0.01% Polysorbate 80 and 0.2 M NaCl and 0.1 M sodium citrate buffer (pH 2.0) containing 0.01% Polysorbate 80 and 0.2 M NaCl. The carrier in the column was equilibrated by charging twice with 10 mM sodium phosphate buffer (pH 7.4) containing 0.01% Polysorbate 80.

(6) Purification of Trx-OBM Using OCIF-immobilized Affinity Column

Unless otherwise indicated, purification of Trx-OBM was carried out at 4° C. The above-mentioned OCIF-immobilized affinity carrier (10 ml) and the soluble protein fraction (120 ml) prepared in Example 15(4) were mixed. The mixture was gently shaken overnight at 4° C. in four 50-ml centrifuge tubes using a rotor. An Econo-column™ (internal diameter: 1.5 cm, length: 15 cm, manufactured by BioRad Co.) was filled with the carrier in the mixture. The column was charged with 300 ml of PBS containing 0.01% Polysorbate 80, 100 ml of 10 mM sodium phosphate buffer (pH 7.0) containing 0.01% Polysorbate 80 and 2 M NaCl, and 100 ml of 0.1 M glycine-HCl buffer (pH 3.3) containing 0.01% Polysorbate 80 and 0.2 M NaCl, in that order. Next, proteins adsorbed in the column were eluted with 0.1 M sodium citrate buffer (pH 2.0) containing 0.01% Polysorbate 80 and 0.2 M NaCl. The eluate was collected in 5 ml portions. Each fraction thus collected was immediately neutralized with addition 10% volume of 2 M Tris buffer (pH 8.0). Presence or absence of Trx-OBM in the eluted fractions was determined according to the method previously described in Example 15(3) (the binding capability to OCIF). The fractions containing Trx-OBM were collected and purified further.

(7) Purification of Trx-OBM by Gel Filtration

About 25 ml of Trx-OBM fractions obtained in Example 15 (6) was concentrated to about 0.5 ml by centrifuge using Centriplus 10 and Centricon 10 (Amicon Co.). This sample was applied to a Superose 12 HR 10/30 column (1.0×30 cm, Pharmacia Co.) previously equilibrated with PBS containing 0.01% Polysorbate 80. For the separation, PBS containing 0.01% Polysorbate 80 was used as a mobile phase at a flow rate of 0.25 ml/min. The eluate from the column was collected in 0.25 ml portions. The Trx-OBM in the thus-collected fractions was detected by the same method as previously described in Example 15(3) and by SDS-polyacrylamide electrophoresis (10-15% polyacrylamide gel, Pharmacia Co.) using Phast System (Pharmacia Co.) and silver staining. Fractions (Fr. 20-23) containing purified Trx-OBM were collected and the protein concentration of Trx-OBM was determined. The measurement of the protein concentration was carried out using bovine serum albumin as a standard substance using DC-Protein assay kit (BioRad Co.).

Example 16

Osteoclast Formation-inducing Activity of OBM pOBM291 and pcDL-SR α296 were respectively transfected into COS-7 cells using Lipofectamine (Gibco Co.). The cells were cultured in DMEM containing 10% FCS for one day, trypsinized, plated on cover slips(15 mm round shape, manufactured by Matsunami Co.) in 24-well plates at $5×10^4$ cells per well, and cultured for 2 days. The culture plate was washed once with PBS. The cells were fixed with PBS containing 1% paraformaldehyde at room temperature for 8 minutes. The plate on which the fixed cells were attached was washed 6 times with PBS, then 700 μl of mouse spleen cells suspended at $1×10^6$/ml in α-MEM containing $10^{-8}$ M activeform vitamin $D_3$, $10^{-7}$ M dexamethasone, and 10% fetal bovine serum were added to each well. Millicell PCF (Millipore Co.) was set in each well and a suspension of ST2 cells in the above-mentioned culture medium ($4×10^4$/ml) were added, 700 μl per well, into the Millicell PCF followed by incubation at 37° C. for 6 days. After the culture, the Millicell PCF was removed, the plate was washed once with PBS, and the cells were fixed with acetone-ethanol solution (50:50) for one minute. Then, cells exhibiting tartaric acid-resistant acid phophatase activity (TRAP), which is a specific marker for osteoclast, were selectively stained using LEUKOCYTE ACID PHOSPHATASE kit (Sigma Co.). As a result of microscopic observation, TRAP-positive cells were not detected in the wells in which COS-7 cells transfected with pcDL-SR α296 were fixed. In contrast, 45±18 (average±standard deviation, n=3) TRAP positive cells were observed in the wells in which COS-7 cells transfected with pOBM291 were fixed. Moreover, it was also confirmed that calcitonin bound to these TRAP positive cells. Based on these findings, it has been proven that OBM has osteoclast formation-inducing activity.

Example 17

Osteoclast Formation-inducing Activity of Trx-OBM and Secreted-form OBM

Mouse spleen cells were suspended in α-MEM containing $10^{-8}$ M active-form vitamin $D_3$, $10^{-7}$ M dexamethasone, and 10% fetal bovine serum at a concentration of 2×10⁶/ml. The suspension was added to a 24 well plate in the amount of 350 µl per well. Each well was then charged with 350 µl of a solution prepared by diluting purified Trx-OBM with the above-mentioned culture medium (40 ng/ml), 350 µl of solution prepared by 10-fold diluting conditioned medium which was produced by culturing 293-EBNA cells, in which PCEP sOBM or pCEP4 were transfected, in IMDM-10% FCS, with the above-mentioned culture medium, or 350 µl only of the above-mentioned culture medium. The Millicell PCF (Mollipore Co.) was set on each well, to which 600 µl of ST2 cells which was suspended in the above-mentioned culture medium (4×10⁴/ml) were added. After cultured for six days, Millicell PCF was removed. The plate was washed once with PBS and the cells were fixed with acetone-ethanol solution (50:50) for one minute. Then, the cells exhibiting the tartaric acid resistant acidic phophatase activity (TRAP activity) were selectively stained using LEUKOCYTE ACID PHOSPHATASE kit (Sigma Co.). The result of microscopic observation revealed that no cells exhibiting the TRAP activity were detected in the wells to which no Trx-OBM was added, whereas 106±21 (average±standard deviation, n=3) TRAP-positive cells were observed in the wells to which Trx-OBM was added. Similarly, while no cells exhibiting TRAP activity were detected in the wells to which conditioned medium of 293-EBNA transfected with pCEP4 had been added, 120±31 (average±standard deviation, n=3) TRAP positive cells were observed in the wells to which conditioned medium of 293-EBNA transfected with pCEPsOBM had been added. Moreover, it was also confirmed that calcitonin binds to these TRAP positive cells. These results have proven that Trx-OBM and secreted-form OBM exhibit osteoclast formation-inducing activity.

Example 18

Identity of the Protein OBM Expressed by the cDNA of the Present Invention and the Natural Type OCIF-binding Protein of the Present Invention (1) Preparation of Rabbit Anti-OBM Polyclonal Antibody Three male Japanese white rabbits (weight: 2.5-3.0 kg, supplied by Kitayama Labes Co.) were immunized with the purified OBM (thioredoxin-OBM fusion protein) produced according to the method in Examples 14(6) and 14(7) by subcutaneously injecting 1 ml/dose of emulsion prepared by mixing 200 µg/ml of the purified OBM with equal volume of Freund's complete adjuvant (DIFCO Co.), six times, once a week. Ten days after the last immunization, the rabbits were exsanguinated. Antibody was purified from the serum as follows. Ammonium sulfate was added to the antiserum which was diluted two-fold with PBS to a final concentration of 40% (w/v%). After being allowed to stand for one hour at 4° C., the mixture was centrifuged for 20 minutes at 8000×g to obtain a precipitate. The precipitate was dissolved in a small amount of PBS, dialyzed against PBS at 4° C., and loaded to a Protein G-Sepharose column (manufactured by Pharmacia Co.) After washed with PBS, the adsorbed immunoglobulin G was eluted with 0.1 M glycine-HCl buffer solution (pH 3.0). The eluate was immediately neutralized with 1.5 M Tris-HCl buffer (pH 8.7). After dialyzing the eluted protein fractions against PBS, the absorbance at 280 nm was measured to determine the protein concentration ($E^{1\%}$ 13.5). Anti-OBM antibody labeled with horseradish peroxidase was prepared using a maleimide-activated paroxidase kit (Pierce Co.) as follows. 80 µg of N-succinimide-S-acetyl thioacetic acid was added to 1 mg of the purified antibody and reacted at room temperature for 30 minutes. Five mg of hydroxylamine was added to the resulting mixture to deacetylate the antibody. The modified antibody was fractionated using a polyacrylamide desalting column. The protein fractions were mixed with 1 mg of maleimide-activated peroxidase and reacted for one hour at room temperature to obtain enzyme-labeled antibody.

(2) Capability of Rabbit Anti-OBM Polyclonal Antibody to Inhibit Specific Binding of the Protein (OBM) Expressed by the cDNA of the Present Invention or the Natural Type Protein of the Present Invention with OCIF Purified OBM (thioredoxin-OBM fused protein) obtained according to the method described in the Examples 15(6) and 15(7) and the natural type purified OCIF-binding protein of the Example 2(4) were dissolved respectively in 0.1 M sodium carbonate buffer to a concentration of 2 µg/ml. An aliquot of each solution was added 100 µl per well respectively to a 96-well immunoplate (manufactured by Nunc Co.). The plate was allowed to stand overnight at 4° C. 200 µl of 50% Block Ace was added to each well and the plate was allowed to stand at room temperature for one hour. After washing each well three times with PBS containing 0.1% Polysolbate 20 (P20-PBS), 100 µl of rabbit anti-OBM antibody solution which was dissolved in 25% Block Ace prepared with P20-PBS to a concentration of 200 µg/ml or 100 µl of 25% Block Ace (containing no antibody) was added to each well, followed by incubation at 37° C. for one hour. Each well was washed three times with P20-PBS and charged with 100 µl/well of a binding test solution (P20-PBS containing 0.2%.calf serum albumin, 20 mM Hepes, and 0.1 mg/ml heparin) to which 20 ng/ml of $^{125}$I-labeled OCIF described in the Example 8(3) was added. Alternatively, each well was charged with 100 µl/well of another binding test solution containing 8 µg/ml of unlabeled OCIF in addition to 20 ng/ml $^{125}$I-labeled OCIF. After incubating these immunoplates at 37° C. for one hour, the wells were washed with P20-PBS six times. The amount of $^{125}$I in each well was measured by a gamma counter. The results are shown in FIG. 17. As shown in the figure, both the purified OBM expressed using the cDNA of the present invention and the protein that specifically bind the natural type OCIF-specifically binding protein of the present invention do not bind to the $^{125}$I-labeled OCIF at all, when they were treated with the rabbit anti-OBM polyclonal antibody, whereas both proteins bound $^{125}$I-labeled OCIF when untreated with the antibody. The binding of both proteins to $^{125}$I-labeled OCIF was confirmed to be clearly specific, because those bindings are significantly inhibited by the addition of 400-fold concentration of unlabelled OCIF (8 µg/ml). Based on the results described above, the rabbit anti-OBM polyclonal antibody recognizes both the OBM which is the protein expressed using the cDNA of the present invention and the natural-type OCIF-binding protein of the present invention, and it inhibits the specific binding of these proteins with OCIF.

Example 19

Cloning of Human OBM cDNA (1) Preparation of Mouse OBM Primer

The mouse OBM primers prepared according to the method of the Examples (OBM#3 and OBM#8) described above, were used for screening of human OBM cDNA. The sequences are shown in the SEQ ID NO: 9 and SEQ ID NO:6, respectively.

(2) Isolation of Human OBM cDNA Fragment by PCR

Human OBM cDNA fragments were obtained by PCR using the mouse OBM cDNA primers prepared in (1) above and Human Lymph Node Marathon ready cDNA (Clontech Co.) as a template. The conditions for PCR were shown as follows:

| | |
|---|---|
| 10 × EX Taq buffer (Takara Shuzo Co.) | 2 µl |
| 2.5 mM dNTP | 1.6 µl |
| cDNA solution | 1 µl |
| EX Taq (Takara Shuzo Co.) | 0.2 µl |
| Distilled water | 14.8 µl |
| 40 µM primer OBM#3 | 0.2 µl |
| 40 µM primer OBM#8 | 0.2 µl |

These solutions were mixed in a microfuge tube and pre-incubated at 95° C. for 2 minutes, followed by 40 cycles of a three-stage reaction consisted of reactions at 95° C. for 30 seconds, at 57° C. for 30 seconds, and at 72° C. for 2.5 minutes. After the reaction, the solution was incubated for 5 minutes at 72° C. and a portion of the solution was subjected to electrophoresis on an agarose gel. A DNA fragment (about 690 bp) amplified by the mouse OBM cDNA primers described above was detected.

(3) Purification of the Human OBM cDNA Fragment Amplified by PCR and Determination of the Nucleotide Sequence The human OBM cDNA fragment obtained in Example 19 (2) was separated by electrophoresis on an agarose gel and further purified using a QIAEX gel extraction kit (Qiagen Co.). PCR was again performed using the purified human OBM cDNA fragment as a template and the mouse OBM cDNA primers described above, to produce a large quantity of the human OBM cDNA fragment. The DNA fragment was purified by a QIAEX gel extraction kit in the same manner as above. The nucleotide sequence of the purified human OBM cDNA fragment was determined using a Taq Dye Deoxy Terminator Cycle Sequencing FS kit (Perkin Elmer Co.) using OBM#3 or OBM#8 SEQ ID NO: 9 and SEQ ID NO: 6 , respectively) as a primer. When compared with the sequence of corresponding area of the mouse OBM cDNA, the nucleotide sequence of the human OBM cDNA fragment showed 80.7% homology with that of the mouse OBM cDNA.

(4) Screening of a Full-length Human OBM cDNA by Hybridization Using the Human OBM cDNA Fragment (About 690bp) as a Probe A full-length human OBM cDNA was screened using the human OBM cDNA fragment (about 690 bp) that was purified in the Example 19(3) and labeled with [$\alpha^{32}$p] dCTP using a Megaprime DNA Labeling kit (Amersham Co.). Human Lymph Node 5'-STRETCH PLUS cDNA library (Clontech Co., the U.S.A) was screened using the DNA probe. According to the manufacturer's protocol, *Escherichia coli* C600 Hfl was infected with the recombinant phage for 15 minutes at 37° C. The infected *Escherichia coli* was added to an LB agar (1% trypton, 0.5% yeast extract, 1% NaCl, 0.7% agar) which was heated at 45° C. The LB agar was poured onto an LB agar plate containing 1.5% agar. After overnight incubation at 37° C., HyBond-N™ (Amersham Co.) was placed to the plate on which plaques were produced and stored for about 3 minutes. According to a conventional method, the filter was treated with alkaline solution, neutralized, and dipped in 2×SSC solution. DNA was then immobilized onto the filter using the UV CROSSLINKER (Stratagene Co.). The resulting filter was dipped into Rapid-hyb buffer (Amersham Co.). After pretreatment for 15 minutes at 65° C., the filter was placed in Rapid-hyb buffer containing the heat-denatured human OBM cDNA fragment (about 690 bp, 5×10⁵ cpm/ml) described above. After overnight hybridization at 65° C., the filter was washed with 2×SSC, 1×SSC, and 0.1×SSC, each containing 0.1% SDS, in this order respectively for 15 minutes at 65° C. Several positive clones obtained were further purified by repeating the screening twice. A clone possessing an insert (about 2.2 kb) was selected from the purified clones and was used in the following experiments. This purified phage was named λhOBM. About 10 µg of DNA was obtained from the purified λhOBM using a QIAGEN Lambda kit (Qiagen Co.) according to the manufacturer's protocol. The DNA was digested with restriction enzyme SaII and subjected to electrophoresis on an agarose gel to separate the hOBM insert cDNA(about 2.2 kb). This DNA fragment purified using the QIAEX gel extraction kit (Qiagen Co.) was digested with restriction enzyme SaII and inserted into plasmid pUC19 (MBI Co.) which was previously digested with a restriction enzyme SaII and dephosphorylated, using a DNA ligation kit ver. 2 (Takara Shuzo Co.). *Escherichia coli* DH 5α (Gibco BRL Co.) was transformed with the pUC19 containing the resulting DNA fragment. The resulting transformant was named pUC19hOBM. The transformant was grown and pUC19hOBM in which the human OBM cDNA (about 2.2 kb) was inserted and purified by a conventional method.

(5) Determination of Nucleotide Sequence of cDNA Encoding the Entire Amino Acid Sequence of Human OBM The nucleotide sequence of the resulting human OBM cDNA obtained in Example 19(4) was determined using the Taq Dye Deoxy Terminator Cycle Sequencing FS kit (Parkin Elmer Co.). Specifically, the nucleotide sequence of the inserted fragment was determined using pUC19hOBM as a template. As primers, primers for the determination of nucleotide sequence of the inserted fragment DNA in pUC19hOBM, M13 Primer M3 and M13 Primer RV (manufactured by Takara Shuzo Co.), and a synthetic primer, human OBM#8, designed based on the nucleotide sequence of the human OBM cDNA fragment (about 690 bp) were used.

The nucleotide sequence of the primers used, M13 Primer M3 and M13 Primer RV, are respectively shown as the Sequence ID No. 4 and No. 5. The amino acid sequence of human OBM deduced from the nucleotide sequence of human OBM cDNA is shown in the Sequence Table as Sequence ID No. 11. The nucleotide sequence of human OBM cDNA is shown as Sequence ID No. 12.

The *Escherichia coli* which was transformed by the pUC19hOBM, which is the plasmid containing the resulting human OBM cDNA, was deposited in National Institute of Bioscience and Human Technology, Agency of Industrial Science and Technology, on Aug. 13, 1997 as deposition No. FERM BP-6058.

Example 20

Radioiodination of OCIF with $^{125}$I and Quantitative Analysis of $^{125}$I-labeled OCIF by ELISA OCIF was labeled with $^{125}$I using the IODO-GEN method. Twenty µl of 2.5 mg/ml IODO-GEN-chloroform solution were transferred to a 1.5 ml Eppendorf tube and the chloroform was evaporated at 40° C., thereby providing a tube coated with IODO-GEN. The tube was washed three times with 400 µl of 0.5 M sodium phosphate buffer solution (Na-Pi, pH 7.0), followed by the addition of 5 µl of 0.5 M Na-Pi (pH 7.0). To this tube was added 1.3 µl (18.5 MBq) of Na—$^{125}$I solution (Amersham Co., NEZ-033H), immediately followed by the addition of 10 µl of 1 mg/ml OCIF solution (monomer type or dimer type). The mixture was mixed in a vortex mixer and allowed to stand at room temperature for 30 seconds. This solution was transferred to a tube to which 80 µl of 0.5 M Na-Pi (pH 7.0) solution containing 10 mg/ml potassium iodine and 5 µl of a phosphate buffered saline solution containing 5% bovine serum albumin (BSA-PBS) were previously added. The solution was mixed, applied to a spin column (1 ml, G-25 Sephadex fine, manufactured by Pharmacia Co.) which was equilibrated with BSA-PBS in advance, and centrifuged for 5 minutes at 2,000 rpm. Four hundred µl of BSA-PBS were added to the fractions eluted from the column. After mixing, 2 µl of the solution were used to measure the radioactivity by a gamma counter. The radiochemical purity of the $^{125}$I-labeled OCIF solution obtained above was measured by counting the radioactivity of fractions precipitated by 10% trichloroacetic acid (TCA).

The biological activity of the $^{125}$I-labeled OCIF was measured according to the method described in WO 96/26217. The concentration of the $^{125}$I-labeled OCIF was measured using the ELISA method as follows. Specifically, 50 mM NaHCO$_3$ (pH 9.6) in which rabbit anti-OCIF polyclonal antibody described in the WO 96/26217 was dissolved to a concentration of 2 µg/ml was added to each well of a 96-well immunoplate (MaxiSorp™, manufactured by Nunc Co.) in the amount of 100 µl per well. After these wells were allowed to stand overnight at 4° C., solution was removed. Then the wells were charged with a mixed aqueous solution of Block Ace™ (Snow Brand Milk Products Co., Ltd.) and a phosphate buffered saline solution (25:75) (B-PBS) in the amount of 200 µl/well. The plate was then allowed to stand for two hours at room temperature. After the solution was removed, the wells were washed three times with a phosphate buffered saline solution containing 0.01% Polysolvate 80 (P-PBS). Next, B-PBS containing $^{125}$I-labeled OCIF sample or the standard OCIF was added in the amount of 100 µl/well. The plate was then allowed to stand for two hours at room temperature. After the solution was removed, each well was washed six times with 200 µl of P-PBS. A solution prepared by diluting peroxidase-labeled rabbit anti-OCIF polyclonal antibody with B-PBS was added in the amount of 100 µl/well. The plate was allowed to stand for two hours at room temperature. After the solution was removed, the wells were washed six times with 200 µl of P-PBS. Then, a TMB solution (TMB Soluble Reagent, High Sensitivity, Scytek Co.) was added in the amount of 100 µl/well. After being allowed to stand at room temperature for 2-3 minutes, 100 µl of a termination solution (Stopping Reagent, Scytek Co.) was added to each well. Absorbance of each well was measured at 450 nm using a microplate reader. The concentration of $^{125}$I-labeled OCIF was determined with a calibration curve prepared using the standard OCIF.

Example 21

Expression of the Protein Encoded by cDNA of the Present Invention (1) Construction of hOBM Expression Vector for Animal Cells pUChOBM was digested with restriction enzyme SalI and a DNA fragment (about 2.2 kb) were purified by electrophoresis on an 1% agarose gel. The ends of the DNA fragments were blunted using a DNA blunting kit (Takara Shuzo Co.) (blunted hOBMcDNA fragment). Expression plasmid pcDL-SR α296 (Molecular and Cellar Biology, Vol. 8, pp 466-472 (1988)) was digested with restriction enzyme EcoRI, blunted with blunting kit and ligated with the blunted hOBM cDNA fragment using DNA ligation kit ver. 2. *Escherichia coli* DHα was transformed with the ligation reaction. A plasmid in the resulting ampicillin resistant transformant was subjected to digestion with restriction enzyme to analyze the DNA restriction map and determine the DNA sequence. As a result, a strain having a plasmid in which hOBM cDNA is inserted in the same direction of transcription as that of SRα promotor was selected. The microorganism strain was named DH5 α/phOBM.

(2) Expression of Human OBM in COS-7 Cells

*Escherichia coli* DH5 α/phOBM was cultured and plasmid phOBM was purified using Qiafilter Plasmid Midi kit (Qiagen Co.) phOBM was transfected using Lipofectamine into COS-7 cells in the wells of a 6-well plate and cultured for two days in DMEM containing 10% fetal bovine serum. The culture medium was replaced with cysteine-methionine-free DMEM (manufactured by Dainippon Seiyaku Co., Ltd.) to which 5% dialysed fetal bovine serum was added (88 µl/well). The cells were incubated for 15 minutes, followed by addition of 14 µl of Express Protein Labeling Mix (NEN Co., 10 mCi/ml). After four hours incubation, 200 µl of DMEM containing 10% fetal bovine serum was added to each well. The cells were cultured for one hour and washed twice with PBS. Then, 0.5 ml of a TSA buffer (10 mM Tris-HCl containing 0.14 M NaCl and 0.025% NaN$_3$, pH 8.0) containing 1% Triton X-100, 1% bovine hemoglobin, 10 µg/ml leupeptin, 0.2 TIU/ml aprotinin, and 1 mM PMSF was added to each well and the mixtures were allowed to stand for one hour on ice. The cells were mixed by pipetting and centrifuged at 3,000×g, for 10 minutes at 4° C., to obtain supernatants. Two hundred µl of a dilution buffer (TSA buffer containing 0.1% Triton X-100, 0.1% bovine hemoglobin, 10 µg/ml leupeptin, 0.2 TIU/ml aprotinin, and 1 mM PMSF) was added to 100 µl of the supernatant from each well. The resulting mixtures were agitated at 4° C. for one hour together with Protein A Sepharose (50 µl) and centrifuged at 1,500×g for one minute at 4° C., to collect supernatants, thereby removing the protein which non-specifically adsorbed Protein A Sepharose. OCIF (1 µg) was added to the supernatants and the mixtures were agitated for one hour at 4° C. to bind human OBM and OCIF. Then, rabbit anti-OCIF polyclonal antibody (50 µg) was added, followed by agitation at 4° C. for one hour. Protein A Sepharose (10 µl) was added to the resulting solution, followed by agitation at 4° C. for an additional hour. The mixtures thus obtained were centrifuged for 1 minute at 1,500×g at 4° C. to collect precipitates. The precipitates were washed twice with a dilution buffer, twice with bovine hemoglobin-free dilution buffer, once with TSA buffer, and once with 50 mM Tris-HCl (pH 6.5). After addition of SDS buffer containing 10% β-mercaptoethanol (0.125 M Tris-HCl, 4% sodium dodecylsulfate, 20% glycerol, 0.002% Bromophenol Blue, pH 6.8), the mixture was heated for 5 minutes at 100° C. and subjected to SDS-PAGE (12.5% polyacrylamide gel, Daiichi Pure Chemical Co.). The gel was fixed and dried according to a conventional method. After isotope signals were enhanced using Amplify™ (Amersham Co.), the dried gel was subjected to autoradiography at −80° C. using Bio Max MR film (Kodak Co.). The results are shown in FIG. 18, which shows that the molecular weight of the protein encoded by the cDNA of the present invention is about 40,000.

Example 22

Binding of the Protein Encoded by cDNA of the Present Invention and OCIF

PhOBM, which was purified in the same manner as in the Example 21(2), was transfected into COS-7 cells in each well of a 24-well plate using Lipofectamine. After cultured for 2 to 3 days, the cells were washed with serum-free DMEM. Two hundred μl of a-culture medium for a binding test medium (serum-free DMEM to which 0.2% bovine serum albumin, 20 mM Hepes buffer solution, 0.1 mg/ml heparin, and 0.2% $NaN_3$ were added) containing 20 ng/ml of $^{125}$I-labeled OCIF was added to the wells. To the other wells, 200 μl of culture medium for the binding test medium containing 8 μg/ml of unlabeled OCIF in addition to 20 ng/ml of $^{125}$I-labeled OCIF, was added. After incubation for one hour at 37° C. in a $CO_2$ incubator (5% $CO_2$), the cells were washed twice with 500 μl of a phosphate buffered saline solution containing 0.1 mg/ml of heparin. Then, 500 μl of 0.1 N NaOH solution was added to each well and the plate was allowed to stand for 10 minutes at room temperature to dissolve the cells. The radioactivity of $^{125}$I in the wells was measured by a gamma counter. As a result, as shown in FIG. 19, it was confirmed that the $^{125}$I-labeled OCIF binds only to the cells transfected with phOBM. Moreover, the binding was significantly inhibited by adding 400-fold excess unlabelled OCIF (8 μg/ml). Based on the results described above, the protein, human OBM encoded by the cDNA in the phOBM was confirmed to specifically bind to OCIF on the surface of COS-7 cells.

Example 23

Crosslinking of $^{125}$I-labeled OCIF and the Protein Encoded by the cDNA of the Present Invention Crosslinking of $^{125}$I-labeled monomer type OCIF and the protein encoded by the cDNA of the present invention was carried out to further investigate the characteristics of the protein encoded by the cDNA of the present invention. After constructing expression vector phOBM and transfecting into COS-7 cells according to the method used in the Examples 21 (1) and 21 (2), 200 μl of binding test medium containing $^{125}$I-labeled OCIF (25 ng/ml) described above was added. The binding test medium to which unlabeled OCIF was added at a 400-fold concentration in addition to $^{125}$I-labeled OCIF was used for the other wells. After cultured for one hour at 37° C. in a $CO_2$ incubator(5% $CO_2$), the cells were washed twice with 500 μl of phosphate buffered saline containing 0.1 mg/ml heparin. Five hundred μl of phosphate buffered saline in which 100 μg/ml of a crosslinking agent (DSS: disuccinimidyl suberate, manufactured by Pierce Co.) was dissolved was added to the cells, followed by incubation for 10 minutes at 0° C. The cells in these wells were washed twice with 1 ml of ice-cold phosphate buffered saline. After an addition of 100 μl of 20 mM Hepes buffer solution containing 1% Triton X-100 (Wako Pure Chemicals Co., Ltd.), 2 mM PMSF (Phenylmethylsulfonyl fluoride, Sigma Co.), 10 μM Pepstatin (Wako Pure Chemicals Co., Ltd.), 10 μM leupeptin (Wako-Pure Chemicals Co., Ltd.), 10 μM antipain (Wako Pure Chemicals Co., Ltd.) and 2 mM EDTA (Wako Pure Chemicals Co., Ltd.), the wells were allowed to stand for 30 minutes at room temperature to dissolve the cells. These samples (15 μl aliquots) were treated with SDS under reducing conditions according to a conventional method and subjected to SDS-electrophoresis using 4-20% polyacrylamide gradient gel (Daiichi Pure Chemical Co., Ltd.). After electrophoresis, the gel was dried and subjected to autoradiography for 24 hours at –80° C. using BioMax MS film (Kodak Co.) and BioMax MS sensitization screen (Kodak Co.). The film subjected to autoradiography was developed according to a conventional method. As a result, a band of a molecular weight in the range of 90,000-110,000, shown in FIG. 20, was detected by crosslinking of $^{125}$I-labeled monomer type OCIF and the protein encoded by the cDNA of the present invention.

Example 24

Expression of Secreted-form Human OBM (1) Construction of Secreted-form Human OBM Expression Plasmid A PCR was carried out using human OBM SF (SEQ ID NO:13) and mouse OBM #8 (SEQ ID NO:6) as primers and pUC 19hOBM as a template. After purification by electrophoresis on an agarose gel, the product was digested with restriction enzymes SpII and HindIII, and further purified by electrophoresis on an agarose gel to obtain a purified fragment (0.27 kb). Human OBM cDNA was partially digested with restriction enzyme DraI and DNA fragments digested with DraI at one site were purified by electrophoresis on an agarose gel. The purified fragment was further digested with restriction enzyme HindIII. The 0.53 kb DraI/HindIII fragment was purified by electrophoresis on an agarose gel. The purified fragment was ligated with the 0.27 kb SpII/HindIII fragment derived from the PCR described above using ligation kit ver. 2 (Takara Shuzo Co.) together with HindIII/EcoRI fragment (5.2 kb) of pSec TagA (Invirogen Co.). *Escherichia coli* DH5 α was transformed using the reaction product. Plasmids were purified by alkali SDS method from the resulting ampicillin resistant transformants and digested with restriction enzymes to select a plasmid containing 0.27 kb and 0.53 kb-fragments as inserts in pSec TagA. This plasmid was confirmed to have a sequence encoding the secreted human OBM by sequencing using a Taq dyedeoxyterminator cycle sequencing FS kit (Perkin Elmer Co.). The plasmid was digested with restriction enzymes NheI and XhoI to prepare a fragment (0.8 kb) corresponding to the secreted human OBM cDNA by electrophoresis on an agarose gel. This fragment was inserted into the NheI and XhoI fragment (10.4 kb) of an expression vector pCEP4 (Invirogen Co.) using a ligation kit and *Escherichia coli* DH5 α was transformed using the reaction product. Plasmids were purified by alkali-SDS method from the resulting ampicillin resistant transformants and digested with restriction enzymes to select an *Escherichia coli* having the expression plasmid for secreted-form human OBM (pCEPshOBM). The *Escherichia coli* containing the pCEPshOBM was cultured and pCEPshOBM was purified using a Qiafilter™ plasmid midi kit (Qiagen Co.).

(2) Expression of Secreted-form OBM

293-EBNA cells were suspended in IMDM containing 10% FCS (IMDM-10% FCS), added into a 24-well plate coated with collagen (manufactured by Sumitomo Bakelite Co., Ltd.) in a cell density of $2 \times 10^5/2$ ml/well and cultured overnight. The cells were transfected with 1 μg of pCEPshOBM or pCEP4 using 4 μl of Lipofectamine (Gibco Co.). After cultured for two days in 0.5 ml of a serum-free IMDM or IMDM-10% FCS, the culture supernatants were collected. Expression of the secreted human OBM in the culture supernatant was detected as follows. Sodium bicarbonate was added to the culture supernatants to a final concentration of 0.1 M and the mixtures were added to a 96-well plate. The plate was allowed to stand overnight at 4° C., thereby immobilizing human OBM in the culture supernatants on the 96-well plate. The plate was blocked using Block Ace™ (Snow Brand Milk Products Co., Ltd.) solution four-fold diluted with PBS (B-PBS) and allowed to stand for two hours at room temperature. After adding 3-100 ng/ml of OCIF which was diluted with B-PBS to each well, the plate was allowed to stand for two hours at 37° C., followed by wash with PBS containing 0.05% Polysolvate 20(P-PBS). Then, 100 µl of a peroxidase-labeled rabbit anti-OCIF polyclonal antibody described in WO 96/26217 which was diluted with B-PBS was-added to each well. After allowing to stand for two hours at 37° C., the wells were washed six times with P-PBS. Then, TMB solution (TMB Soluble Reagent, High Sensitivity, Scytek Co.) was added in the amount of 100 µl per well and the mixture was allowed to stand at room temperature for about 10 minutes. The reaction was terminated by the addition of 100 µl of termination solution (Stopping Reagent, Scytek Co.) to each well. Absorbance at 450 nm for each well was measured by a microplate reader. The results are shown in FIG. 21, which indicates that the absorbance at 450 nm increased according to the concentration of the added OCIF in the plate in which the conditioned medium of the cells transfected with pCEPshOBM was immobilized. On the other hand, no increase in absorbance was seen in the wells in which the conditioned medium of the cells transfected with vector pCEP4 was immobilized. FIG. 22 shows the results of an experiment wherein the proportion of the conditioned medium used for immobilization was changed within a range of 5-90% in the presence of a constant concentration of OCIF (50 ng/ml). The absorbance at 450 nm increased according to the increase in the proportion of the conditioned medium in the plate wherein the conditioned medium of the cells transfected with pCEPshOBM was immobilized, whereas no such increase in absorbance was seen in the plate wherein the conditioned medium of the cells transfected with vector pCEP4 was immobilized. From these results, it was confirmed that secreted-form human OBM is produced in the conditioned medium of the cells transfected with pCBPshOBM.

Example 25

Expression of Thioredoxin-human OBM Fusion Protein (Trx-hOBM)

(1) Construction of a Thioredoxin-human OBM Fusion Protein (Trx-hOBM) Expression Vector Ten µl of 10× ExTaq buffer (Takara Shuzo Co.), 8 µl of 10 mM dNTP (Takara Shuzo Co.), 77.5 µl of sterilized distilled water, 2 µl of an aqueous solution of pUC19hOBM(10 ng/µl), 1 µl of primer, mouse OBM#3 (100 pmol/µl, Sequence Table, Sequence ID No. 9), 1 µl of primer, hOBM SalR2 (100 pmol/µl, Sequence Table, Sequence ID No. 14), and 0.5 µl of ExTaq (5 u/µl) (Takara Shuzo Co.) were mixed and reacted (PCR) in a micro centrifugel tube. After the reaction at 95° C. for 5 minutes, at 50° C. for one second, at 55° C. for one minute, at 74° C. for one second, and at 72° C. for 5 minutes, a cycle reaction consisting of a reaction at 96° C. for one minute, at 50° C. for one second, at 55° C. for one minute, at 74° C. for one second, and at 72° C. for 3 minutes, was repeated 25 times. From the total reaction mixture DNA fragment (750 bp) was purified. The whole amount of purified DNA fragment was digested with restriction enzymes SalI (Takara Shuzo Co.) and BspHI (New England Bilabs Co.), and subjected to electrophoresis on a 1% agarose gel to obtain purified DNA fragment (Fragment 1, about 320 bp). The fragment was dissolved in 20 µl of sterilized distilled water. In the same manner, DNA fragment (Fragment 2, about 450 bp) obtained by digesting 4 µg of pUC19hOBM with restriction enzymes BamHI, and BspHI (Takara Shuzo Co.) and DNA fragment (Fragment 3, about 3.6 kb), obtained by digesting 2 µg of pTrXFus (InVitrogen Co.) with restriction enzymes BamHI, and SalI (Takara Shuzo Co.) were respectively purified and dissolved in 20 µl of sterilized distilled water. The QIAEXII gel extraction kit was used for purification of the DNA fragments. Fragments 1-3 were ligated by incubating at 16° C. for 2.5 hours using DNA ligation kit ver. 2 (Takara Shuzo Co.). Using the ligation reaction, *Escherichia coli* GI724 (Invirogen Co.) was transformed according to the method described in the Instruction Manual of ThioFusion Expression System (Invirogen Co.). A microorganism strain with plasmid in which the hOBM cDNA fragment is fused in frame to thioredoxin gene was selected from the resulting ampicillin resistant transformants by analysis of DNA restriction map obtained by digestion with restriction enzyme and by determination of DNA sequence. The microorganism strain thus obtained was named GI724/pTrxhOBM.

(2) Expression of Trx-hOBM in *Escherichia coli*

GI724/pTrxhOBM and GI724 containing pTrxFus (GI724/pTrxFus) were respectively cultured six hours with shaking at 30° C. in 2 ml of RMG-Amp medium (0.6% $Na_2HPO_4$, 0.3% $KH_2PO_4$, 0.05% NaCl, 0.1% $NH_4Cl$, 2% casamino acid, 1% glycerol, 1 mM $MgCl_2$, 100 µg/ml ampicillin, pH 7.4). The broth (0.5 ml) was added to 50 ml of Induction medium (0.6% $Na_2HPO_4$, 0.3% $KH_2PO_4$, 0.05% NaCl, 0.1% $NH_4Cl$, 0.2% casamino acid, 0.5% glucose, 1 mM $MgCl_2$, 100 µg/ml ampicillin, pH 7.4) and cultured with shaking at 30° C. When $OD_{600nm}$ reached about 0.5, L-tryptophan was added to a final concentration of 0.1 mg/ml, followed by culturing with shaking at 30° C. for an additional 6 hours. The culture broth was centrifuged at 3000×g to collect the cells, which were then suspended in 12.5 ml of PBS. The suspension was subjected to an ultrasonic generator (Ultrasonics Co.) to disrupt the cells. The disrupt cells were centrifuged at 7000×g for 30 minutes to obtain a supernatant liquid as a soluble protein fraction. Ten µl of this soluble protein fraction was subjected to SDS polyacrylamide (10%) electrophoresis under reducing conditions. As a result, as shown in FIG. 23, a band with a molecular weight of 40,000 which was not detected in the soluble protein fraction of GI724/pTrxFus was found in the soluble protein fraction of GI724/pTrxhOBM. Accordingly, it was confirmed that a fusion protein (Trx-hOBM) of thioredoxin and human OBM was expressed in *Escherichia coli*.

(3) Binding Capability of Trx-hOBM to OCIF

Binding of the expressed Trx-hOBM to OCIF was confirmed according to the following experiment. Anti-thioredoxin antibody (Invirogen Co.) which was diluted 5000-fold with 10 mM sodium hydrogen carbonate solution was added to a 96-well immunoplate (Nunc Co.) in the amount of 100 µl per well. After being allowed to stand overnight at 4° C., the liquid in the wells was discarded. Two hundred µl of a solution prepared by diluting Block Ace™ (Snow Brand Milk Products Co., Ltd.) two-fold with PBS (BA-PBS) was added to each well. After being allowed to stand for one hour at room temperature, the wells were washed three times with P-PBS. The soluble protein fractions originating from the above-described GI724/pTrxhOBM or GI724/pTrxFus, each diluted with BA-PBS in various concentrations were added to each well in the amount of 100 µl. After being allowed to stand for two hours at room temperature, each well was washed three times with P-PBS and charged with 100 µl of OCIF (100 ng/ml) which was diluted with BA-PBS. After being allowed to stand for two hours at room temperature, each well was washed three times with P-PBS and charged with 100 μl of peroxidase-labeled anti-OCIF antibody (described in WO 96/26217) which was diluted 2,000-fold with BA-PBS. After being allowed to stand for two hours at room temperature, each well was washed six times with P-PBS and charged with 100 μl of TMB solution. After being allowed to stand for about 10 minutes at room temperature, each well was charged with 100 μl of termination solution (Stopping Reagent). Absorbance of each well at 450 nm was measured by a microplate reader. The results are shown in FIG. 24. There was no difference in the absrobance between the sample with the soluble protein fraction originating from GI724/pTrxFus added thereto and the sample without the addition of this soluble protein fraction. On the other hand, the absorbance increased in the samples to which the soluble protein fraction originating from GI72/pTrxhOBM was added in proportion to the concentration of the soluble protein fraction. The results of the other experiment wherein the dilution rate of the soluble protein fraction was maintained constant (1%) while adding OCIF diluted with BA-PBS in different concentrations (0-100 ng/ml) are shown in FIG. 25. It can be seen that the absorbance remained low at any concentrations of OCIF in samples using a soluble protein fraction originating from GI724/pTrxFus, whereas the absorbance increased in proportion to the OCIF concentration in the samples to which the soluble protein fraction originating from GI724/pTrxhOBM was added. Based on these results, it was confirmed that Trx-hOBM which is produced from GI724/pTrxhOBM has a capability of binding to OCIF.

(4) Large-scale Cultivation of *Escherichia coli* Which Produces Trx-hOBM

GI724/pTrxhOBM cells were spread on RMG-Amp agar (0.6% $Na_2HPO_4$, 0.3% $KH_2PO_4$, 0.05% NaCl, 0.1% $NH_4Cl$, 2% casamino acid, 1.5% agar, pH 7.4) using a platinum transfer 100 p. The cells were cultured overnight at 30° C. The cultured cells were suspended in 10 ml of Induction medium. The suspension was added (5 ml for each) to two 2 l Erlenmeyer flasks containing 500 ml of Induction medium and cultured at 30° C. with shaking. When the $OD_{600nm}$ reached about 0.5, L-tryptophan was added to a final concentration of 0.1 mg/ml. Culturing with shaking was continued for six hours at 30° C. The culture broth was centrifuged for 20 minutes at 3000×g to collect the cells, which were suspended in 160 ml of PBS. The suspension was subjected to an ultrasonic generator (Ultrasonics Co.) to disrupt the cells. The supernatant liquid was centrifuged for 30 minutes at 7000×g to obtain a soluble protein fraction.

(5) Preparation of OCIF-immobilized Affinity Column

Two g of TSKgel AF-Tolesyl Toyopal 650 (Tosoh Corp.) and 40 ml of 1.0 M potassium phosphate buffer (pH 7.5) containing 35.0 mg of recombinant OCIF, which was prepared according to the method described in WO 96/26217, were mixed. The mixture was gently shaken overnight at 4° C. to effect a coupling reaction. The reaction mixture was centrifuged to remove the supernatant. To inactivate excess active residues, 40 ml of 0.1 M Tris-HCl buffer (pH 7.5) was added to the precipitated carrier and the mixture was gently shaken at room temperature for one hour. The carrier in a column was washed with 0.1 M glycine-HCl buffer (pH 3.3) containing 0.01% Polysorbate 80 and 0.2 M NaCl and 0.1 M sodium citrate buffer (pH 2.0) containing 0.01% Polysorbate 80 and 0.2 M NaCl. The carrier in the column was equilibrated by charging twice with 10 mM sodium phosphate buffer (pH 7.4) containing 0.01% Polysorbate 80.

(6) Purification of Trx-hOBM Using OCIF-immobilized Affinity Column

Unless otherwise indicated, purification of Trx-hOBM was carried out at 4° C. The above-mentioned OCIF-immobilized affinity carrier (10 ml) and the soluble protein fraction (120 ml) prepared in Example 25(4) were mixed. The mixture was gently shaken overnight at 4° C. in four 50 ml centrifugel tubes using a rotor. An Econo-column™ (internal diameter: 1.5 cm, length: 15 cm, manufactured by BioRad Co.) was filled with the carrier in the mixture. The column was charged with 300 ml of PBS containing 0.01% Polysorbate 80, 100 ml of 10 mM sodium phosphate buffer (pH 7.0) containing 0.01% Polysorbate 80 and 2.0 M NaCl, and 100 ml of 0.1 M glycine-HCl buffer (pH 3.3) containing 0.01% Polysorbate 80 and 0.2 M NaCl, in that order. Next, proteins adsorbed in the column were eluted with 0.1 M sodium citrate buffer (pH 2.0) containing 0.01% Polysorbate 80 and 0.2 M NaCl. The eluate was collected in 5 ml portions. Each fraction thus collected was immediately neutralized with addition of 10% volume of 2 M Tris buffer solution (pH 8.0). Presence or absence of Trx-hOBM in the eluted fractions was determined according to the method previously described in Example 25(3) (the binding capability to OCIF). The fractions containing Trx-hOBM were collected and purified further.

(7) Purification of Trx-hOBM by Gel Filtration

About 25 ml of Trx-hOBM fractions obtained in Example 25(6) was concentrated to about 0.5 ml by centrifuging using Centriplus 10 and Centricon 10 (Amicon Co.). This sample was applied to a Superose 12 HR 10/30 column (1.0×30 cm, Pharmacia Co.) previously equilibrated with PBS containing 0.01% Polysorbate 80. For the separation, PBS containing 0.01% Polysorbate 80 was used as a mobile phase at a flow rate of 0.25 ml/min. The eluate from the column was collected in 0.25 ml portions. The Trx-hOBM in the thus-collected fractions was detected by the same method as previously described in the Example 25(3) and SDS-PAGE. Fractions containing purified Trx-hOBM were collected and the protein concentration of Trx-hOBM was determined. The measurement of the protein concentration was carried out using bovine serum albumin as a standard substance using DC-Protein assay kit (BioRad Co.).

Example 26

Osteoclast Formation-inducing Activity of hOBM phOBM and pcDL-SRα296 were respectively transfected into COS-7 cells using Lipofectamine (Gibco Co.). The cells were cultured for one day in DMEM containing 10% FCS, trypsinized, plated on cover slips (15 mm round shape, manufactured by Matsunami Co.) in 24-well plates at $5×10^4$ cells per well, and cultured for 2 days. The culture plate was washed once with PBS. The cells were fixed with PBS containing 1% paraformaldehyde at room temperature for 8 minutes. The plate on which the fixed cells were attached was washed 6 times with PBS, then 700 μl of mouse spleen cells suspended at $1×10^6$/ml in α-MEM containing $10^{-8}$ M active-form vitamin $D_3$, $10^{-7}$ M dexamethasone, and 10% fetal bovine serum were added to each well. Millicell PCF (Millipore Co.) was set in each well and a suspension of ST2 cells in the above-mentioned culture medium ($4×10^4$/ml) were added, 700 μl per well, into the Millicell PCF followed by incubation at 37° C. for 6 days. After the culture, the Millicell PCF was removed, the plate was washed once with PBS, and the cells were fixed with acetone-ethanol solution (50:50) for one minute. Then, the cells exhibiting tartaric acid-resistant acid phophatase activity (TRAP), which is a specific marker for osteoclast, were selectively stained using LEUKOCYTE ACID PHOSPHATASE kit (Sigma Co.). As a result of microscopic observation, TRAP-positive cells were not detected in the wells in which COS-7 cells transfected with pcDL-SR α296 were fixed. In contrast, 65±18 (average±standard deviation, n=3) TRAP positive cells were observed in the wells in which COS-7 cells transfected with phOBM were fixed. Moreover, expression of calcitonin receptor was confirmed by the fact that $^{125}$I-labeled salmon calcitonin (Amersham Co.) specifically bound to these TRAP positive cells. Based on these findings, it has been proven that human OBM, which is the protein encoded by cDNA of the present invention, has osteoclast formation-inducing activity.

Example 27

Osteoclast Formation-inducing Activity of Trx-hOBM and Secreted-form Human OBM

Mouse spleen cells were suspended in α-MEM containing $10^{-8}$ M active-form vitamin $D_3$, $10^{-7}$ M dexamethasone, and 10% fetal bovine serum at a concentration of $2\times10^6$/ml. The suspension was added to a 24 well plate in the amount of 350 µl per well. Each well was then charged with 350 µl of a solution prepared by diluting purified Trx-hOBM with the above-mentioned culture medium (40 ng/ml), 350 µl of solution prepared by 10-fold diluting a conditioned medium which was produced by culturing 293-EBNA cells, onto which pCEPshOBM or pCEP4 were transfected, in a culture medium IMDM-10% FCS, with above-mentioned culture medium, or 350 µl only of the above-mentioned culture medium. The Millicell PCF (Mollipore Co.) was placed on each well, to which 600 µl of ST2 cells which were suspended in the above-mentioned culture medium ($4\times10^4$/ml) were added. After cultured for six days, the Millicell PCF was removed. The plate was washed once with PBS and the cells were fixed by acetone-ethanol solution (50:50) for one minute. Then, the cells exhibiting the activity of tartaric acid resistant acidic phophatase (TRAP activity) were selectively stained using LEUKOCYTE ACID PHOSPHATASE kit (Sigma Co.). The results of microscopic observation revealed that no cells exhibiting the TRAP activity were detected in the wells to which no Trx-hOBM was added, whereas 115±19 (average±standard deviation, n=3) TRAP-positive cells were observed in the wells to which Trx-hOBM was added. Similarly, while no cells exhibiting TRAP activity were detected in the wells to which conditioned medium of 293-EBNA cells transfected with pCEP4 had been added, 125±23 (average±standard deviation, n=3) TRAP positive cells were observed in the wells to which conditioned medium of 293-EBNA cells transfected with pCEPshOBM had been added. Moreover, expression of calcitonin receptor was confirmed by the fact that $^{125}$I-labeled salmon calcitonin (Amersham Co.) specifically binds to these TRAP positive cells. These results have proven that Trx-hOBM and secreted-form hOBM exhibit osteoclast formation-inducing activity.

Example 28

Preparation of Polyclonal Antibody

Mouse SOBM or human sOBM used as an immunogen was prepared according to the method described above. Especially, mouse SOBM cDNA (cDNA (Sequence ID No. 18) encoding mouse sOBM (Sequence ID No. 16) which does not have the membrane binding region of the mouse OBM due to absence of the amino acids from the N-terminal down to the 72nd amino acid) or human sOBM cDNA (cDNA (Sequence ID No. 19) encoding human sOBM (Sequence ID No. 17) which does not have the membrane binding region of human OBM due to absence of the amino acids from the N-terminal down to the 71st amino acid) was ligated with a Hind III/EcoRV fragment (5.2 kb) of the expression vector pSec TagA (InVitrogen Co.) including the nucleotide sequence encoding a signal peptide of κ-chain of immunoglobulin, together with an EcoRI/PmaCl fragment (0.32 kb) of OBM cDNA, using a ligation kit ver. 2 (Takara Shuzo Co.). *Escherichia coli* DH5α was transformed with the reaction product. The plasmids obtained from the resulting ampicillin resistant strains were purified by the alkali SDS and digested with an restriction enzyme to select a plasmid with 0.6 Kb and 0.32 kb fragments inserted into pSec TagA. The sequence of this plasmid was identified using the Dyedeoxyterminator Cycle Sequencing FS kit (product of Perkin Elmer Co.). As a result, it was confirmed that this plasmid has a sequence encoding mouse or human sOBM. After plasmid was digested with restriction enzymes NheI/XhoI, a fragment (1.0 kb) corresponding to secretion form OBM cDNA was recovered by agarose gel electrophoresis. This fragment was inserted into an NheI/XhoI fragment (10.4 kb) of the expression vector pCEP4 (InVitrogen Co.) using a ligation kit. *Escherichia coli* DH5 α was transformed using the reaction product. Plasmids were purified by the alkali SDS from the resulting ampicillin resistant strains. Analyzing these plasmids by digesting with a restriction enzyme, *Escherichia coli* possessing a secretion type OBM expression plasmid (pCEP sOBM) having the objective structure was selected. The *Escherichia coli* strain having the pCEP sOBM was cultured and pCEP sOBM was purified using a Qiafilter plasmid midy kit (Qiagen Co.). Next, 293-EBNA cells were suspended in IMDM (IMDM-10% FCS) containing 10% FCS and plated onto a 24-well plate coated with collagen (product of Sumitomo Bakelite Co., Ltd.) at a cell density of $2\times10^5$cells/2 ml/well. After culturing overnight, the cells were tranformed with 1 µg of pCEP sOBM or pCEP4 using 4 µl of Lipofectamine (Gibco Co.) and further cultured for two days in 0.5 ml of serum-free IMDM or IMDM-10% FCS. The culture supernatant was recovered. A cell line with high productivity of recombinant mouse soluble OBM (msOBM) or human soluble OBM (hsOBM) was screened as follows. Sodium bicarbonate was added to the culture supernatant which is assumed to contain msOBM or hsOBM to a final concentration of 0.1 M. One hundred µl of the culture supernatant was added to each well in 96-well immunoplates (Nunc Co.) and allowed to stand overnight at 4° C., thereby msOBM or hsOBM in the culture supernatant was immobilized on each well. To each well, 200 µl of Block Ace™ (Snow Brand Milk Products Co., Ltd.) solution diluted four-fold with PBS (B-PBS) was added and the plates were allowed to stand for two hours at room temperature. After washing each well in the plates three times with PBS (P-PBS) containing 0.1% Polysorbate 20, 100 µl of each recombinant OCIF (rOCIF) solution (3-100 ng/ml) diluted serially with P-PBS was added to each well in the plates. The plates were allowed to stand for two hours at 37° C. After washing the plates three times with PBS, 100 µl of a peroxidase-labeled anti-OCIF polyclonal antibody (WO 96/26217) diluted with B-PBS was added to each well. After allowing to stand for two hours at 37° C., the wells were washed six times with P-PBS. Then, 100 µl of TMB solution (TMB Soluble Reagent, High Sensitivity, ScyTek Co.) was added to each well in the plates and the plates were allowed to stand at room temperature for about 10 minutes, subsequently the reaction was terminated by adding 100 µl of a stopping solution (Stopping Reagent, ScyTek Co.) to each well. Absorbance at 450 nm of each well was measured using a microplate reader. It was confirmed that the absorbance increased remarkably in proportion to concentration of the added OCIF in the plates in which msOBM or hsOBM in the culture supernatant of the cell line producing msOBM or hsOBM was immobilized therein.

The cell line that exhibited a high rate of increase in absorbance was selected as a a strain with high productivity. Thus-related 293-EBNA cells with high productivity of msOBM or hsOBM were cultured on a large scale in an IMDM medium containing 5% FCS, using 25 T-flasks (T-225). After the cell reached to confluent, a fresh culture medium was added to each T-225 flask in the amount of 100 ml per flask and cells were cultured for 3-4 days, to collect the culture supernatant. These procedures were repeated four times to obtain 10 L of the culture supernatant containing msOBM or hsOBM. Purified msOBM (10 mg) or hsOBM (12 mg), which shows homogeneous band (molecular weight: 32 kDa) on SDS-polyacrylamide gel electrophoresis, were obtained from the culture supernatant by means of affinity chromatography on an OCIF-immobilized column and gel filtration chromatography according to the method described in examples 25 (6) and 25 (7). Each thus-obtained purified preparation was used as an antigen for immunization. Each protein antigen obtained was dissolved in phosphate buffered saline (PBS) to a concentration of 200 µg/ml and emulsified with an equivalent volume of Freund's complete adjuvant. One ml of the emulsion was subcutaneously immunized to each of three Japanese white rabbits about once every week. A booster injection was given when the antibody titer reached a peak. Whole blood was collected 10 days thereafter. The serum was diluted two-fold with a binding buffer for protein A sepharose chromatography (BioRad Co.) and applied to a protein A column equilibrated with the same buffer. After washing the column extensively with the same buffer, the anti-sOBM antibody adsorbed to the column was eluted with an elution buffer (BioRad Co.) or 0.1 M glycine-HCl buffer, pH 3.0. To neutralize the eluate immediately, the eluate was fractionated using test tubes containing a small amount of 1.0 M Tris-HCl (pH 8.0). The eluate was dialyzed against PBS overnight at 4° C. The antibody content in the antibody solution was measured by the Lowry method using bovine IgG as a standard protein. Thus, about 10 mg of purified immunoglobulin (IgG) containing the polyclonal antibody of the present invention per 1 ml of rabbit antiserum was obtained.

Example 29

Measurement of OBM and sOBM by ELISA Using Polyclonal Antibody

A sandwich ELISA was constructed using the rabbit anti-human sOBM polyclonal antibody obtained in Example 28 as the solid phase antibody and enzyme-labeled antibody. Peroxidase (POD)-labeled antibody was prepared according to the method of Ishikawa (Ishikawa et al., J. Imunoassay, Vol. 4, 209-327, 1983).

The anti-human sOBM polyclonal antibody obtained in the Example 28 was dissolved in a 0.1 M NaHCO$_3$ to a concentration of 2 µg/ml. One hundred µl of the resulting solution was added to each well in 96-well immunoplates (Nunc Co.), which was then allowed to stand at room temperature overnight. Next, 200 µl of 50% Block Acem™ (Snow Brand Milk Co., Ltd.) was added to each well and the plates were allowed to stand for one hour at room temperature. The wells were washed three times with PBS containing 0.1% Polysorbate 20 (washing buffer).

Human OBM was expressed according to the method of Example 26 and purified according to the method of Example 2. The purified human OBM and the purified human sOBM prepared in example 28 were serially diluted with the first reaction buffer (0.2 M Tris-HCl buffer, pH 7.2, containing 40% Block Ace and 0.1% Polysorbate 20), respectively, and 100 µl of the diluted solution was added to each well in the plates. The plates were allowed to stand at room temperature for two hours, and washed three times with the above-mentioned washing buffer. Subsequently, 100 µl of POD-labeled anti-human sOBM polyclonal antibody diluted 1000-fold with the second reaction buffer (0.1 M Tris-HCl buffer, pH 7.2, containing 25% Block Ace and 0.1% Polysorbate 20) was added to each well in the plates. After the plates were allowed to stand at room temperature for two hours, each well was washed three times with the washing buffer. Next, 100 µl of enzyme substrate solution (TMB, ScyTek Co.) was added to each well in the plates, and the plates were allowed to stand for 10 minutes, followed by the addition of 100 µl of a reaction termination solution (Stopping reagent, ScyTek Co.) to stop the enzyme reaction. The absorbance at 450 m of each well was measured using a microplate reader. The results are shown in FIG. 26. The sandwich ELISA using a rabbit anti-human sOBM polyclonal antibody recognized almost equally human sOBM (molecular weight, about 32 kDa) and human OBM (molecular weight, about 40 kDa), with a measurement sensitivity of about $12.5 \times 10^{-3}$ pmol/ml (human OBM: about 500 pg/ml, human sOBM: about 400 pg/ml). The measurement of mouse sOBM and mouse OBM by ELISA using the rabbit anti-mouse sOBM polyclonal antibody obtained in the Example 28 was able to be carried out in the same manner. It was confirmed that an extremely small amount of mouse sOBM or mouse OBM can be measured with almost the same sensitivity as described above.

As mentioned above, the anti-human sOBM polyclonal antibody of the present invention prepared in the Example 28 can equally recognize both the human sOBM and human OBM antigens. Therefore, the antibody was named anti-human OBM/sOBM polyclonal antibody. Similarly, the anti-mouse sOBM polyclonal antibody prepared in the Example 28 can equally recognize both the mouse sOBM and mouse OBM antigens. This antibody was therefore named anti-mouse OBM/sOBM polyclonal antibody.

Example 30

Preparation of Monoclonal Antibody

The purified human sOBM prepared in the Example 28 was used as the antigen for immunization. The purified human sOBM was dissolved in physiological saline solution to a concentration of 10 µg/ml and emulsified by mixing with an equivalent volume of Freund's complete adjuvant. The emulsion was intraperitoneally administered to BALB/c mice at a dose of 200 µl three times, once a week, to immunize mice. Next, the equivalent volume of the Freund's complete adjuvant was added to a physiological saline solution containing 5 µg/ml of human sOBM and the mixture was sufficiently emulsified. This emulsion was injected intraperitoneally to BALB/c mice at a dose of 200 µl, once a week for four weeks for immunization. One week after the fourth immunization, 100 µl of a physiological saline solution containing 10 µg/ml of human sOBM was intravenously administered to the BALB/c mice as a booster. After three days, the spleen was extracted and spleen cells were separated. The spleen cells were fused with mouse myeloma cells, P3x63-Ag8.653 according to a conventional method (Koehler, G. and Milstein, C., Nature, 256, 495 (1975)). The suspended fused cells were cultured for 10 days in an HAT medium containing hypoxanthine, aminopterin, and thymidine. After the myeloma cells were dead and hybridomas appeared, the HAT medium was replaced with an aminopterin-free HAT medium, and the cell culture was continued.

Example 31

Selection of Hybridoma and Cloning

Appearance of hybridomas was recognized 10 days after cell fusion in Example 30. Monoclonal antibodies recognizing the human sOBM with high affinity and hybridomas producing these antibodies were selected according to the following procedure using the improved solid phase ELISA which is described below. In addition, to select the anti-OBM monoclonal antibody which recognizes both human sOBM and mouse sOBM, mouse sOBM prepared in the Example 27 was used in addition to human sOBM as the antigen for the solid phase ELISA. The human sOBM and mouse sOBM were respectively dissolved in a 0.1 M sodium bicarbonate solution at a concentration of 5 μg/ml. Fifty ml of each antigen solution was added to each well in 96-well immunoplates (Nunc Co.). The plates were allowed to stand at 4° C. overnight to immobilize the antigens. The antigen solution in each well was discarded. Each well was then filled with 200 μl of 50% Block Ace™ (Snow Brand Milk Products Co., Ltd.) and allowed to stand at room temperature for one hour. After each well was washed with phosphate buffered saline solution (PBS-P) containing 0.1% Polysorbate 20 , 40 μl of calf serum (Hiclone Inc.) was added to each well. Subsequently, 10 μl of each hybridoma culture supernatant was added to each well and each well was incubated at room temperature for two hours in the presence of 80% calf serum. The object of the solid phase ELISA in the presence of 80% calf serum is to select a hybridoma which produce an antibody which can detect a very small amount of human sOBM or mouse sOBM even in a solution containing high concentration of protein and in the presence of an immunoreaction interfering substance derived from serum, i.e. a hybridoma which can produce an antibody with a high affinity for human sOBM or mouse sOBM. After the reaction at room temperature for two hours, the plates were washed with PBS-P and subsequently, 50 μl of peroxidase-labeled anti-mouse IgG (KPL Co.) diluted 5000-fold with physiological saline solution containing 25% Block Ace was added to each well. After the reaction at room temperature for two hours, the plate was washed three times with PBS-P. After the addition of 50 μl of an enzyme substrate solution (TMB, ScyTek Co.) to each well, the reaction was continued at room temperature for five minutes. The enzymatic reaction was stopped by the addition of 50 μl of a termination solution (stopping reagent, ScyTek Co.). Hybridomas which produce antibodies recognizing human sOBM or mouse sOBM were selected by measuring absorbance at 450 nm of each well using a microplate reader (Immune Reader NJ2000™, Nippon InterMed Co.). Hybridomas producing antibodies exhibiting particularly high absorbance ($OD_{450\,nm}$) were selected. Cloning of these hybridomas by a limiting dilution method was repeated 3 to 5 times to establish stable hybridomas. Hybridomas exhibiting particularly high antibody productivity were selected among the established antibody-producing hybridoma clones.

Example 32

Production and Purification of Monoclonal Antibody

The antibody-producing hybridomas obtained in the Example 31, i.e. high affinity antibody-producing hybridoma which recognizes human sOBM and hybridoma which produces an antibody showing cross-reactivity to the mouse sOBM were cultured, respectively. Each hybridoma was implanted intraperitoneally to BALB/c mice ($1\times10^6$ cells per mouse) to which pristan (Aldorich Co.) was administered one week previously. After about 2-3 weeks, accumulated ascites were collected. The monoclonal antibody, which recognizes human sOBM of the present invention or both the human sOBM and mouse sOBM in the ascites, was purified according to the purification method of anti-OBM/sOBM polyclonal antibodies using a Protein A column described in the Example 28. The purified monoclonal antibody was thus obtained from the ascites by Protein A column chromatography (Pharmacia Co.).

Example 33

Antigen Specificity of Monoclonal Antibody

The antigen specificity of a monoclonal antibody which specifically recognizes human sOBM and the monoclonal antibody exhibiting cross-reactivity to both the human sOBM and mouse sOBM was investigated using human sOBM, human intact OBM having a membrane binding region, mouse sOBM, and mouse intact OBM having a membrane binding region. More than thirty kinds of monoclonal antibody were obtained. The results on several representative antibodies are shown in Table 1. As a result, it was found that most anti-human sOBM monoclonal antibodies which specifically recognize human sOBM also recognize the human intact OBM having a membrane binding region, but not the mouse OBM and the mouse intact OBM which has a membrane binding region. On the other hand, it was found that only a few monoclonal antibodies recognizing both the human sOBM and mouse sOBM were obtained and that these antibodies exhibit cross-reactivity to both the human OBM and mouse OBM. These results show that there are common antigen-recognizing sites, namely common epitopes, in both the human OBM and mouse OBM. Based on the fact that the anti-human sOBM monoclonal antibody prepared using the human sOBM as an immune antigen also equally recognizes human OBM having a membrane binding region, anti-human sOBM monoclonal antibody was named the anti-human OBM/sOBM monoclonal antibody.

TABLE 1

| Antibody | Antigen | | | |
|---|---|---|---|---|
| | hsOBM | hOBM | MsOBM | mOBM |
| H-OBM 1 | + | + | − | − |
| H-OBM 2 | + | + | − | − |
| H-OBM 3 | + | + | − | − |
| H-OBM 4 | + | + | − | − |
| H-OBM 5 | + | + | − | − |
| H-OBM 6 | + | + | − | − |
| H-OBM 7 | + | + | − | − |
| H-OBM 8 | + | + | − | − |
| H-OBM 9 | + | + | + | + |
| H-OBM 10 | + | + | − | − |
| H-OBM 11 | + | + | − | − |
| H-OBM 12 | + | + | − | − |

TABLE 1-continued

| Antibody | Antigen | | | |
|---|---|---|---|---|
| | hsOBM | hOBM | MsOBM | mOBM |
| H-OBM 13 | + | + | + | + |
| H-OBM 14 | + | + | − | − | hsOBM: human soluble OBM,
hOBM: human membrane bonding type OBM,
msOBM: mouse soluble OBM,
mOBM: mouse membrane bonding type OBM hs,OBM: human soluble OBM, hOBM: human membrance bonding type OBM, msOBM: mouse soluble OBM, mOBM: mouse membrance bonding type OBM.

Example 34

Determination of Class and Subclass of Monoclonal Antibody

The class and subclass of the monoclonal antibody of the present invention were determined by the immunoglobulin class and subclass analysis kit (Amersham Co.) according to the protocol indicated. The results on representative monoclonal antibodies are shown in Table 2. As shown in Table 2, the majority of anti-human OBM/sOBM monoclonal antibodies were $IgG_1$, the others were $IgG_{2a}$ and $IgG_{2b}$. Light chains for all antibodies were κ chains.

TABLE 2

| Antibody | $IgG_1$ | $IgG_{2a}$ | $IgG_{2b}$ | $IgG_3$ | IgA | κ |
|---|---|---|---|---|---|---|
| H-OBM 8 | − | + | − | − | − | + |
| H-OBM 9 | + | − | − | − | − | + |
| H-OBM 10 | + | − | − | − | − | + |
| H-OBM 11 | + | − | − | − | − | + |
| H-OBM 12 | − | − | + | − | − | + |
| H-OBM 13 | + | − | − | − | − | + |
| H-OBM 14 | + | − | − | − | − | + |

Example 35

Measurement of the Dissociation Constant ($K_d$ Value) of Monoclonal Antibody

The dissociation constant of the monoclonal antibody was measured according to a known method (Betrand Friguet et al.: Journal of Immunological Methods, 77, 305-319, 1986). That is, the purified antibody obtained in the Example 32 was diluted with 0.4 M Tris-HCl buffer (a primary buffer, pH 7.4) containing 40% Block Ace and 0.1% Polysorbate 20 to give a concentration of 5 ng/ml. The solution was mixed with an equivalent volume of a diluted solution of purified human soluble OBM (hsOBM) obtained in Example 28 in the primary buffer with a concentration range of 6.25 to 10 μg/ml. The mixture was allowed to stand for 15 hours at 4° C. to bind the hsOBM to the monoclonal antibody. After 15 hours, the antibody not bound to the hsOBM (10 μg/ml, 100 μl/well) was measured using an immobilized solid phase ELISA to calculate the dissociation constant of the monoclonal antibody to the hsOBM. In addition, affinity to msOBM of an antibody, which is a monoclonal antibody for the hsOBM and also exhibits the cross-reactivity to mouse soluble OBM (msOBM), was measured according to the same method except for using msOBM instead of the hsOBM. Dissociation constant of antibodies, which exhibit high affinity to each antigen and are useful for enzymatic immunoassay and binding assay, are shown in Table 3.

TABLE 3

| Antibody | Subclass | Antigen | Dissociation constant Kd(M) |
|---|---|---|---|
| H-OBM 1 | $IgG_1(κ)$ | hsOBM | $1 \times 10^{-11} < kd < 1 \times 10^{-10}$ |
| H-OBM 4 | $IgG_1(κ)$ | hsOBM | $1 \times 10^{-11} < kd < 1 \times 10^{-10}$ |
| H-OBM 9 | $IgG_1(κ)$ | hsOBM | $1 \times 10^{-9} < kd < 1 \times 10^{-8}$ |
| H-OBM 9 | $IgG_1(κ)$ | msOBM | $1 \times 10^{-8} < kd < 1 \times 10^{-7}$ |

As a result, the dissociation constants (Kd) of H-OBM 1 and H-OBM 4 which are the antibodies specific to human soluble OBM (hsOBM) were in the order of $10^{-11}$ M, indicating the high affinity to hsOBM. On the other hand, the Kd value of the antibody H-OBM 9 which recognizes both the hsOBM and mouse soluble OBM (msOBM) was in the order of $10^{-8}$ M to msOBM and in the order of $10^{-9}$ M to hsOBM. In addition, the dissociation constant of the other antibody which recognizes both antigens in the Table 1, i.e. the dissociation constant of H-OBM 13 for each antigen, was the same as that of H-OBM 9, and-these two antibodies belong to the same subclass. These findings suggest the possibility that they are the identical antibodies which recognize the same epitope of each antigen.

Example 36

Measuring Method of Human OBM and sOBM by Sandwich ELISA Using Anti-human OBM/sOBM Monoclonal Antibodies A sandwich ELISA was constructed using the two high affinity monoclonal antibodies obtained in Example 35, H-OBM 1 and H-OBM 4, respectively as a solid phase antibody and an enzyme-labeled antibody. Labeling of the antibody was carried out using a maleimide activated-peroxidase kit (Piers Co.). The antibody, H-OBM 1, was dissolved in a 0.1 M sodium bicarbonate solution to a concentration of 10 μg/ml, and 100 μl of the solution was added to each well in 96-well immunoplates (Nunc company). After being allowed to stand overnight at 4° C. to immobilize the antibody, the solution was discarded and 300 μl of 50% Block Aces solution was added to each well in the plates. Each well in the plates was blocked by allowing to stand at room temperature for two hours. After blocking, the plates were washed with phosphate buffered saline containing 0.1% Polysorbate 20 (PBS-P). Human OBM (hOBM) and human soluble OBM (hsOBM) were respectively diluted with 0.4 M Tris-HCl buffer, pH 7.4, containing 40% Block Ace™ (Snow Brand Milk Products Co., Ltd.) and 0.1% Polysorbate 20 (Wako Pure Chemicals Co., Ltd.) (the first reaction buffer) to prepare test samples with various concentrations. These test samples with different concentrations were added to each well in the amount of 100 μl per well and reacted to the antibody, H-OBM 1 immobilized on each well by incubating at room temperature for two hours. After two hours, the plates were washed with PBS-P. Next, 100 μl of a solution of POD-labeled H-OBM 4 antibody in 0.2 M Tris-HCl buffer, pH 7.4, containing 25% Block Acem and 0.1% Polysorbate 20 (the second reaction buffer) was added to each well, followed by further incubating at room temperature for two hours. The plates were then washed with PBS-P and 100 μl of an enzyme substrate solution (TMB, ScyTek Co.) was added to each well to start enzyme reaction. The enzyme reaction was terminated by the addition of 100 μl of a reaction termination solution (stopping reagent, ScyTek Co.) to each well. The absorbance of each well at 450 nm was measured using a microplate reader. The results are shown in FIG. 27.

As a result, it was confirmed that the sandwich ELISA constructed using the two anti-human OBM/sOBM monoclonal antibodies, H-OBM 1 and H-OBM 4 with high affinity for human OBM/sOBM prepared in the Example 35, equally recognizes human OBM and human sOBM, and is able to measure a very small amount of human OBM or human sOBM at a quantitative limit of about $1.25 \times 10^{-3}$ to $2.5 \times 10^{-3}$ pmol/ml (about 50-100 pg/ml for human OBM with a molecular weight of 40 kDa, about 40-80 pg/ml for human sOBM with a molecular weight of 32 kDa). The hybridomas which produce these two anti-human OBM/sOBM monoclonal antibodies, H-OBM 1 and H-OBM 4 were named H-OBM1 and H-OBM4, respectively. The hybridoma producing anti-human OBM/sOBM monoclonal antibody (H-OBM 9) which recognizes mouse OBM and mouse sOBM and also has an osteoclast formation-inhibitory activity was named H-OBM9. These hybridomas were deposited with the National Institute of Bioscience and Human Technology, the Agency-of Industrial Science and Technology, on Nov. 5, 1993 with Deposition Nos. FERMBP-6264 (H-OBM1), FERMBP-6265 (H-OBM 4), and FERM BP-6266 (H-OBM 9).

Example 37

Measurement of Mouse OBM and Mouse sOBM Using Anti-human OBM/sOBM Monoclonal Antibodiy which Recognizes Mouse OBM and Mouse sOBM A sandwich ELISA was constructed using the anti-human OBM/sOBM monoclonal antibody, H-OBM 9, which recognizes mouse OBM and mouse sOBM obtained as an solid phase antibody in the Examples 33 and 35, and the anti-mouse OBM/sOBM polyclonal antibody as an enzyme-labeled antibody obtained in the example 28. The mouse OBM and mouse sOBM were respectively diluted with the first reaction buffer to give various concentrations in the same manner as in the Example 35 and then measured sOBM according to the method described in the Example 36. The results are shown in FIG. 28. As a result, it was found that mouse OBM and mouse sOBM can be similarly measured using H-OBM 9 which is the anti-human OBM/sOBM monoclonal antibody recognizing the mouse OBM and mouse sOBM of the present invention. As shown by the result of Example 35, this anti-human OBM/sOBM monoclonal antibody H-OBM 9 has a high dissociation constant relative to the mouse sOBM, namely it has a comparatively low affinity to mouse sOBM. The sensitivity in the measurement of mouse OBM (molecular weight, about 40 kDa) and mouse sOBM (molecular weight, about 32 kDa) by this ELISA assay was about $25 \times 10^{-3}$ pmol/ml (about 1 ng/ml for mouse OBM and about 0.8 ng/ml for mouse sOBM).

Example 38

Osteoclastogenesis-inhibitory Activity of Anti-OBM/sOBM Antibody

It is known that osteoclast-like cells (OCL) are induced by co-culture of mouse spleen cells and ST2 cells (mouse bone marrow-derived stromal cells; Endocrinology, 125, 1805-1813 (1989)). Capability of the anti-OBM/sOBM antibody to inhibit the OCL formation when added to the co-culture system was studied. Because the mouse OBM is expressed in this co-culture system, a rabbit anti-mouse OBM/sOBM polyclonal antibody which recognizes mouse OBM and an anti-human OBM/sOBM monoclonal antibody (H-OBM 9) which recognizes both human OBM and mouse OBM antigens were used as the antibodies in this example. Seven hundred microliters per well of each anti-OBM antibody diluted serially with α-MEM containing 10% FCS and 350 µl/well of male mouse splenocytes ($2 \times 10^6$/ml) suspended in the same medium described above were added to each well in a 24-well plate (Nunc). Next, ST2 cells trypsinized and suspended in the above-mentioned culture medium containing $4 \times 10^{-8}$ M Vitamin $D_3$ and $4 \times 10^{-7}$ M Dexamethazone ($8 \times 10^4$ cells/ml) were added to each well in the amount of 350 µl/well, followed by culturing for six days at 37° C. After the plates were washed once with PBS, cells in each well were fixed with a mixture of ethanol and acetone (50:50) for one hour at room temperature. The plates were dried in air, and 500 µl of substrate solution was added to each well according to the protocol of the LEUKOCYTE ACID PHOSPHATASE kit (Sigma Co.), followed by incubating for 55 minutes at 37° C. Only the cells exhibiting the tartaric acid-resistant acid phophatase activity (TRAP activity), which is a specific marker for osteoclasts, were stained by this reaction. The plates were washed once with distilled water and dried in air, and the number of TRAP-positive cells was counted. The results are shown in Table 4. As shown in Table 4, both the rabbit anti-mouse OBM/sOBM polyclonal antibody and the anti-human OBM/sOBM monoclonal antibody, H-OBM 9, which recognizes mouse OBM inhibited OCL formation in a dose-dependent manner. These antibodies were found to possess osteoclastogenesis-inhibitory activity like osteoclastogenesis-inhibitory factor, OCIF/OPG, and thus are promising as a therapeutic agent for treating bone metabolism abnormality symptoms.

TABLE 4

| | Number of TRAP-positive multinucleates | |
| --- | --- | --- |
| Amount of antibody (µg/ml) | Rabbit anti-mouse OBM/sOBM polyclonal antibody | Mouse anti-human OBM/sOBM monoclonal antibody (H-OBM 9) |
| 0 | 1155 ± 53 | 1050 ± 45 |
| 10 | 510 ± 24 | 650 ± 25 |
| 100 | 10 ± 3 | 15 ± 4 |

(Average ± standard deviation, n = 3)

Example 39

Human Osteoclast Formation-inducing Activity of Trx-OBM

Mononuclear cells were prepared from whole blood collected from the vein of a healthy adult by density gradient using Histopaque (Sigma Co.) according to the protocol attached thereto. The mononuclear cells were suspended at a cell density of $1.3 \times 10^6$/ml in α-MEM containing $10^{-7}$ M Dexamethasone, 200 ng/ml macrophage colony stimulating factor (The Green Cross Corp.), 10% fetal bovine serum, and purified Trx-OBM (0-100 ng/ml) obtained in Example 15. The cell suspension was added to each well in 48-well plates in the amount of 300 µl per well, and the cells were cultured at 37° C. for three days. After the culture broth was replaced with the above-mentioned culture medium, the cells were cultured at 37° C. for four days. The cultured cells having tartaric acid resistant acid phosphatase activity (TRAP activity) were selectively stained according to the method described in Example 5. The number of stained multinucleates was measured by microscope observation. The results are shown in FIG. 29. It was confirmed that TRAP-positive multinucleates were induced in a dose dependent manner by addition of Trx-OBM, while no TRAP-positive cells were detected in the wells to which Trx-OBM was not added. Moreover, these TRAP-positive multinucleates were found positive to vitronectin receptor which is a marker for osteoclasts. Furthermore, when similar cell culture was carried out on ivory slices placed on each well in a 48-well plate, pit formation was observed on the ivory slices only in the presence of Trx-OBM. Based on these findings, Trx-OBM was formed to have the activity of inducing human osteoclast formation.

Example 40

Inhibition of Bone Resorbing Activity by Anti-OBM/sOBM Antibody $^{45}$Ca—CaCl$_2$ solution (Amersham Co.) was subcutaneously injected into a ddY mouse (Japan SLC Co.) in the 15th day of pregnancy at a dose of 25 µCi per mouse to label the bone of the fetus with $^{45}$Ca. Next day, the mouse was sacrificed to obtain the fetus. The forefoot of the fetus was drawn and the skin and muscle were removed to obtain the long bones. The cartilage was removed to obtain the shafts of long bones. The shafts of long bones were floated one by one in 0.5 ml of culture medium (BGJb medium (GIBCO BRL company) containing a 0.2% bovine serum albumin (Sigma Co.)) in each well in 24-well plates, and cultured for 24 hours at 37° C. in 5% $CO_2$. After the pre-cultivation, the bones were transferred into various fresh culture media (0.5 ml), each containing one of four different bone resorbing factors (vitamin $D_3$, prostaglandins $E_2$, parathyroid hormone, interleukin 1α), and normal rabbit IgG (100 µg/ml; as a control), or the rabbit anti-OBM/sOBM polyclonal antibody prepared in Example 28, followed by further cultivation for 72 hours. After the cultivation, the long bones were placed in 0.5 ml of an aqueous solution of 5% trichloroacetic acid (Wako Pure Chemicals Co., Ltd.), and allowed to stand at room temperature for more than 3 hours to decalcify. Five ml of a scintillator (AQUASOL-2, PACKARD Co.) was added to the culture broth and the extract of the trichloroacetic acid solution (each 0.5 ml) to measure the radioactivity of $^{45}$Ca, whereby the ratio of the $^{45}$Ca which was liberated into the culture broth by bone resorption was calculated. The results are shown in FIGS. 30 to 33. As a result, vitamin $D_3$ ($10^{-8}$ M) was found to increase the bone resorbing activity, but the rabbit anti-OBM/sOBM polyclonal antibody suppressed the bone resorption stimulated by vitamin $D_3$ in a concentration-dependent manner, completely inhibiting the increased bone resorption at a concentration of 100 µg/ml (FIG. 30). Prostaglandins $E_2$ ($10^{-6}$ M) and parathyroid hormone (100 ng/ml) also increased the bone resorbing activity. However, addition of 100 µg/ml of the rabbit anti-OBM/sOBM polyclonal antibody almost completely inhibited the bone resorption stimulated by prostaglandins $E_2$ and parathyroid hormone (FIGS. 31 and 32). On the other hand, normal rabbit IgG (100 µg/ml), which was used as a positive control, did not affect the bone resorbing activity induced by prostaglandins $E_2$ and parathyroid hormone. Bone resorption was also increased by interleukin 1α (10 ng/ml), but significantly inhibited by the addition of rabbit anti-OBM/sOBM polyclonal antibody (100 µg/ml) (FIG. 33). Based on these results, it is clear that the antibody of the present invention is a superior substance as a bone resorption inhibitor. The results obtained by similar experiment using H-OBM 9, which is a mouse anti-human OBM/sOBM antibody, confirmed that this antibody exhibits an almost equivalent bone resorption-inhibitory effect as the rabbit anti-OBM/sOBM polyclonal antibody.

INDUSTRIAL APPLICABILITY

The present invention provides a novel protein that specifically binds to osteoclastogenesis-inhibitory factor (OCIF), a process for preparing the protein, a screening method for a substance which controls expression of this protein using this protein, a screening method for a substance which inhibits or modulates the activity of this protein, a screening method for the receptor which transmits the activity of this protein by binding thereto, a pharmaceutical composition which contains the substance obtained by these screening methods, an antibody for the said protein, and an agent for treating bone metabolism abnormality using the antibody.

Moreover, the present invention provides a DNA encoding a novel protein (OCIF-binding molecule) which binds to osteoclastogenesis-inhibitory factor (OCIF), a protein which possesses an amino acid sequence encoded by the DNA, a method for preparing the protein specifically binding to OCIF using said DNA by a genetic engineering technique, and an agent comprising said protein for treating bone metabolism acatastasia. Furthermore, the present invention provides a screening method for a substance which controls expression of the OCIF-binding molecule, a screening method for a substance which inhibits or modulates the activity of the OCIF-binding molecule by binding thereto, a screening method for the receptor which transmits the activity of the OCIF-binding molecule by binding thereto, and a pharmaceutical composition which contains the substance obtained by these screening methods.

Still further, the present invention provides a DNA encoding a novel human protein capable of binding to osteoclastogenesis-inhibitory factor, OCIF (human OCIF-binding molecule, human OBM), a protein containing an amino acid sequence encoded by the DNA, a process for preparing a protein having characteristics of specifically binding to OCIF and exhibiting a biological activity to support and promote the osteoclast differentiation and maturation by means of genetic engineering technique, and an agent for treating bone metabolism abnormality using the protein. Furthermore, the present invention provides a screening method for a substance which controls expression of the OCIF-binding molecule, a screening method for a substance which inhibits or modulates the activity of the OCIF-binding molecule by binding thereto, a screening method for the receptor which transmits the biological activity of the OCIF-binding molecule by binding thereto, a pharmaceutical composition which contains the substance obtained by these screening methods, an antibody to human OCIF-binding protein, and an agent for preventing and/or treating bone metabolism abnormality symptoms using the antibody.

In addition, the present invention provides antibodies which recognize both antigens (anti-OBM/sOBM antibodies), one is a membrane-bound protein which specifically binds to OCIF (OCIF binding molecule; OBM) and the other a soluble OBM (sOBM) which does not have a membrane binding region, a process for preparing the antigen, a method for measuring the OBM and sOBM using these antibodies, and an agent for preventing and/or treating bone metabolism abnormality symptoms using the antibody as an effective component.

The protein and antibody prepared by the process of the present invention are useful as medicines and/or reagents for research and test purposes.

Description of Deposited Microorganisms (1) Name and address of the depository organization to which microorganism was deposited
  Agency of Industrial Science and Technology 1-3, Higashi 1-Chome, Tsukuba-shi, Ibaraki-ken, Japan (postal code 305)
  Date of deposition to the depository organization
  May 23, 1997
  The deposition number
  FERM BP-5953

(2) Name and address of the depository organization to which microorganism was deposited
  Agency of Industrial Science and Technology 1-3, Higashi 1-Chome, Tsukuba-shi, Ibaraki-ken, Japan (postal code 305)
  Date of deposition to the depository organization
  Aug. 13, 1997
  The deposition number
  FERM BP-6058

(3) Name and address of the depository organization to which microorganism was deposited
  Agency of Industrial Science and Technology 1-3, Higashi 1-Chome, Tsukuba-shi, Ibaraki-ken, Japan (postal code 305)
  Date of deposition to the depository organization
  Nov. 5, 1997 (Original deposition date)
  The deposition number
  FERM BP-6264

(4) Name and address of the depository organization to which microorganism was deposited
  Agency of Industrial Science and Technology 1-3, Higashi 1-Chome, Tsukuba-shi, Ibaraki-ken, Japan (postal code 305)
  Date of deposition to the depository organization
  Nov. 5, 1997 (Original deposition date)
  The deposition number
  FEPM BP-6265

(5) Name and address of the depository organization to which microorganism was deposited
  Agency of Industrial Science and Technology 1-3, Higashi 1-Chome, Tsukuba-shi, Ibaraki-ken, Japan (postal code 305)
  Date of deposition to the depository organization
  Nov. 5, 1997 (Original deposition date)
  The deposition number
  FERM BP-6266

Sequence ID No. 1
Sequence Length: 316
Sequence Type: amino acid
Strandedness: 1
Topology: linear
Molecule Type: protein
Sequence:

```
Met Arg Arg Ala Ser Arg Asp Tyr Gly Lys Tyr Leu
 1               5                   10
Arg Ser Ser Glu Glu Met Gly Ser Gly Pro Gly Val
            15                  20
Pro His Glu Gly Pro Leu His Pro Ala Pro Ser Ala
25                  30                  35
Pro Ala Pro Ala Pro Pro Pro Ala Ala Ser Arg Ser
        40                  45
Met Phe Leu Ala Leu Leu Gly Leu Gly Leu Gly Gln
    50                  55                  60
Val Val Cys Ser Ile Ala Leu Phe Leu Tyr Phe Arg
                65                  70
Ala Gln Met Asp Pro Asn Arg Ile Ser Glu Asp Ser
        75                  80
Thr His Cys Phe Tyr Arg Ile Leu Arg Leu His Glu
85                  90                  95
Asn Ala Gly Leu Gln Asp Ser Thr Leu Glu Ser Glu
            100                 105
Asp Thr Leu Pro Asp Ser Cys Arg Arg Met Lys Gln
    110                 115                 120
Ala Phe Gln Gly Ala Val Gln Lys Glu Leu Gln His
                125                 130
Ile Val Gly Pro Gln Arg Phe Ser Gly Ala Pro Ala
        135                 140
Met Met Glu Gly Ser Trp Leu Asp Val Ala Gln Arg
145                 150                 155
Gly Lys Pro Glu Ala Gln Pro Phe Ala His Leu Thr
            160                 165
Ile Asn Ala Ala Ser Ile Pro Ser Gly Ser His Lys
    170                 175                 180
Val Thr Leu Ser Ser Trp Tyr His Asp Arg Gly Trp
                185                 190
Ala Lys Ile Ser Asn Met Thr Leu Ser Asn Gly Lys
        195                 200
Leu Arg Val Asn Gln Asp Gly Phe Tyr Tyr Leu Tyr
205                 210                 215
Ala Asn Ile Cys Phe Arg His His Glu Thr Ser Gly
                220                 225
Ser Val Pro Thr Asp Tyr Leu Gln Leu Met Val Tyr
        230                 235                 240
Val Val Lys Thr Ser Ile Lys Ile Pro Ser Ser His
                245                 250
Asn Leu Met Lys Gly Gly Ser Thr Lys Asn Trp Ser
            255                 260
Gly Asn Ser Glu Phe His Phe Tyr Ser Ile Asn Val
265                 270                 275
Gly Gly Phe Phe Lys Leu Arg Ala Gly Glu Glu Ile
                280                 285
Ser Ile Gln Val Ser Asn Pro Ser Leu Leu Asp Pro
        290                 295                 300
Asp Gln Asp Ala Thr Tyr Phe Gly Ala Phe Lys Val
                305                 310
Gln Asp Ile Asp
315 316
```

Sequence ID No. 2
Sequence Length: 1538
Sequence Type: nucleic acid
Strandedness: 1
Topology: linear
Molecule Type: cDNA to mRNA Sequence:

```
GCCAGGACCT CTGTGAACCG GTCGGGCGG GGGCCGCCTG GCCGGGAGTC TGCTCGGCGG      60
TGGGTGGCCG AGGAAGGGAG AGAACGATCG CGGAGCAGGG CGCCCGAACT CCGGGCGCCG    120
CGCCATGCGC CGGGCCAGCC GAGACTACGG CAAGTACCTG CGCAGCTCGG AGGAGATGGG    180
CAGCGGCCCC GGCGTCCCAC ACGAGGGTCC GCTGCACCCC GCGCCTTCTG CACCGGCTCC    240
GGCGCCGCCA CCCGCCGCCT CCCGCTCCAT GTTCCTGGCC CTCCTGGGGC TGGGACTGGG    300
CCAGGTGGTC TGCAGCATCG CTCTGTTCCT GTACTTTCGA GCGCAGATGG ATCCTAACAG    360
AATATCAGAA GACAGCACTC ACTGCTTTTA TAGAATCCTG AGACTCCATG AAAACGCAGG    420
TTTGCAGGAC TCGACTCTGG AGAGTGAAGA CACACTACCT GACTCCTGCA GGAGGATGAA    480
ACAAGCCTTT CAGGCGGCCG TGCAGAAGGA ACTGCAACAC ATTGTGGGGC CACAGCGCTT    540
CTCAGGAGCT CCAGCTATGA TGGAAGGCTC ATGGTTGGAT GTGGCCCAGC GAGGCAAGCC    600
TGAGGCCCAG CCATTTGCAC ACCTCACCAT CAATGCTGCC AGCATCCCAT CGGGTTCCCA    660
TAAAGTCACT CTGTCCTCTT GCTACCACGA TCGAGGCTGG GCCAAGATCT CTAACATGAC    720
GTTAAGCAAC GGAAAACTAA GCGTTAACCA AGATGGCTTC TATTACCTGT ACGCCAACAT    780
TTGCTTTCGG CATCATGAAA CATCGGGAAG CGTACCTACA GACTATCTTC AGCTGATGGT    840
GTATGTCGTT AAAACCAGCA TCAAAATCCC AAGTTCTCAT AACCTGATGA AAGGAGGGAG    900
CACGAAAAAC TGGTCGGGCA ATTCTGAATT CCACTTTTAT TCCATAAATG TTGGGGGATT    960
TTTCAAGCTC CGAGCTGGTG AAGAAATTAG CATTCAGGTG TCCAACCCTT CCCTGCTCGA   1020
TCCGGATCAA GATGCGACGT ACTTTGGGGC TTTCAAAGTT CAGGACATAG ACTGAGACTC   1080
ATTTCGTGGA ACATTAGCAT GGATGTCCTA GATGTTTGGA AACTTCTTAA AAAATGGATG   1140
ATGTCTATAC ATGTGTAAGA CTACTAAGAG ACATGCCCCA CGGTGTATGA AACTCACAGC   1200
CCTCTCTCTT GAGCCTGTAC AGGTTGTGTA TATGTAAAGT CCATAGGTGA TGTTAGATTC   1260
ATGGTGATTA CACAACGGTT TTACAATTTT GTAATGATTT CCTAGAATTG AACCAGATTG   1320
GGAGAGGTAT TCCGATGCTT ATGAAAAACT TACACGTGAG CTATGGAAGG GGGTCACAGT   1380
CTCTGGGTCT AACCCCTGGA CATGTQCCAC TGAGAACCTT GAAATTAAGA GGATGCCATG   1440
TCATTGCAAA GAAATGATAG TGTGAAGGGT TAAGTTCTTT TGAATTGTTA CATTGCGCTG   1500
GGACCTGCAA ATAAGTTCTT TTTTTCTAAT GAGGAGAG                           1538
```

Sequence ID No. 3
Sequence Length: 21
Sequence Type: nucleic acid
Strandedness: 1
Topology: linear
Molecule Type: other nucleic acid (synthetic DNA)
Sequence:

```
     AAACGCAAAA AACCAGAAAG G              21
```

Sequence ID No. 4
Sequence Length: 17
Sequence Type: nucleic acid
Strandedness: 1
Topology: linear
Molecule Type: other nucleic acid (synthetic DNA)
Sequence:

```
     GTAAAACGAC GGCCAGT                   17
```

Sequence ID No. 5
Sequence Length: 17
Sequence Type: nucleic acid
Strandedness: 1
Topology: linear
Molecule Type: other nucleic acid (synthetic DNA)
Sequence:

```
     CAGGAAACAG CTATGAC                   17
```

Sequence ID No. 6
Sequence Length: 22
Sequence Type: nucleic acid
Strandedness: 1
Topology: linear
Molecule Type: other nucleic acid (synthetic DNA)
Sequence:

```
     AAGCCCCAAA GTACGTCGCA TC             22
```

Sequence ID No. 7
Sequence Length: 26
Sequence Type: nucleic acid
Strandedness: 1
Topology: linear
Molecule Type: other nucleic acid (synthetic DNA)
Sequence:

```
         CGAAGCTTTC GAGCGCAGAT GGATCC            26
```

Sequence ID No. 8
Sequence Length: 27
Sequence Type: nucleic acid
Strandedness: 1
Topology: linear
Molecule Type: other nucleic acid (synthetic DNA)
Sequence:

```
         CCTCTAGAGT CTATGTCCTG AAGTTTG           27
```

Sequence ID No. 9
Sequence Length: 20
Sequence Type: nucleic acid
Strandedness: 1
Topology: linear
Molecule Type: other nucleic acid (synthetic DNA)
Sequence:

```
         ATCAGAAGAC AGCACTCACT                   20
```

Sequence ID No. 10
Sequence Length: 33
Sequence Type: nucleic acid
Strandedness: 1
Topology: linear
Molecule Type: other nucleic acid (synthetic DNA)
Sequence:

```
         GGGGTCGACC TAGGACATCC ATGCTAATGT TCC    33
```

Sequence ID No. 11
Sequence Length: 317
Sequence Type: amino acid
Strandedness: 1
Topology: linear
Molecule Type: protein
Sequence:

```
Met Arg Arg Ala Ser Arg Asp Tyr Thr Lys Tyr Leu
                 5                  10
Arg Gly Ser Glu Glu Met Gly Gly Pro Gly Ala
             15                  20
Pro His Glu Gly Pro Leu His Ala Pro Pro Pro
25                  30                  35
Ala Pro His Gln Pro Pro Ala Ala Ser Arg Ser Met
                 40                  45
Phe Val Ala Leu Leu Gly Leu Gly Leu Gly Gln Val
50                  55                  60
Val Cys Ser Val Ala Leu Phe Phe Tyr Phe Arg Ala
                 65                  70
```

-continued

```
Gln Met Asp Pro Asn Arg Ile Ser Glu Asp Gly Thr
                 75                  80
His Cys Ile Tyr Arg Ile Leu Arg Leu His Glu Asn
85                  90                  95
Ala Asp Phe Gln Asp Thr Thr Leu Glu Ser Gln Asp
                 100                 105
Thr Lys Leu Ile Pro Asp Ser Cys Arg Arg Ile Lys
             110                 115                 120
Gln Ala Phe Gln Gly Ala Val Gln Lys Glu Leu Gln
                 125                 130
His Ile Val Gly Ser Gln His Ile Arg Ala Glu Lys
                 135                 140
Ala Met Val Asp Gly Ser Trp Leu Asp Leu Ala Lys
145                 150                 155
Arg Ser Lys Leu Glu Ala Gln Pro Phe Ala His Leu
                 160                 165
Thr Ile Asn Ala Thr Asp Ile Pro Ser Gly Ser His
                 170                 175                 180
Lys Val Ser Leu Ser Ser Trp Tyr His Asp Arg Gly
                         185                 190
Trp Ala Lys Ile Ser Asn Met Thr Phe Ser Asn Gly
                 195                 200
Lys Leu Ile Val Asn Gln Asp Gly Phe Tyr Tyr Leu
205                 210                 215
Tyr Ala Asn Ile Cys Phe Arg His His Glu Thr Ser
                 220                 225
Gly Asp Leu Ala Thr Glu Tyr Leu Gln Leu Met Val
                 230                 235                 240
Tyr Val Thr Lys Thr Ser Ile Lys Ile Pro Ser Ser
                         245                 250
His Thr Leu Met Lys Gly Gly Ser Thr Lys Tyr Trp
                 255                 260
Ser Gly Asn Ser Glu Phe His Phe Tyr Ser Ile Asn
265                 270                 275
Val Gly Gly Phe Phe Lys Leu Arg Ser Gly Glu Glu
                 280                 285
Ile Ser Ile Glu Val Ser Asn Pro Ser Leu Leu Asp
             290                 295                 300
Pro Asp Gln Asp Ala Thr Tyr Phe Gly Ala Phe Lys
                 305                 310
Val Arg Asp Ile Asp
             315
```

Sequence ID No. 12
Sequence Length: 954
Sequence Type: nucleic acid
Strandedness: 1
Topology: linear
Molecule Type: cDNA to mRNA Sequence:

```
ATGCGCCGCG CCAGCAGAGA CTACACCAAG TACCTGCGTG GCTCGGAGGA GATGGGCGGC   60
GGCCCCGGAG CCCCGCACGA GGGCCCCCTG CACGCCCCGC CGCCGCCTGC GCCGCACCAG  120
CCCCCTGCCG CCTCCCGCTC CATGTTCGTG GCCCTCCTGG GGCTGGGGCT GGGCCAGGTT  180
GTCTGCAGCG TCGCCCTGTT CTTCTATTTC AGAGCGCAGA TGGATCCTAA TAGAATATCA  240
GAAGATGGCA CTCACTGCAT TTATAGAATT TTGAGACTCC ATGAAAATGC AGATTTTCAA  300
GACACAACTC TGGAGAGTCA AGATACAAAA TTAATACCTG ATTCATGTAG GAGAATTAAA  360
CAGGCCTTTC AAGGAGCTGT GCAAAAGGAA TTACAACATA TCGTTGGATC ACAGCACATC  420
AGAGCAGAGA AAGCGATGGT GGATGGCTCA TGGTTAGATC TGGCCAAGAG GAGCAAGCTT  480
GAAGCTCAGC CTTTTGCTCA TCTCACTATT AATGCCACCG ACATCCCATC TGGTTCCCAT  540
AAAGTGAGTC TGTCCTCTTG GTACCATGAT CGGGGTTGGG CCAAGATCTC CAACATGACT  600
TTTAGCAATG GAAAACTAAT AGTTAATCAG GATGGCTTTT ATTACCTGTA TGCCAACATT  660
TGCTTTCGAC ATCATGAAAC TTCAGGAGAC CTAGCTACAG AGTATCTTCA ACTAATGGTG  720
TACGTCACTA AAACCAGCAT CAAAATCCCA AGTTCTCATA CCCTGATGAA AGGAGGAAGC  780
ACCAAGTATT GGTCAGGGAA TTCTGAATTC CATTTTTATT CCATAAACGT TGGTGGATTT  840
TTTAAGTTAC GGTCTGGAGA GGAAATCAGC ATCGAGGTCT CCAACCCCTC CTTACTGGAT  900
CCGGATCAGG ATGCAACATA CTTTGGGGCT TTTAAAGTTC GAGATATAGA TTGA        954
```

Sequence ID No. 13
Sequence Length: 27
Sequence Type: nucleic acid
Strandedness: 1
Topology: linear
Molecule Type: other nucleic acid (synthetic DNA)
Sequence:

```
         GGCGTACGCA GAGCGCAGAT GGATCCT           27
```

Sequence ID No. 14
Sequence Length: 34
Sequence Type: nucleic acid
Strandedness: 1
Topology: linear
Molecule Type: other nucleic acid (synthetic DNA)
Sequence:

```
         GGGGTCGACC ATCCAGGAAA TATCATAACA CTCC       34
```

Sequence ID No. 15
Sequence Length: 951
Sequence Type: nucleic acid
Strandedness: 1
Topology: linear
Molecule Type: cDNA to mRNA
Sequence:

```
ATGCGCCGGG CCAGCCGAGA CTACGGCAAG TACCTGCGCA GCTCGGAGGA GATGGGCAGC   60
GGCCCCGGCG TCCCACACGA GGGTCCGCTG CACCCCGCGC CTTCTGCACC GGCTCCGGCG  120
CCGCCACCCG CCGCCTCCCG CTCCATGTTC CTGGCCCTCC TGGGGCTGGG ACTGGGCCAG  180
GTGGTCTGCA GCATCGCTCT GTTCCTGTAC TTTCGAGCGC AGATGGATCC TAACAGAATA  240
TCAGAAGACA GCACTCACTG CTTTTATAGA ATCCTGAGAC TCCATGAAAA CGCAGGTTTG  300
CAGGACTCGA CTCTGGAGAG TGAAGACACA CTACCTGACT CCTGCAGGAG GATGAAACAA  360
GCCTTTCAGG GGGCCGTGCA GAAGGAACTG CAACACATTG TGGGGCCACA GCGCTTCTCA  420
GGAGCTCCAG CTATGATGGA AGGCTCATGG TTGGATGTGG CCCAGCGAGG CAAGCCTGAG  480
GCCCAGCCAT TTGCACACCT CACCATCAAT GCTGCCAGCA TCCCATCGGG TTCCCATAAA  540
GTCACTCTGT CCTCTTGGTA CCACGATCGA GGCTGGGCCA AGATCTCTAA CATGACGTTA  600
AGCAACGGAA AACTAAGGGT TAACCAAGAT GGCTTCTATT ACCTGTACGC CAACATTTGC  660
TTTCGGCATC ATGAAACATC GGGAAGCGTA CCTACAGACT ATCTTCAGCT GATGGTGTAT  720
```

```
GTCGTTAAAA CCAGCATCAA AATCCCAAGT TCTCATAACC TGATGAAAGG AGGGAGCACG   780

AAAAACTGGT CGGGCAATTC TGAATTCCAC TTTTATTCCA TAAATGTTGG GGGATTTTTC   840

AAGCTCCGAG CTGGTGAAGA AATTAGCATT CAGGTGTCCA ACCCTTCCCT GCTGGATCCG   900

GATCAAGATG CGACGTACTT TGGGGCTTTC AAAGTTCAGG ACATAGACTG A             951
```

Sequence ID No. 16
Sequence Length: 244
Sequence Type: amino acid
Strandedness: 1
Topology: linear
Molecule Type: protein
Sequence:

```
Ala Gln Met Asp Pro Asn Arg Ile Ser Glu Asp Ser
  1               5                  10

Thr His Cys Phe Tyr Arg Ile Leu Arg Leu His Glu
             15                  20

Asn Ala Gly Leu Gln Asp Ser Thr Leu Glu Ser Glu
 25                  30                  35

Asp Thr Leu Pro Asp Ser Cys Arg Arg Met Lys Gln
             40                  45

Ala Phe Gln Gly Ala Val Gln Lys Glu Leu Gln His
 50                  55                  60

Ile Val Gly Pro Gln Arg Phe Ser Gly Ala Pro Ala
             65                  70

Met Met Glu Gly Ser Trp Leu Asp Val Ala Gln Arg
 75                  80

Gly Lys Pro Glu Ala Gln Pro Phe Ala His Leu Thr
 85                  90                  95

Ile Asn Ala Ala Ser Ile Pro Ser Gly Ser His Lys
            100                 105

Val Thr Leu Ser Ser Trp Tyr His Asp Arg Gly Trp
            110                 115                 120

Ala Lys Ile Ser Asn Met Thr Leu Ser Asn Gly Lys
            125                 130

Leu Arg Val Asn Gln Asp Gly Phe Tyr Tyr Leu Tyr
            135                 140

Ala Asn Ile Cys Phe Arg His His Glu Thr Ser Gly
 145                 150                 155

Ser Val Pro Thr Asp Tyr Leu Gln Leu Met Val Tyr
            160                 165

Val Val Lys Thr Ser Ile Lys Ile Pro Ser Ser His
            170                 175                 180

Asn Leu Met Lys Gly Gly Ser Thr Lys Asn Trp Ser
            185                 190

Gly Asn Ser Glu Phe His Phe Tyr Ser Ile Asn Val
            195                 200

Gly Gly Phe Phe Lys Leu Arg Ala Gly Glu Glu Ile
 205                 210                 215

Ser Ile Gln Val Ser Asn Pro Ser Leu Leu Asp Pro
            220                 225

Asp Gln Asp Ala Thr Tyr Phe Gly Ala Phe Lys Val

Gln Asp Ile Asp
            235                 240
```

Sequence ID No. 17
Sequence Length: 246
Sequence Type: amino acid
Strandedness: 1
Topology: linear
Molecule Type: protein
Sequence:

```
Ala Gln Met Asp Pro Asn Arg Ile Ser Glu Asp Gly
  1               5                  10

Thr His Cys Ile Tyr Arg Ile Leu Arg Leu His Glu
             15                  20

Asn Ala Asp Phe Gln Asp Thr Thr Leu Glu Ser Gln
 25                  30                  35

Asp Thr Lys Leu Ile Pro Asp Ser Cys Arg Arg Ile
             40                  45

Lys Gln Ala Phe Gln Gly Ala Val Gln Lys Glu Leu
 50                  55                  60

Gln His Ile Val Gly Ser Gln His Ile Arg Ala Glu
             65                  70

Lys Ala Met Val Asp Gly Ser Trp Leu Asp Leu Ala
 75                  80

Lys Arg Ser Lys Leu Glu Ala Gln Pro Phe Ala His
 85                  90                  95

Leu Thr Ile Asn Ala Thr Asp Ile Pro Ser Gly Ser
            100                 105

His Lys Val Ser Leu Ser Ser Trp Tyr His Asp Arg
            110                 115                 120

Gly Trp Ala Lys Ile Ser Asn Met Thr Phe Ser Asn
            125                 130

Gly Lys Leu Ile Val Asn Gln Asp Gly Phe Tyr Tyr
            135                 140

Leu Tyr Ala Asn Ile Cys Phe Arg His His Glu Thr
 145                 150                 155

Ser Gly Asp Leu Ala Thr Glu Tyr Leu Gln Leu Met
            160                 165

Val Tyr Val Thr Lys Thr Ser Ile Lys Ile Pro Ser
            170                 175                 180

Ser His Thr Leu Met Lys Gly Gly Ser Thr Lys Tyr
            185                 190

Trp Ser Gly Asn Ser Glu Phe His Phe Tyr Ser Ile
            195                 200

Asn Val Gly Gly Phe Phe Lys Leu Arg Ser Gly Glu
```

-continued

```
            205                 210                 215
Glu Ile Ser Ile Glu Val Ser Asn Pro Ser Leu Leu
                220                 225

Asp Pro Asp Gln Asp Ala Thr Tyr Phe Gly Ala Phe
        230                 235                 240

Lys Val Arg Asp Ile Asp
                245
```

Sequence ID No. 18
Sequence Length: 735
Sequence Type: nucleic acid
Strandedness: 1
Topology: linear
Molecule Type: cDNA to mRNA
Sequence:

```
GCGCAGATGG ATCCTAACAG AATATCAGAA GACAGCACTC ACTGCTTTTA TAGAATCCTG   60
AGACTCCATG AAAACGCAGG TTTGCAGGAC TCGACTCTGG AGAGTGAAGA CACACTACCT  120
GACTCCTGCA GGAGGATGAA ACAAGCCTTT CAGGGGCCG TGCAGAAGGA ACTGCAACAC   180
ATTGTGGGGC GACAGCGCTT CTCAGGAGCT CCAGCTATGA TGGAAGGCTC ATGGTTGGAT  240
GTGGCCCAGC GAGGCAAGCC TGAGGCCCAG CCATTTGCAC ACCTCACCAT CAATGCTGCC  300
AGCATCCCAT CGGGTTCCCA TAAAGTCACT CTGTCCTCTT GGTACCACGA TCGAGGCTGG  360
GCCAAGATCT CTAACATGAC GTTAAGCAAC GGAAAACTAA GGGTTAACCA AGATGGCTTC  420
TATTACCTGT ACGCCAACAT TTGCTTTCGG CATCATGAAA CATCGGGAAG CGTACCTACA  480
GACTATCTTC AGCTGATGGT GTATGTCGTT AAAACCAGCA TCAAAATCCC AAGTTCTCAT  540
AACCTGATGA AAGGAGGGAG CACGAAAAAC TGGTCGGGCA ATTCTGAATT CCACTTTTAT  600
TCCATAAATG TTGGGGGATT TTTCAAGCTC CGAGCTGGTG AAGAAATTAG CATTCAGGTG  660
TCCAACCCTT CCCTGCTGGA TCCGGATCAA GATGCGACGT ACTTTGGGGC TTTCAAAGTT  720
CAGGACATAG ACTGA                                                   735
```

Sequence ID No. 19
Sequence Length: 741
Sequence Type: nucleic acid
Strandedness: 1
Topology: linear
Molecule Type: cDNA to mRNA
Sequence:

```
GCGCAGATGG ATCCTAATAG AATATCAGAA GATGGCACTC ACTGCATTTA TAGAATTTTG   60
AGACTCCATG AAAATGCAGA TTTTCAAGAC ACAACTCTGG AGAGTCAAGA TACAAAATTA  120
ATACCTGATT CATGTAGGAG AATTAAACAG GCCTTTCAAG GAGCTGTGCA AAAGCAATTA  180
CAACATATCG TTGGATCACA GCACATCAGA GCAGAGAAAG CGATGGTGGA TGGCTCATGG  240
TTACATCTGG CCAAGACGAG CAAGCTTGAA GCTCAGCCTT TTGCTCATCT CACTATTAAT  300
GCCACCGACA TCCCATCTGG TTCCCATAAA GTGAGTCTGT CCTCTTGGTA CCATGATCGG  360
GGTTGGGCCA AGATCTCCAA CATGACTTTT AGCAATGGAA AACTAATAGT TAATCAGGAT  420
GGCTTTTATT ACCTGTATGC CAACATTTGC TTTCGACATC ATGAAACTTC AGGAGACCTA  480
GCTACAGAGT ATCTTCAACT AATGGTGTAC GTCACTAAAA CCAGCATCAA AATCCCAAGT  540
TCTCATACCC TGATGAAAGG AGGAAGCACC AAGTATTGGT CAGGGAATTC TGAATTCCAT  600
TTTTATTCCA TAAACGTTGG TGGATTTTTT AAGTTACGGT CTGGAGAGGA AATCAGCATC  660
GAGGTCTCCA ACCCCTCCTT ACTGGATCCG GATCAGGATG CAACATACTT TGGGGCTTTT  720
AAAGTTCGAG ATATAGATTG A                                            741
```

What is claimed is:

1. An antibody which specifically binds to osteoclastogenesis inhibitory factor binding molecule (OBM), wherein said antibody is antibody H-OBM 1, produced by a hybridoma identified by international deposit accession number FERM BP-6264.

2. A hybridoma that produces the antibody of claim 1.

3. A composition comprising the antibody of claim 1 and one or more agents selected from the group consisting of a stabilizer, a pH adjuster, a buffering agent, a solubility agent and a detergent.

4. An antibody which specifically binds to osteoclastogenesis inhibitory factor binding molecule (OBM), and competes with antibody H-OBM 1 for binding to OBM, wherein said antibody H-OBM 1 is produced by a hybridoma identified by international deposit accession number FERM BP-6264.

5. The antibody of claim 4, wherein said antibody is a monoclonal antibody.

6. The antibody of claim 4, wherein said antibody is IgG.

7. The antibody of claim 6, wherein said antibody is IgG1 or IgG2.

8. The antibody of claim 7, wherein said antibody is IgG2a or IgG2b.

9. The antibody of claim 4, wherein said antibody has a kappa light chain.

10. The antibody of claim 4, wherein said antibody is a human antibody.

11. The antibody of claim 4, wherein said antibody binds to OBM with a Kd of $1 \times 10^{-9}$ M or less.

12. The antibody of claim 4, wherein said antibody binds to OBM with a Kd of $1 \times 10^{-10}$ M or less.

13. The antibody of claim 4, wherein said antibody binds to OBM with a Kd in the order of $1 \times 10^{-11}$ M.

14. The antibody of claim 4, wherein said antibody binds both human OBM and mouse OBM.

15. The antibody of claim 4, wherein said antibody does not bind mouse OBM.

16. The antibody of claim 4, wherein said antibody can inhibit osteoclast-like cell formation.

17. The antibody of claim 4, wherein said antibody can inhibit bone resorbing activity.

18. A hybridoma that produces the antibody of claim 4.

19. A composition comprising the antibody of claim 4 and one or more agents selected from the group consisting of a stabilizer, a pH adjuster, a buffering agent, a solubility agent and a detergent.

20. An antibody which specifically binds to osteoclastogenesis inhibitory factor binding molecule (OBM), wherein said antibody is antibody H-OBM 4, produced by a hybridoma identified by international deposit accession number FERM BP-6265.

21. A hybridoma that produces the antibody of claim 20.

22. A composition comprising the antibody of claim 20, and one or more agents selected from the group consisting of a stabilizer, a pH adjuster, a buffering agent, a solubility agent and a detergent.

23. An antibody which specifically binds to osteoclastogenesis inhibitory factor binding molecule (OBM), and competes with antibody H-OBM 4 for binding to OBM wherein said antibody H-OBM 4 is produced by a hybridoma identified by international deposit accession number FERM BP-6265.

24. The antibody of claim 23, wherein said antibody is a monoclonal antibody.

25. The antibody of claim 23, wherein said antibody is IgG.

26. The antibody of claim 25, wherein said antibody is IgG1 or IgG2.

27. The antibody of claim 26, wherein said antibody is IgG2a or IgG2b.

28. The antibody of claim 23, wherein said antibody has a kappa light chain.

29. The antibody of claim 23, wherein said antibody is a human antibody.

30. The antibody of claim 23, wherein said antibody binds to OBM with a Kd of $1 \times 10^{-9}$ M or less.

31. The antibody of claim 23, wherein said antibody binds to OBM with a Kd of $1 \times 10^{-10}$ M or less.

32. The antibody of claim 23, wherein said antibody binds to OBM with a Kd in the order of $1 \times 10^{-11}$ M.

33. The antibody of claim 23, wherein said antibody binds both human OBM and mouse OBM.

34. The antibody of claim 23, wherein said antibody does not bind mouse OBM.

35. The antibody of claim 23, wherein said antibody can inhibit osteoclast-like cell formation.

36. The antibody of claim 23, wherein said antibody can inhibit bone resorbing activity.

37. A hybridoma that produces the antibody of claim 23.

38. A composition comprising the antibody of claim 23 and one or more agents selected from the group consisting of a stabilizer, a pH adjuster, a buffering agent, a solubility agent and a detergent.

39. An antibody which specifically binds to osteoclastogenesis inhibitory factor binding molecule (OBM), wherein said antibody is antibody H-OBM 9, produced by a hybridoma identified by international deposit accession number FERM BP-6266.

40. A hybridoma that produces the antibody of claim 39.

41. A composition comprising the antibody of claim 39 and one or more agents selected from the group consisting of a stabilizer, a pH adjuster, a buffering agent, a solubility agent and a detergent.

42. An antibody which specifically binds to osteoclastogenesis inhibitory factor binding molecule (OBM) and competes with antibody H-OBM 9 for binding to OBM, wherein said antibody H-OBM 9 is produced by a hybridoma identified by international deposit accession number FERM BP-6266.

43. The antibody of claim 42, wherein said antibody is a monoclonal antibody.

44. The antibody of claim 42, wherein said antibody is IgG.

45. The antibody of claim 44, wherein said antibody is IgG1 or IgG2.

46. The antibody of claim 45, wherein said antibody is IgG2a or IgG2b.

47. The antibody of claim 42, wherein said antibody has a kappa light chain.

48. The antibody of claim 42, wherein said antibody is a human antibody.

49. The antibody of claim 42, wherein said antibody binds to OBM with a Kd of $1\times10^{-9}$ M or less.

50. The antibody of claim 42, wherein said antibody binds to OBM with a Kd of $1\times10^{-10}$ M or less.

51. The antibody of claim 42, wherein said antibody binds to OBM with a Kd in the order of $1\times10^{-11}$ M.

52. The antibody of claim 42, wherein said antibody binds both human OBM and mouse OBM.

53. The antibody of claim 42, wherein said antibody does not bind mouse OBM.

54. The antibody of claim 42, wherein said antibody can inhibit osteoclast-like cell formation.

55. The antibody of claim 42, wherein said antibody can inhibit bone resorbing activity.

56. A hybridoma that produces the antibody of claim 42.

57. A composition comprising the antibody of claim 42 and one or more agents selected from the group consisting of a stabilizer, a pH adjuster, a buffering agent, a solubility agent and a detergent.

* * * * *

UNITED STATES PATENT AND TRADEMARK OFFICE
CERTIFICATE OF CORRECTION

PATENT NO.       : 7,449,185 B2
APPLICATION NO.  : 10/854300
DATED            : November 11, 2008
INVENTOR(S)      : Yamaguchi et al.

It is certified that error appears in the above-identified patent and that said Letters Patent is hereby corrected as shown below:

| Issued Patent | | 1. Description of Error |
|---|---|---|
| Column | Line | |
| Title Page Item (56) Page 2 Col. 2 | 57 | Under Other Publications, change "Material" to --Mineral--. |
| Title Page Item (56) Page 3 Col. 1 | 11 | Under Other Publications, change "Necrosis" to --Necroses--. |
| Title Page Item (56) Page 3 Col. 1 | 48 | Under Other Publications, change "Reconbinant" to --Recombinant--. |
| Title Page Item (56) Page 3 Col. 1 | 51 | Under Other Publications, change "Osteclasts" to --Osteoclasts--. |
| Title Page Item (56) Page 3 Col. 2 | 25 | Under Other Publications, change "Differentation" to --Differentiation--. |
| 4 | 50 | Change "OCIP" to --OCIF--. |
| 5 | 15 | Change "canbeused" to --can be used--. |
| 6 | 1 | Change "Toyopal650" to --Toyopal 650--. |
| 14 | 54 | Change "OBM/sOBMmonoclonal" to --OBM/sOBM monoclonal--. |
| 15 | 8 | Change "Eseherichia" to --Escherichia--. |
| 16 | 39 | After "(EIA)" insert --.--. |
| 22 | 41 | Change "GI72/p" to --GI724/p--. |
| 23 | 12 | After "(1L-1)" insert --.--. |
| 26 | 15 | Change "A two" to --Two--. |
| 28 | 23 (Approx.) | Change "consequtive" to --consecutive--. |
| 36 | 22 | Change "SOBM" to --sOBM--. |
| 41 | 7 | Change "PCEP" to --pCEP--. |
| 45 | 16 | Change "trichioroacetic" to --trichloroacetic--. |

UNITED STATES PATENT AND TRADEMARK OFFICE
CERTIFICATE OF CORRECTION

PATENT NO. : 7,449,185 B2  
APPLICATION NO. : 10/854300  
DATED : November 11, 2008  
INVENTOR(S) : Yamaguchi et al.

Page 2 of 2

It is certified that error appears in the above-identified patent and that said Letters Patent is hereby corrected as shown below:

| | | |
|---|---|---|
| 51 | 12 | Change "absrobance" to --absorbance--. |
| 53 | 63 | Change "SOBM" to --sOBM--. |
| 53 | 65 | Change "SOBM" to --sOBM--. |
| 54 | 38 | Change "tranformed" to --transformed--. |
| 55 | 9 | After "selected as a" delete "a". |
| 59 | 14 | Change "hs,OBM" to --hsOBM--. |
| 60 | 44 | Change "Aces" to --Ace$^{TM}$--. |
| 60 | 61 | Change "Acem" to --Ace$^{TM}$--. |
| 61 | 23 | Change "FERMBP-6264" to --FERM BP-6264--. |
| 61 | 24 | Change "FERMBP-6265" to --FERM BP-6265--. |
| 61 | 31 | Change "Antibodiy" to --Antibody--. |
| 65 | 40 | Change "FEPM" to --FERM--. |

Signed and Sealed this

Twenty-ninth Day of September, 2009

David J. Kappos
*Director of the United States Patent and Trademark Office*

SEQUENCE LISTING

<160> NUMBER OF SEQ ID NOS: 19

<210> SEQ ID NO 1
<211> LENGTH: 316
<212> TYPE: PRT
<213> ORGANISM: Mus musculus

<400> SEQUENCE: 1

```
Met Arg Arg Ala Ser Arg Asp Tyr Gly Lys Tyr Leu Arg Ser Ser Glu
 1               5                  10                  15

Glu Met Gly Ser Gly Pro Gly Val Pro His Glu Gly Pro Leu His Pro
            20                  25                  30

Ala Pro Ser Ala Pro Ala Pro Pro Ala Ala Ser Arg Ser
        35                  40                  45

Met Phe Leu Ala Leu Leu Gly Leu Gly Gln Val Val Cys Ser
    50                  55                  60

Ile Ala Leu Phe Leu Tyr Phe Arg Ala Gln Met Asp Pro Asn Arg Ile
 65                  70                  75                  80

Ser Glu Asp Ser Thr His Cys Phe Tyr Arg Ile Leu Arg Leu His Glu
                85                  90                  95

Asn Ala Gly Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
    130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
        195                 200                 205

Gln Asp Gly Phe Tyr Tyr Leu Tyr Ala Asn Ile Cys Phe Arg His His
    210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
        275                 280                 285

Ser Ile Gln Val Ser Asn Pro Ser Leu Leu Asp Pro Asp Gln Asp Ala
    290                 295                 300

Thr Tyr Phe Gly Ala Phe Lys Val Gln Asp Ile Asp
305                 310                 315
```

<210> SEQ ID NO 2
<211> LENGTH: 1538
<212> TYPE: DNA
<213> ORGANISM: Mus musculus

<400> SEQUENCE: 2

-continued

```
gccaggacct ctgtgaaccg gtcggggcgg gggccgcctg gccgggagtc tgctcggcgg        60
tgggtggccg aggaagggag agaacgatcg cggagcaggg cgcccgaact ccgggcgccg       120
cgccatgcgc cgggccagcc gagactacgg caagtacctg cgcagctcgg aggagatggg       180
cagcggcccc ggcgtcccac acgagggtcc gctgcacccc gcgccttctg caccggctcc       240
ggcgccgcca cccgccgcct cccgctccat gttcctggcc ctcctggggc tgggactggg       300
ccaggtggtc tgcagcatcg ctctgttcct gtactttcga gcgcagatgg atcctaacag       360
aatatcagaa gacagcactc actgctttta tagaatcctg agactccatg aaaacgcagg       420
tttgcaggac tcgactctgg agagtgaaga cacactacct gactcctgca ggaggatgaa       480
acaagccttt caggggccg tgcagaagga actgcaacac attgtgggc cacagcgctt        540
ctcaggagct ccagctatga tggaaggctc atggttggat gtggcccagc gaggcaagcc       600
tgaggcccag ccatttgcac acctcaccat caatgctgcc agcatcccat cgggttccca       660
taaagtcact ctgtcctctt ggtaccacga tcgaggctgg gccaagatct ctaacatgac       720
gttaagcaac ggaaaactaa gggttaacca agatggcttc tattacctgt acgccaacat       780
ttgctttcgg catcatgaaa catcgggaag cgtacctaca gactatcttc agctgatggt       840
gtatgtcgtt aaaaccagca tcaaaatccc aagttctcat aacctgatga aggagggag        900
cacgaaaaac tggtcgggca attctgaatt ccacttttat tccataaatg ttgggggatt       960
tttcaagctc cgagctggtg aagaaattag cattcaggtg tccaacccctt ccctgctgga     1020
tccggatcaa gatgcgacgt actttggggc tttcaaagtt caggacatag actgagactc      1080
atttcgtgga acattagcat ggatgtccta gatgtttgga aacttcttaa aaaatggatg      1140
atgtctatac atgtgtaaga ctactaagag acatggccca cggtgtatga aactcacagc      1200
cctctctctt gagcctgtac aggttgtgta tatgtaaagt ccataggtga tgttagattc      1260
atggtgatta cacaacggtt ttacaatttt gtaatgattt cctagaattg aaccagattg      1320
ggagaggtat tccgatgctt atgaaaaact tacacgtgag ctatggaagg gggtcacagt      1380
ctctgggtct aaccccctgga catgtgccac tgagaacctt gaaattaaga ggatgccatg     1440
tcattgcaaa gaaatgatag tgtgaagggt taagttcttt tgaattgtta cattgcgctg      1500
ggacctgcaa ataagttctt tttttctaat gaggagag                              1538
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 3

```
aaacgcaaaa aaccagaaag g                                                  21
```

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 4

```
gtaaaacgac ggccagt                                                       17
```

<210> SEQ ID NO 5

```
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 5
caggaaacag ctatgac                                                        17

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:primer OBM
      #8

<400> SEQUENCE: 6
aagccccaaa gtacgtcgca tc                                                  22

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:OBM HF

<400> SEQUENCE: 7
cgaagctttc gagcgcagat ggatcc                                              26

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:OBM XR

<400> SEQUENCE: 8
cctctagagt ctatgtcctg aagtttg                                             27

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:OBM3

<400> SEQUENCE: 9
atcagaagac agcactcact                                                     20

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:OBMSalR2

<400> SEQUENCE: 10
ggggtcgacc taggacatcc atgctaatgt tcc                                      33

<210> SEQ ID NO 11
<211> LENGTH: 317
<212> TYPE: PRT
<213> ORGANISM: Homo sapiens

<400> SEQUENCE: 11
```

```
Met Arg Arg Ala Ser Arg Asp Tyr Thr Lys Tyr Leu Arg Gly Ser Glu
 1               5                  10                  15

Glu Met Gly Gly Gly Pro Gly Ala Pro His Glu Gly Pro Leu His Ala
                 20                  25                  30

Pro Pro Pro Ala Pro His Gln Pro Ala Ala Ser Arg Ser Met
         35                  40                  45

Phe Val Ala Leu Leu Gly Leu Gly Leu Gly Gln Val Val Cys Ser Val
     50                  55                  60

Ala Leu Phe Phe Tyr Phe Arg Ala Gln Met Asp Pro Asn Arg Ile Ser
 65                  70                  75                  80

Glu Asp Gly Thr His Cys Ile Tyr Arg Ile Leu Arg Leu His Glu Asn
                 85                  90                  95

Ala Asp Phe Gln Asp Thr Thr Leu Glu Ser Gln Asp Thr Lys Leu Ile
                100                 105                 110

Pro Asp Ser Cys Arg Arg Ile Lys Gln Ala Phe Gln Gly Ala Val Gln
            115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
                180                 185                 190

Trp Ala Lys Ile Ser Asn Met Thr Phe Ser Asn Gly Lys Leu Ile Val
            195                 200                 205

Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 12
<211> LENGTH: 954
<212> TYPE: DNA
<213> ORGANISM: Homo sapiens

<400> SEQUENCE: 12
atgcgccgcg ccagcagaga ctacaccaag tacctgcgtg gctcggagga gatgggcggc    60
ggccccggag cccgcacga gggccccctg cacgccccgc cgccgcctgc ccgcaccag    120 cccccctgccg cctcccgctc catgttcgtg gccctcctgg gctgggggct gggccaggtt    180
gtctgcagcg tcgccctgtt cttctatttc agagcgcaga tggatcctaa tagaatatca    240
gaagatggca ctcactgcat ttatagaatt ttgagactcc atgaaaatgc agattttcaa    300
gacacaactc tggagagtca agatacaaaa ttaatacctg attcatgtag agaattaaaa    360
```

```
caggcctttc aaggagctgt gcaaaaggaa ttacaacata tcgttggatc acagcacatc       420
agagcagaga aagcgatggt ggatggctca tggttagatc tggccaagag gagcaagctt       480
gaagctcagc cttttgctca tctcactatt aatgccaccg acatcccatc tggttcccat       540
aaagtgagtc tgtcctcttg gtaccatgat cggggttggg ccaagatctc caacatgact       600
tttagcaatg gaaaactaat agttaatcag gatggctttt attacctgta tgccaacatt       660
tgctttcgac atcatgaaac ttcaggagac ctagctacag agtatcttca actaatggtg       720
tacgtcacta aaccagcat caaaatccca agttctcata ccctgatgaa aggaggaagc       780
accaagtatt ggtcagggaa ttctgaattc cattttatt ccataaacgt tggtggattt       840
tttaagttac ggtctggaga ggaaatcagc atcgaggtct ccaaccccctc cttactggat       900 ccggatcagg atgcaacata ctttggggct tttaaagttc gagatataga ttga            954

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:human OBM SF

<400> SEQUENCE: 13
ggcgtacgca gagcgcagat ggatcct                                            27

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 14
ggggtcgacc atccaggaaa tatcataaca ctcc                                    34

<210> SEQ ID NO 15
<211> LENGTH: 951
<212> TYPE: DNA
<213> ORGANISM: Mus musculus

<400> SEQUENCE: 15
atgcgccggg ccagccgaga ctacggcaag tacctgcgca gctcggagga gatgggcagc       60
ggccccggcg tcccacacga gggtccgctg caccccgcgc cttctgcacc ggctccggcg       120
ccgccacccg ccgcctcccg ctccatgttc ctggccctcc tggggctggg actgggccag       180
gtggtctgca gcatcgctct gttcctgtac tttcgagcgc agatggatcc taacagaata       240
tcagaagaca gcactcactg ctttttataga atcctgagac tccatgaaaa cgcaggtttg       300
caggactcga ctctggagag tgaagacaca ctacctgact cctgcaggag gatgaaacaa       360
gcctttcagg gggccgtgca gaaggaactg caacacattg tggggccaca gcgcttctca       420
ggagctccag ctatgatgga aggctcatgg ttggatgtgg cccagcgagg caagcctgag       480
gcccagccat ttgcacacct caccatcaat gctgccagca tcccatcggg ttcccataaa       540
gtcactctgt cctcttggta ccacgatcga ggctgggcca agatctctaa catgacgtta       600
agcaacggaa aactaagggt taaccaagat ggcttctatt acctgtacgc caacatttgc       660
tttcggcatc atgaaacatc gggaagcgta cctacagact atcttcagct gatggtgtat       720
gtcgttaaaa ccagcatcaa aatcccaagt tctcataacc tgatgaaagg agggagcacg       780
```

```
aaaaactggt cgggcaattc tgaattccac ttttattcca taaatgttgg gggattttc     840 aagctccgag ctggtgaaga aattagcatt caggtgtcca acccttccct gctggatccg     900
gatcaagatg cgacgtactt tggggctttc aaagttcagg acatagactg a              951
```

<210> SEQ ID NO 16
<211> LENGTH: 244
<212> TYPE: PRT
<213> ORGANISM: Mus musculus

<400> SEQUENCE: 16

```
Ala Gln Met Asp Pro Asn Arg Ile Ser Glu Asp Ser Thr His Cys Phe
 1               5                  10                  15

Tyr Arg Ile Leu Arg Leu His Glu Asn Ala Gly Leu Gln Asp Ser Thr
            20                  25                  30

Leu Glu Ser Glu Asp Thr Leu Pro Asp Ser Cys Arg Arg Met Lys Gln
        35                  40                  45

Ala Phe Gln Gly Ala Val Gln Lys Glu Leu Gln His Ile Val Gly Pro
    50                  55                  60

Gln Arg Phe Ser Gly Ala Pro Ala Met Met Glu Gly Ser Trp Leu Asp
65                  70                  75                  80

Val Ala Gln Arg Gly Lys Pro Glu Ala Gln Pro Phe Ala His Leu Thr
                85                  90                  95

Ile Asn Ala Ala Ser Ile Pro Ser Gly Ser His Lys Val Thr Leu Ser
            100                 105                 110

Ser Trp Tyr His Asp Arg Gly Trp Ala Lys Ile Ser Asn Met Thr Leu
        115                 120                 125

Ser Asn Gly Lys Leu Arg Val Asn Gln Asp Gly Phe Tyr Tyr Leu Tyr
    130                 135                 140

Ala Asn Ile Cys Phe Arg His His Glu Thr Ser Gly Ser Val Pro Thr
145                 150                 155                 160

Asp Tyr Leu Gln Leu Met Val Tyr Val Val Lys Thr Ser Ile Lys Ile
                165                 170                 175

Pro Ser Ser His Asn Leu Met Lys Gly Gly Ser Thr Lys Asn Trp Ser
            180                 185                 190

Gly Asn Ser Glu Phe His Phe Tyr Ser Ile Asn Val Gly Gly Phe Phe
        195                 200                 205

Lys Leu Arg Ala Gly Glu Glu Ile Ser Ile Gln Val Ser Asn Pro Ser
    210                 215                 220

Leu Leu Asp Pro Asp Gln Asp Ala Thr Tyr Phe Gly Ala Phe Lys Val
225                 230                 235                 240

Gln Asp Ile Asp
```

<210> SEQ ID NO 17
<211> LENGTH: 246
<212> TYPE: PRT
<213> ORGANISM: Homo sapiens

<400> SEQUENCE: 17

```
Ala Gln Met Asp Pro Asn Arg Ile Ser Glu Asp Gly Thr His Cys Ile
 1               5                  10                  15

Tyr Arg Ile Leu Arg Leu His Glu Asn Ala Asp Phe Gln Asp Thr Thr
            20                  25                  30

Leu Glu Ser Gln Asp Thr Lys Leu Ile Pro Asp Ser Cys Arg Arg Ile
        35                  40                  45
```

```
Lys Gln Ala Phe Gln Gly Ala Val Gln Lys Glu Leu Gln His Ile Val
         50                  55                  60
Gly Ser Gln His Ile Arg Ala Glu Lys Ala Met Val Asp Gly Ser Trp
 65                  70                  75                  80
Leu Asp Leu Ala Lys Arg Ser Lys Leu Glu Ala Gln Pro Phe Ala His
                 85                  90                  95
Leu Thr Ile Asn Ala Thr Asp Ile Pro Ser Gly Ser His Lys Val Ser
            100                 105                 110
Leu Ser Ser Trp Tyr His Asp Arg Gly Trp Ala Lys Ile Ser Asn Met
        115                 120                 125
Thr Phe Ser Asn Gly Lys Leu Ile Val Asn Gln Asp Gly Phe Tyr Tyr
130                 135                 140
Leu Tyr Ala Asn Ile Cys Phe Arg His His Glu Thr Ser Gly Asp Leu
145                 150                 155                 160
Ala Thr Glu Tyr Leu Gln Leu Met Val Tyr Val Thr Lys Thr Ser Ile
                165                 170                 175
Lys Ile Pro Ser Ser His Thr Leu Met Lys Gly Gly Ser Thr Lys Tyr
            180                 185                 190
Trp Ser Gly Asn Ser Glu Phe His Phe Tyr Ser Ile Asn Val Gly Gly
        195                 200                 205
Phe Phe Lys Leu Arg Ser Gly Glu Glu Ile Ser Ile Glu Val Ser Asn
210                 215                 220
Pro Ser Leu Leu Asp Pro Asp Gln Asp Ala Thr Tyr Phe Gly Ala Phe
225                 230                 235                 240
Lys Val Arg Asp Ile Asp
                245
```

<210> SEQ ID NO 18
<211> LENGTH: 735
<212> TYPE: DNA
<213> ORGANISM: Mus musculus

<400> SEQUENCE: 18

```
gcgcagatgg atcctaacag aatatcagaa gacagcactc actgcttta  tagaatcctg      60
agactccatg aaaacgcagg tttgcaggac tcgactctgg agagtgaaga cacactacct    120
gactcctgca ggaggatgaa acaagccttt caggggccg  tgcagaagga actgcaacac    180
attgtggggc cacagcgctt ctcaggagct ccagctatga tggaaggctc atggttggat    240
gtggcccagc gaggcaagcc tgaggcccag ccatttgcac acctcaccat caatgctgcc    300
agcatcccat cgggttccca taaagtcact ctgtcctctt ggtaccacga tcgaggctgg    360
gccaagatct ctaacatgac gttaagcaac ggaaaactaa gggttaacca agatggcttc    420
tattacctgt acgccaacat tgctttcgg  catcatgaaa catcgggaag cgtacctaca    480
gactatcttc agctgatggt gtatgtcgtt aaaaccagca tcaaaatccc aagttctcat    540
aacctgatga aggagggag  cacgaaaaac tggtcgggca attctgaatt ccactttat    600
tccataaatg ttgggggatt tttcaagctc cgagctggtg aagaaattag cattcaggtg    660
tccaaccctt ccctgctgga tccggatcaa gatgcgacgt actttgggc  tttcaaagtt    720
caggacatag actga                                                    735
```

<210> SEQ ID NO 19
<211> LENGTH: 741
<212> TYPE: DNA
<213> ORGANISM: Homo sapiens -continued

```
<400> SEQUENCE: 19
gcgcagatgg atcctaatag aatatcagaa gatggcactc actgcattta tagaattttg      60
agactccatg aaaatgcaga ttttcaagac acaactctgg agagtcaaga tacaaaatta     120
atacctgatt catgtaggag aattaaacag gcctttcaag gagctgtgca aaaggaatta     180
caacatatcg ttggatcaca gcacatcaga gcagagaaag cgatggtgga tggctcatgg     240
ttagatctgg ccaagaggag caagcttgaa gctcagcctt ttgctcatct cactattaat     300
gccaccgaca tcccatctgg ttcccataaa gtgagtctgt cctcttggta ccatgatcgg     360
ggttgggcca agatctccaa catgactttt agcaatggaa aactaatagt taatcaggat     420
ggcttttatt acctgtatgc caacatttgc tttcgacatc atgaaacttc aggagaccta     480
gctacagagt atcttcaact aatggtgtac gtcactaaaa ccagcatcaa aatcccaagt     540
tctcataccc tgatgaaagg aggaagcacc aagtattggt cagggaattc tgaattccat     600
ttttattcca taaacgttgg tggatttttt aagttacggt ctggagagga aatcagcatc     660
gaggtctcca acccctcctt actggatccg gatcaggatg caacatactt tggggctttt     720
aaagttcgag atatagattg a                                              741
```